US012807985B2

(12) United States Patent
Samavati et al.

(10) Patent No.: US 12,807,985 B2
(45) Date of Patent: Nov. 24, 2026

(54) CYSTIC FIBROSIS SERUM BIOMARKERS

(71) Applicant: WAYNE STATE UNIVERSITY, Detroit, MI (US)

(72) Inventors: Lobelia Samavati, Beverly Hills, MI (US); Harvinder S. Talwar, Ypsilanti, MI (US); Sorin Draghici, Detroit, MI (US); Samer Hanoudi, Shelby Township, MI (US)

(73) Assignee: Wayne State University, Detroit, MI (US)

( * ) Notice: Subject to any disclaimer, the term of this patent is extended or adjusted under 35 U.S.C. 154(b) by 643 days.

(21) Appl. No.: 16/221,116

(22) Filed: Dec. 14, 2018

(65) Prior Publication Data

US 2019/0185923 A1 Jun. 20, 2019

Related U.S. Application Data

(60) Provisional application No. 62/599,255, filed on Dec. 15, 2017.

(51) Int. Cl.

| | |
|---|---|
| ***C12Q 1/6837*** | (2018.01) |
| ***C07K 14/00*** | (2006.01) |
| ***C12Q 1/6853*** | (2018.01) |
| ***C12Q 1/6883*** | (2018.01) |
| ***G01N 33/50*** | (2006.01) |
| ***G01N 33/68*** | (2006.01) |
| *C07K 14/435* | (2006.01) |
| *C07K 14/47* | (2006.01) |

(52) U.S. Cl.

CPC ............ *C12Q 1/6837* (2013.01); *C07K 14/00* (2013.01); *C12Q 1/6853* (2013.01); *C12Q 1/6883* (2013.01); *G01N 33/50* (2013.01); *G01N 33/6893* (2013.01); *C07K 14/435* (2013.01); *C07K 14/4712* (2013.01); *C12Q 2600/156* (2013.01); *C12Q 2600/158* (2013.01); *C12Q 2600/16* (2013.01); *G01N 2800/382* (2013.01)

(58) Field of Classification Search

CPC .. C07K 14/00; C07K 14/435; C07K 14/4712; C12Q 1/6837; C12Q 1/6853; C12Q 1/6883; C12Q 2600/156; C12Q 2600/158; C12Q 2600/16; G01N 2800/382; G01N 33/50; G01N 33/6893

See application file for complete search history.

(56) References Cited

U.S. PATENT DOCUMENTS

2006/0252922 A1* 11/2006 Macina ................ C12Q 1/6886 435/325

FOREIGN PATENT DOCUMENTS

WO WO2016141347 A2 9/2016

OTHER PUBLICATIONS

Protein NCBI, peptide ABC transporter substrate-binding protein [Burkholderia pseudomallei] GenBank: ALB12327.1, accessed on Nov. 8, 2023.*

Protein NCBI, AMP-dependent synthetase [Burkholderia cepacia] GenBank: KML61386.1, accessed on Nov. 8, 2023.*

Protein NCBI, Chain A, Methionine aminopeptidase PDB: 4FO7_A, accessed on Nov. 8, 2023.*

Aronoff, "Outer Membrane Permeability in Pseudomonas Cepacia: Diminished Porin Content in a Beta-Lactam-Resistant Mutant and in Resistant Cystic Fibrosis Isolates," Antimicrob. Agents Chemother., vol. 32, No. 11, 1988, pp. 1636-1639.

Bem et al., "Bacterial Histidine Kinases as Novel Antibacterial Drug Targets," ACS Chem. Biol. vol. 10, 2014, pp. 213-224.

Budding et al., "Anti-BPIFA1/SPLUNC1: A New Autoantibody Prevalent in Patients with Endstage Cystic Fibrosis," J. Cyst. Fibros., vol. 13, No. 3, 2014, pp. 281-288.

Carter, "Pathogen and Autoantigen Homologous Regions Within the Cystic Fibrosis Transmembrane Conductance Regulator (CFTR) Protein Suggest an Autoimmune Treatable Component of Cystic Fibrosis," FEMS Immunol. Med. Microbiol. vol. 62, No. 2, 2011, pp. 197-214.

Ciofu, "Pseudomonas Aeruginosa Chromosomal Beta-Lactamase in Patients with Cystic Fibrosis and Chronic Lung Infection. Mechanism of Antibiotic Resistance and Target of the Humoral Immune Response," APMIS Suppl., vol. 116, 2003, pp. 1-47.

Cohen & Prince, "Cystic Fibrosis: A Mucosal Immunodeficiency Syndrome," Nat. Med., vol. 18, No. 4, 2012, pp. 509-519.

Cuthbertson & Nodwell, "The TetR Family of Regulators," Microbiol. Mol. Biol. Rev., vol. 77, No. 3, 2013, pp. 440-475.

DeBoer et al., "Automated CT Scan Scores of Bronchiectasis and Air Trapping in Cystic Fibrosis," Chest., vol. 145, No. 3, 2014, pp. 593-603.

Downey et al., "The Relationship of Clinical and Inflammatory Markers to Outcome in Stable Patients with Cystic Fibrosis," Pediatr. Pulmonol., vol. 42, No. 3, 2007, pp. 216-220.

Gadsby et al., The ABC Protein Turned Chloride Channel Whose Failure Causes Cystic Fibrosis; Nature., vol. 440, No. 7083, 2006, pp. 477-483.

Hofer et al., "Decreased Expression of HLA-DQ and HLA-DR on Cells of the Monocytic Lineage in Cystic Fibrosis," J. Mol. Med., vol. 92, No. 12, 2014, pp. 1293-1304.

(Continued)

*Primary Examiner* — Erinne R Dabkowski

(74) *Attorney, Agent, or Firm* — Lee & Hayes, P.C.

(57) ABSTRACT

Systems, methods, devices, and kits are described that can be used to distinguish cystic fibrosis patients from healthy individuals and from lung cancer patients. The systems, methods, devices, and kits utilize one or more serum biomarkers.

10 Claims, 16 Drawing Sheets
(3 of 16 Drawing Sheet(s) Filed in Color)
Specification includes a Sequence Listing.

(56) References Cited

OTHER PUBLICATIONS

Lacy et al., "Serum IgG Response to an Outer Membrane Porin Protein of Burkholderia Cepacia in Patients with Cystic Fibrosis," FEMS Immunol. Med. Microbiol., vol. 17, No. 2, 1997, pp. 87-94.
Lee et al., "Thioredoxin and Dihydrolipoic Acid Inhibit Elastase Activity in Cystic Fibrosis Sputum," Am. J. Physiol. Lung Cell. Mol. Physiol., vol. 289, No. 5, 2005, pp. L875-L882.
Lin et al., "Autoantibody Approach for Serum-Based Detection of Head and Neck Cancer," Cancer Epidemiol. Biomarkers Prev., vol. 16, No. 11, 2007 pp. 2396-2405.
Liu et al., "Neutrophil Elastase and Elastase-Rich Cystic Fibrosis Sputum Degranulate Human Eosinophils in Vitro," Am. J. Physiol., vol. 276, No. 1 Pt. 1, 1999, pp. L28-L34.
MacEeachran et al., "Cif is Negatively Regulated by the TetR Family Repressor CifR," Infect. Immun., vol. 76, No. 7, 2008, pp. 3197-3206.
Mahenthiralingam et al., "Identification and Characterization of a Novel DNA Marker Associated with Epidemic Burkholderia Cepacia Strains Recovered from Patients with Cystic Fibrosis," J. Clin. Micribiol., vol. 35, No. 4, 1997, pp. 808-816.
Mayer-Hamblett et al., "Association Between Pulmonary Function and Spotum Biomarkers in Cystic Fibrosis," Am. J. Respir. Crit. Care Med., vol. 175, No. 8. 2007, pp. 822-828.
Meacham et al., "The Hdj-2/Hsc70 Chaperone Pair Facilitates Early Steps in CFTR Biogenesis," EMBO J., vol. 18, No. 6, 1999, pp. 1492-1505.
Pedersen et al., "An Immunoproteomic Approach for Identification of Clinical Biomarkers for Monitoring Disease: Application to Cystic Fibrosis," Mol. Cell. Proteomics, vol. 4, No. 8, 2005, pp. 1052-1060.
Rao et al., "Proteomic Identification of OprL as a Seromarker for Initial Diagnosis of Pseudomonas Aeruginosa Infection of Patients with Cystic Fibrosis," J. Clin. Microbiol., vol. 47, No. 8, 2009, pp. 2483-2488.
Rowe et al., "Potential Role of High-Mobility Group Box 1 in Cystic Fibrosis Airway Disease," Am. J. Respir. Crit. Care Med., vol. 178, No. 8, 2008, pp. 822-831.
Rubin et al., Thymosin beta4 Sequesters Actin in Cystic Fibrosis Sputum and Decreases Sputum Cohesivity In Vitro, Chest., vol. 130, No. 5, 2006, pp. 1433-1440.
Sagel et al., "Sputum Biomarkers of Inflammation in Cystic Fibrosis Lung Disease," Proc. Am. Thorac. Soc., vol. 4, No. 4, 2007, pp. 406-417.
Schneider & Hunke, "ATP-Binding-Cassette (ABC) Transport Systems: Functional and Structural Aspects of the ATP-Hydrolyzing Subunits/Domains," FEMS Microbiol. Rev., vol. 22, No. 1, pp. 1-20.
Sly et al., "Risk Factors for Bronchiectasis in Children with Cystic Fibrosis," N. Engl. J. Med., vol. 368, No. 21, 2013, pp. 1963-1970.
Srivastava et al., "Serum Proteomic Signature for Cystic Fibrosis Using an Antibody Microarray Platform," Mol. Genet. Metab., vol. 87, No. 4, 2006, pp. 303-310.
Stoltz et al., "Origins of Cystic Fibrosis Lung Disease," N. Engl. J. Med. vol. 372, No. 4, 2015, pp. 351-562.
Stolz & Wolf, "Endoplasmic Reticulum Associated Protein Degradation: A Chaperone Assisted Journey to Hell," Biochim. Biophys. Acta., vol. 1803, No. 6, 2010, pp. 694-705.
Talwar et al., "Detection of Cystic Fibrosis Serological Biomarkers Using a T7 Phage Display Library," Sci. Rep., vol. 7, No. 1, 2017, pp. 17745.
Talwar et al., "Development of a T7 Phage Display Library to Detect Sarcoidosis and Tuberculosis by a Panel of Novel Antigens," EBioMedicine, vol. 2, No. 4, 2015, pp. 342-350.
Talwar et al., "T7 Phage Display Library a Promising Strategy to Detect Tuberculosis Specific Biomarkers," Mycobact. Dis., vol. 6, No. 2, 2016, 214.
Valdivieso et al., "The Mitochondrial Complex I Activity is Reduced in Cells with Impaired Cystic Fibrosis Transmembrane Conductance Regulator (CFTR) Function," PLoS One, vol. 7, No. 11, 2012, pp. 1-12.
Von Bredow et al., "Surfactant Protein A and Other Bronchoalveolar Lavage Fluid Proteins are Altered in Cystic Fibrosis," Eur. Respir. J., vol. 17, No. 4, 2001, pp. 716-722.
Worthington et al., "Small Molecule Control of Bacterial Biofilms," Org. Biomol. Chem., vol. 10, No. 37, 2012, pp. 7457-7474.

* cited by examiner

FIG. 1A

| Rank | Clone (Peptide size) | Region of similarity of peptide |
|---|---|---|
| 1 | P51_BP3_25<br>(15aa)<br>SEQ ID NO: 6 | Id=10/12(83%) Gaps=0/12(0%) Length=1238<br>Query 1 LPRIFIELAQHQ 12 (SEQ ID NO: 31)<br>L RIFIELA H+ (SEQ ID NO: 32)<br>Sbjct 960 LERIFIELARHE 971 (SEQ ID NO: 33) |
| 2 | P51_BP3_47<br>(134 aa)<br>SEQ ID NO: 11 | Id= 123/127 (97%) Gaps=4/127 (3%) Length= 554<br>Query 2 AKYKETRLKEKEDALTRTELETLQKQKKVKKPKPEFPVYTPLETTYIQSYDHGTSIEEIE 61<br>AKYKETRLKEKEDALTRTELETLQKQKKVKKPKPEFPVYTPLETTYIQSYDHGTSIEEIE<br>Sbjct 250 AKYKETRLKEKEDALTRTELETLQKQKKVKKPKPEFPVYTPLETTYIQSYDHGTSIEEIE 309<br>Query 62 EQMETDDWLENRNRTQKKQAPEWTEEDLSQLTRSMETVKFPGGTPGRWEKIAHELGRSVT 121<br>EQMDDWLENRNRTQKKQAPEWTEEDLSQLTRSMVKFPGGTPGRWEKIAHELGRSVT<br>Sbjct 310 EQMDDWLENRNRTQKKQAPEWTEEDLSQLTRSM--VKFPGGTPGRWEKIAHELGRSVT 365<br>Query 122 DVTTKAK 128 (SEQ ID NO: 34)<br>DVTTKAK (SEQ ID NO: 35)<br>Sbjct 366 DVTTKAK 372 (SEQ ID NO: 36) |
| 3 | P51_BP3_104<br>(20aa)<br>SEQ ID NO: 14 | Id=9/10 (90%), Gaps=0/10 (0%) Length=412<br>Query 8 TTSPPSPPPA 17 (SEQ ID NO: 37)<br>TTSPPS PPA (SEQ ID NO: 38)<br>Sbjct 364 TTSPPSNPPA 373 (SEQ ID NO: 39) |
| 4 | P51_BP3_129<br>(16aa)<br>SEQ ID NO: 7 | Id=11/11 (100%) Gaps=0/11(0%) Length=280<br>Query 6 ELVDKLAAALE 16 (SEQ ID NO: 40)<br>ELVDKLAAALE (SEQ ID NO: 40)<br>Sbjct 264 ELVDKLAAALE 274 (SEQ ID NO: 40) |

FIG. 1B

| Rank | Clone (Peptide size) | Region of similarity of peptide |
| --- | --- | --- |
| 5 | P51_BP3_228<br>(23 aa)<br>SEQ ID NO: 12 | Id=7/10 (70%) Gaps=1/10 (10%) Length=377<br>Query 6 WRWDLVRGVW 15 (SEQ ID NO: 41)<br>WRWD V G W (SEQ ID NO: 42)<br>Sbjct 369 WRWDNVKG-W 377 (SEQ ID NO: 43) |
| 6 | P51_BP3_250<br>(16aa)<br>SEQ ID NO: 9 | Id=7/10(70%) Gaps=0/10(0%) Length=301<br>Query 7 TWVFLNLMQD 16 (SEQ ID NO: 44)<br>T VF NL QD (SEQ ID NO: 45)<br>Sbjct 262 TLVFANLIQD 271 (SEQ ID NO: 46) |
| 7 | P51_BP3_252<br>(29 aa)<br>SEQ ID NO: 13 | Id=10/12 (83%) Gaps=1/12 (8%) Length=575<br>Query 1 RDTGNSIFLSNG 12 (SEQ ID NO: 47)<br>RD G SIFLSNG (SEQ ID NO: 48)<br>Sbjct 189 RDSG-SIFLSNG 199 (SEQ ID NO: 49) |
| 8 | P51_BP3_254<br>(18aa)<br>SEQ ID NO: 2 | Id=8/11(72%) Gaps=0/11(0%) Length=399<br>Query 1 GKYNSTFTSSI 11 (SEQ ID NO: 50)<br>G Y+ TF SSI (SEQ ID NO: 51)<br>Sbjct 234 GSYDGTFASSI 244 (SEQ ID NO: 52) |

FIG. 1C

| Rank | Clone (Peptide size) | Region of similarity of peptide |
|---|---|---|
| 9 | P51_BP4_718<br>( 66 aa)<br>SEQ ID NO: 15 | Id=65/65 (100%) Gaps=0/65 (0%) Length=65<br>Query 2 ATAQTRLRSYSCASLRFSSATMSDKPDMAEIEKFDKSKLKKTETQEKNPLPSKETIEQEK 61<br>ATAQTRLRSYSCASLRFSSATMSDKPDMAEIEKFDKSKLKKTETQEKNPLPSKETIEQEK<br>Sbjct 1 ATAQTRLRSYSCASLRFSSATMSDKPDMAEIEKFDKSKLKKTETQEKNPLPSKETIEQEK 60<br>Query 62 QAGES 66 (SEQ ID NO: 53)<br>QAGES (SEQ ID NO: 53)<br>Sbjct 61 QAGES 65 (SEQ ID NO: 53) |
| 10 | P197_BP4_762<br>(9 aa)<br>SEQ ID NO: 16 | Id=7/8 (88%) Gaps=1/8(12%) Length=247<br>Query 1 IQHQHLGQ 8 (SEQ ID NO: 54)<br>IQ QHLGQ (SEQ ID NO: 55)<br>Sbjct 76 IQ-QHLGQ 82 (SEQ ID NO: 56) |
| 11 | P197_BP4_775<br>( 27 aa)<br>SEQ ID NO: 17 | Id=10/14 (71%) Gaps=1/14 (7%) Length= 609<br>Query 2 DKSVLLSLGRKKYG 15 (SEQ ID NO: 57)<br>DKSV LSL K YG (SEQ ID NO: 58)<br>Sbjct 226 DKSVRLSL-TKNYG 238 (SEQ ID NO: 59) |
| 12 | P197_BP4_805<br>(19 aa)<br>SEQ ID NO: 18 | Id= 7/12 (58%) Gaps=2/12 (16%) Length=402<br>Query 10 SVPSHKAT--WI 19 (SEQ ID NO: 60)<br>SVP + AT WI (SEQ ID NO: 61)<br>Sbjct 299 SVPAQNATGNWI 310 (SEQ ID NO: 62) |

FIG. 1D

| Rank | Clone (Peptide size) | Region of similarity of peptide |
|---|---|---|
| 13 | P197_BP4_830 (8aa) SEQ ID NO: 3 | Id=6/8(75%) Gaps=0/8(0%) Length=209<br>Query 1 YMCFSLPP 8 (SEQ ID NO: 3)<br>YM SLPP (SEQ ID NO: 63)<br>Sbjct 201 YMSASLPP 208 (SEQ ID NO: 64) |
| 14 | P197_BP4_834 (34aa) SEQ ID NO: 4 | Id=13/18(72%) Gaps=0/18(0%) Length=490<br>Query 14 RLRSGCVQGLVGMGRPVD 31 (SEQ ID NO: 65)<br>RL S C + G+V GRP+D (SEQ ID NO: 66)<br>Sbjct 305 RLDSYCFEGVVAPGRPID 322 (SEQ ID NO: 67) |
| 15 | P197_BP4_898 (17aa) SEQ ID NO: 1 | Id=7/8 (88%) Gaps=0/8 (0%) Length=342<br>Query 4 SEVATHQP 11 (SEQ ID NO: 68)<br>SEVATH P (SEQ ID NO: 69)<br>Sbjct 76 SEVATHPP 83 (SEQ ID NO: 70) |
| 16 | P197_BP4_925 (49aa) SEQ ID NO: 8 | Id=49/49(100%) Gaps=0/49(0%) Length=50<br>Query 1 DAPSPLPETTENVVCALGLTVGLVGIIIGTIFIIKGVRKSNAAERRGPL 49 (SEQ ID NO: 8)<br>DAPSPLPETTENVVCALGLTVGLVGIIIGTIFIIKG+RKSNAAERRGPL (SEQ ID NO: 71)<br>Sbjct 2 DAPSPLPETTENVVCALGLTVGLVGIIIGTIFIIKGLRKSNAAERRGPL 50 (SEQ ID NO: 72) |
| 17 | P197_BP4_926 (16 aa) SEQ ID NO: 19 | Id=7/9 (78%) Gaps=0/9(0%) Length=110<br>Query 4 MRQRVMMMG 12 (SEQ ID NO: 73)<br>MR+RV+MMG (SEQ ID NO: 74)<br>Sbjct 76 MRERVLMMG 84 (SEQ ID NO: 75) |

FIG. 1E

| Rank | Clone (Peptide size) | Region of similarity of peptide |
|---|---|---|
| 18 | P197_BP4_952<br>(12)<br>SEQ ID NO: 5 | Id=11/11(100%) Gaps=0/11(0%) Length=316<br>Query 2 ATSSLAVYSIL 12 (SEQ ID NO: 76)<br>ATSSLAVYSIL (SEQ ID NO: 76)<br>Sbjct 105 ATSSLAVYSIL 115 (SEQ ID NO: 76) |
| 19 | P197_BP4_1109<br>(213 aa)<br>SEQ ID NO: 20 | Id=205/206 (99%) Gaps 206/206 (0%) Length=335<br>Query 1 KIDRLDGAHAPELTKKVQRHASSGSFLPSANEHLKEDLNLRLKKLTHAAPCMLFMKGTPQ 60<br>KIDRLDGAHAPELTKKVQRHASSGSFLPSANEHLKEDLNLRLKKLTHAAPCMLFMKGTPQ<br>Sbjct 96 KIDRLDGAHAPELTKKVQRHASSGSFLPSANEHLKEDLNLRLKKLTHAAPCMLFMKGTPQ 155<br>Query 61 EPRCGFSKQMVEILHKHNIQFSSFDIFSDEEVRQGLKAYSSWPTYPQLYVSGELIGGLDI 120<br>EPRCGFSKQMVEILHKHNIQFSSFDIFSDEEVRQGLKAYSSWPTYPQLYVSGELIGGLDI<br>Sbjct 156 EPRCGFSKQMVEILHKHNIQFSSFDIFSDEEVRQGLKAYSSWPTYPQLYVSGELIGGLDI 215<br>Query 121 IKELEASEELDTICPKAPKLEERLKVLTNKASVMLFMKGNKQEAKCGFSKQILEILNSTG 180<br>IKELEASEELDTICPKAPKLEERLKVLTNKASVMLFMKGNKQEAKCGFSKQILEILNSTG<br>Sbjct 216 IKELEASEELDTICPKAPKLEERLKVLTNKASVMLFMKGNKQEAKCGFSKQILEILNSTG 275<br>Query 181 VEYETFDILEDEEVRQGLKAYSNWPS 206 (SEQ ID NO: 77)<br>VEYETFDILEDEEVRQGLKAYSNWP+ (SEQ ID NO: 78)<br>Sbjct 276 VEYETFDILEDEEVRQGLKAYSNWPT 301 (SEQ ID NO: 79) |
| 20 | P197_BP4_1114<br>(29aa)<br>SEQ ID NO: 10 | Id=13/26(50%) Gaps=5/26(19%)<br>Query 3 PPNNP-PPNT-NY---LTPTPHNHGK 23 (SEQ ID NO: 80)<br>P NP PPNT Y P PH+ K (SEQ ID NO: 81)<br>Sbjct 325 PATNPYPPNTWSYAKSIAPYPHDPAK 350 (SEQ ID NO: 82) |

FIG. 7

| Rank | Clone (Peptide Size) | Region of similarity of peptide |
|---|---|---|
| 21 | P51_BP3_34<br>(25aa)<br>SEQ ID NO: 21 | Id=12/20 (60%) Gaps=0/20(0%)<br>Query 6 VRSCTPAWVTERNFISKKKG 25 (SEQ ID NO: 83)<br>V S TPAWV + +I K G (SEQ ID NO: 84)<br>Sbjct 122 VQSSTPAWVSDITYIATKEG 141 (SEQ ID NO: 85) |
| 22 | P51_BP3_37<br>(18aa)<br>SEQ ID NO: 22 | Id=6/6(100%) Gaps=0/6(0%)<br>Query 4 NSTFTS 9 (SEQ ID NO: 86)<br>NSTFTS (SEQ ID NO: 86)<br>Sbjct 186 NSTFTS 191 (SEQ ID NO: 86) |
| 23 | P51_BP3_44<br>(24aa)<br>SEQ ID NO: 23 | Id=11/22(50%) Gaps=4/20(20%)<br>Query 2 ISPFTVTKHKPTSQGLEYLH 21 (SEQ ID NO: 87)<br>I PF TK KP LEY H (SEQ ID NO: 88)<br>Sbjct 406 IPPFKLTKNKP----LEYAH 421 (SEQ ID NO: 89) |
| 24 | P51_BP3_378<br>(87aa)<br>SEQ ID NO: 24 | Id=35/71 (49%) Gaps=7/71(10%)<br>Query 4 GRGRPSPLHVAQHSYTGVEAQPLNHQVLHVAGRDGLPVAVNGTLSDDDDVQSGPTAPSLT 63 (SEQ ID NO: 90)<br>G+G P PL + +HS+ + +VAG GLP AV + D + P S+T (SEQ ID NO: 91)<br>Sbjct 90 GKGWPQPLEIEEHSHADLANG-----_______-YVAGASGLPFAVLRAYAGSDLPKVNPLIRSVT 142 (SEQ ID NO: 92) |
| 25 | P51_BP4_382<br>(14aa)<br>SEQ ID NO: 25 | Id=7/9(78%) Gaps=0/9(0%)<br>Query 2 RMARSSWRR 10 (SEQ ID NO: 93)<br>RM RS WRR (SEQ ID NO: 94)<br>Sbjct 20 RMVRSAWRR 28 (SEQ ID NO: 95) |
| 26 | P51_BP4_741<br>(29aa)<br>SEQ ID NO: 26 | Id=8/8(100%) Gaps=0/8(0%)<br>Query 6 LFAALTVP 13 (SEQ ID NO: 96)<br>LFAALTVP (SEQ ID NO: 96)<br>Sbjct 126 LFAALTVP 133 (SEQ ID NO: 96) |
| 27 | 197_BP4_967<br>(5aa)<br>SEQ ID NO: 27 | Id=5/5(100%) Gaps=0/5(0%)<br>Query 1 SVRRG 5 (SEQ ID NO: 27)<br>SVRRG (SEQ ID NO: 27)<br>Sbjct 65 SVRRG 69 (SEQ ID NO: 27) |

CYSTIC FIBROSIS SERUM BIOMARKERS

CROSS-REFERENCE TO RELATED APPLICATION

This application claims priority to U.S. Provisional Application No. 62/599,255 filed on Dec. 15, 2017, which is incorporated herein by reference in its entirety as if fully set forth herein.

STATEMENT REGARDING FEDERALLY SPONSORED RESEARCH OR DEVELOPMENT

This invention was made with government support under grant R21 HL104481 awarded by the National Institutes of Health. The government has certain rights in the invention.

FIELD OF THE DISCLOSURE

The current disclosure provides systems and methods that can be used to distinguish cystic fibrosis patients from healthy individuals and from lung cancer patients. The systems and methods utilize serum biomarkers

BACKGROUND OF THE DISCLOSURE

There is a tremendous need for developing reliable serum based biomarkers in various diseases including proliferative disorder such as cancer, inflammatory diseases and infections as well as genetic disorders such as cystic fibrosis (CF).

Cystic fibrosis is an autosomal recessive disease caused by mutations in the gene encoding the CF transmembrane conductance regulator (CFTR) (Stoltz et al., *N Engl J Med* 372:351-562, 2015). Currently, there are more than 1300 various mutations in the CFTR gene that are known to cause the CF phenotype. The CF phenotype is characterized by chronic bacterial airway infections, neutrophilic inflammation with mucus in airways, progressive bronchiectasis, and advanced CF lung disease. Mutations in the CFTR gene affect the epithelial innate immune function in the lungs, resulting in exaggerated and ineffective airway inflammation that fails to eradicate pulmonary pathogens (Cohen & Prince, *Nat. Med* 18:509-519, 2012). Bacterial infections in CF are characterized by organisms that have substantial genetic flexibility to evade phagocytic clearance and develop resistance to multiple antibiotics (Id.). Repeated or chronic microbial infections are thought to be the major contributor to excessive inflammation leading to CF lung damage. In addition to chronic lung infections, CF patients may exhibit exocrine pancreatic insufficiency, diabetes mellitus, and sexual organ dysfunction.

Circulating autoantibodies and autoantigens in CF sera have been widely reported, yet their significance is unknown (Carter, *FEMS Immun Med Microbiol* 62:197-214, 2014; Budding et al., *J Cystic Fibrosis* 13:281-288, 2014; Pedersen et al., *Mol Cell Proteomics* 4:1052-1060, 2005). Various proteins and protein degradation products have been explored as candidate biomarkers for clinical outcome, such as neutrophil elastase, IL-8 (Mayer-Hamblet et al., *Am J Respir Clin Care Med.* 175:822-828, 2007), and degradation products of lung surfactant protein SP-A (von Bredow et al., *Eur Respir J.* 17:716-722, 2001; Downey et al., *Pediatric Pulmonol.* 42:216-220, 2007; Rowe et al., *Am J Respir Crit Care Med.* 178:822-831, 2008; Sagel et al., *Proc Am Thorac Soc* 4:406-417, 2007). A variety of proteomic approaches exploited antigenic biomarkers that could provide candidates for the diagnosis of infection, prognostic indicators or vaccine development. Pedersen et. al., used antibodies from CF patients to probe a protein array of body fluids prepared by two-dimensional gel electrophoresis for antigenic biomarker detection in *Pseudomonas aeruginosa* (*Mol Cell* Proteomics 4:1052-1060, 2005). Others identified the outer membrane protein OprL as a seromarker for the initial diagnosis of *Pseudomonas aeruginosa* infection in CF patients (Rao et al., *J Clin Microbiol.* 47:2483-2488, 2009).

Recently, a heterologous cDNA library derived from bronchoalveolar cells (BAL) and total white blood cells (WBC) from sarcoidosis patients was developed and combined with cultured human monocytes and embryonic lung fibroblasts cDNA libraries to build a complex sarcoidosis library (CSL) (Talwar et al., *EBioMedicine* 2:342-350, 2015; Talwar et al., *Mycobacterial Dis.: Tuberculosis & Leprosy* 6, doi:10.4172/2161-1068.1000214, 2016; see also WO 2016/141347).

SUMMARY OF THE DISCLOSURE

Because the complex sarcoidosis library (CSL) described previously (Talwar et al., *EBioMedicine* 2:342-350, 2015; Talwar et al., *Mycobacterial Dis.: Tuberculosis & Leprosy* 6, doi:10.4172/2161-1068.1000214, 2016; see also WO 2016/141347) represents a segment of the human lung microbiome, it was hypothesized that it could also contain potential antigens relevant to cystic fibrosis (CF). To test this, the CSL microarray platform was immunoscreened with sera from healthy controls, CF patients, and lung cancer patients. In this way, the power of antibody recognition present in human sera was used to identify potential serological biomarkers in CF.

The current disclosure provides biomarkers for cystic fibrosis. Of the described CF biomarkers, the following are upregulated in the sera of CS patients as compared to healthy controls: (i) Chain A, *Pseudomonas aeruginosa* Metap, In Mn; (ii) Beta-lactamase; (iii) histidine kinase; (iv) outer membrane porin; (v) dnaJ homolog; and (vi) γ-glutamyl-transpeptidase. (See Table 2). The following biomarkers are downregulated in the sera of CS patients as compared to healthy controls: (i) TetR family transcriptional regulator; (ii) AraC-family transcriptional regulator; (iii) HLA-DR alpha; (iv) thioredoxin like protein; (v) NADH dehydrogenase subunit 1; (vi) AMP-dependent synthetase; (vii) peptide ABC transporter substrate binding protein; and (viii) ketoacyl-ACP reductase. (See Table 2). See Table 3 and FIGS. 1A-1E, and Table 5 and FIG. 7, for ranking of clones and peptides associated with CF state, and Table 4 for useful groupings of clones and peptides.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some of the drawings submitted herein are better understood in color. Applicant considers the color versions of the drawings as part of the original submission.

FIGS. 1A-1E. Full length sequence analysis of top 20 CF phage clones using NCBI BLAST (see also Table 3).

(FIG. 2A) PCA score plots along the PC1 and 2 generated with 1070 clones of three groups: 1) healthy control samples (circles), 2) CF samples (triangles) and 3) lung cancer (LC) samples (squares). Along the PCA1 explaining a variance of only 0.18 and along the PC2 of 0.12. (FIG. 2B) The hierarchal clustering was applied on the healthy controls (solid squares; black text), CF patients (open squares; red text) and LC (open circles; blue text) with 1070 clones. (FIG. 2C) PCA score plots along the PC1 and 2 results when applied on the highly significant 20 CF clones. The PC1 explained 0.49 of variance, whereas PC2 explained 0.09 of variance. As shown the CF samples are well separated from the healthy controls and LC samples. (FIG. 2D) Hierarchal clustering using only the highly significant 20 CF clones (Table 3); key as for FIG. 2B. The green (hatched outline on the left) cluster includes LC and healthy control samples (no CF samples), the magenta (outline with circles on the right) cluster includes all the CF samples, few healthy control and two LC samples. This figure demonstrates better clustering with the highly significant 20 CF clones (FIGS. 2C and 2D) when compared with the clustering using all clones (FIGS. 2A and 2B).

As shown in FIG. 3, most CF samples clustered to the left side of the heat map plot, while the LC samples and healthy controls clustered to the right side of the plot indicating different expression profiles.

(FIG. 4A) Performance of the classifier on the testing sets. Box plots indicate the AUC values (y-axis) when the classifier model was applied on the 1000 test sets. The x-axis is accumulating sets of clones. The accumulation of the clones starts with the most frequent clone and then one clone added at a time to reach 100 clones. (FIG. 4B) Performance of the classifier models on the validation set. As indicated the classifier models when they were built using the significant clones shows a high AUC values on the testing sets as well as on the completely independent validating set. (FIG. 4C) The ROCs generated from the average of the 1000 runs of the classifier models when applied on the validation set (randomly selected healthy controls, CF and LC) using the 20 highly significant CF clones. The box plot shows the distribution of the sensitivities. The ROC curve demonstrates an excellent classification performance with an average AUC of 0.973 (95% CI: 0.07-0.094) with sensitivity of 0.99 (95% CI: 0.18-0.21) and specificity of 0.959 (95% CI: 0.11-0.15). These results indicate excellent performance of the naïve Bayes classifier on the 20 highly significant CF clones.

(FIG. 5A) ROCs for the top 6 significant clones that are increased (up-regulated) in CF sera compared to healthy control. (FIG. 5B) ROCs for the top 8 significant clones that are decreased (down-regulated) in CF compared to healthy controls. This figure demonstrates reasonable classification performance when the classification was applied just to one clone.

FIG. 7 Full length sequence analysis of the next 7 CF phage clones using NCBI BLAST (see also Table 5).

REFERENCE TO SEQUENCE LISTING

Figure 2A:
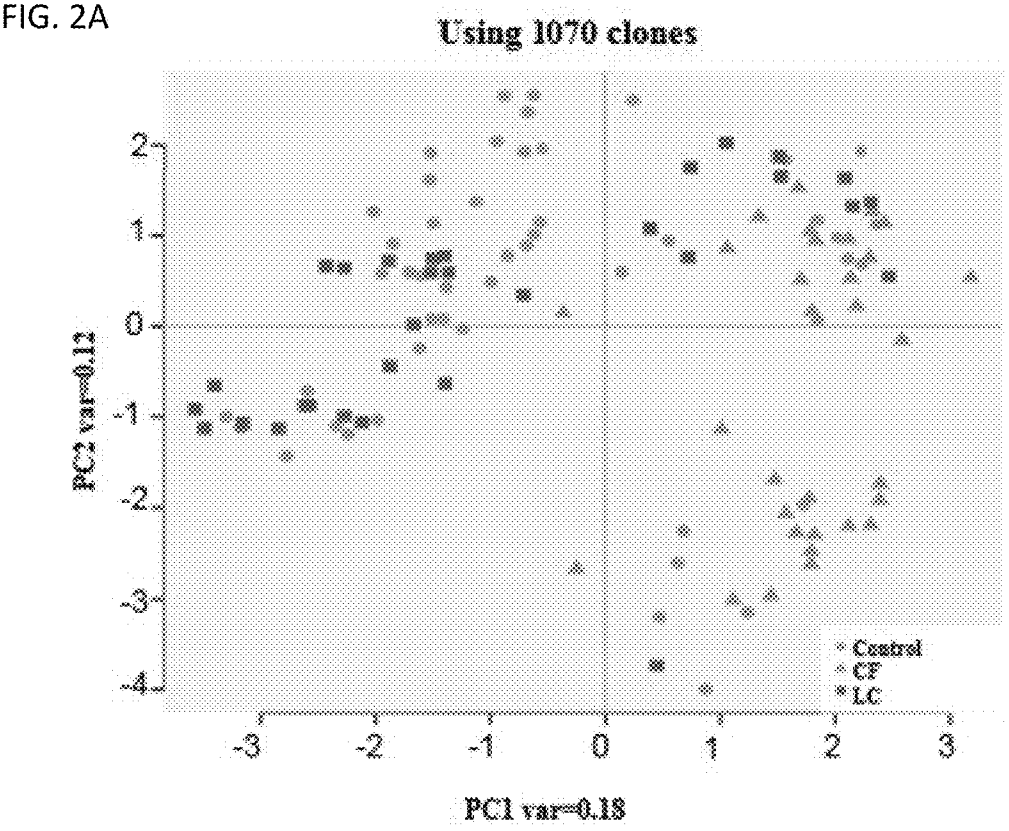
FIGS. 2A-2D show PCA and hierarchal clustering.

The nucleic acid sequences described herein are shown using standard letter abbreviations for nucleotide bases, as defined in 37 C.F.R. § 1.822. Only one strand of each nucleic acid sequence is shown, but the complementary strand is understood as included in embodiments where it would be appropriate. A computer readable text file, entitled "SeqListW063-0058US.txt" created on or about Aug. 15, 2023, with a file size of 44 KB, contains the sequence listing for this application and is hereby incorporated by reference in its entirety.

In the accompanying Sequence Listing:

SEQ ID NO: 1 is the peptide sequence of done P197_BP4_898, which corresponds to *Burkholderia cepacia* AraC-family transcriptional regulator:

DLSSEVATHQPIIACLP

SEQ ID NO: 2 is the peptide sequence of clones P51_BP3_254 and P51_BP3_113, which corresponds to *Burkholderia cepacia* Outer Membrane Porin

GKYNSTFTSSIIHNKNMK

SEQ ID NO: 3 is the peptide sequence of clone P197_BP4_830, which corresponds to *Burkholderia cepacia* TetR family transcriptional regulator:

YMCFSLPP

SEQ ID NO: 4 is the peptide sequence of done P197_BP4_834, which corresponds to *Burkholderia cepacia* AMP-dependent synthetase:

GITSARLGTGTGERLRSGCVQGLVGMGRPVDRAC

SEQ ID NO: 5 is the peptide sequence of done P197_BP4_952, which corresponds to *Homo sapiens* NADH dehydrogenase subunit 1:

SATSSLAVYSIL

SEQ ID NO: 6 is the peptide sequence of clones P51_BP3_25 and P197_BP4_817, which corresponds to *Pseudomonas* sp. BRH_c35 Histidine kinase:

LPRIFIELAQHQARV

SEQ ID NO: 7 is the peptide sequence of clones P51_BP3_129 and P51_BP4_382, which corresponds to *Pseudomonas Aeruginosa* Chain A Metap, In Mn Form

AGISRELVDKLAAALE

SEQ ID NO: 8 is the peptide sequence of clones P197_BP4_925, P51_BP4_704, and P51_BP3_296, which corresponds to *Homo sapiens* HLA-DR alpha:

DAPSPLPETTENVVCALGLTVGLVGIIIGTIFIIKGVRKSNAAERRGPL

SEQ ID NO: 9 is the peptide sequence of done P51_BP3_250, which corresponds to *Burkholderia cepacia* GG4 Beta-lactamase:

SRNCVNTWVFLNLMQD

SEQ ID NO: 10 is the peptide sequence of clone P197_BP4_1114, which corresponds to *Burkholderia cepacia* complex Peptide ABC transporter substrate binding protein:

LRPPNNPPPNTNYLTPTPHNHGKPTPLIQ

SEQ ID NO: 11 is the peptide sequence of done P51_BP3_47, which corresponds to *Homo sapiens* dnaJ homolog:

SAKYKETRLKEKEDALTRTELETLQKQKKVKKPKPEFPVYTPLETTYIQS

YDHGTSIEEIEEQMDDWLENRNRTQKKQAPEWTEEDLSQLTRSMVKFPGG

TPGRWEKIAHELGRSVTDVTTKAKLAAALE

SEQ ID NO: 12 is the peptide sequence of clone P51_BP3_228, which corresponds to *Pseudomonas aeruginosa* ABC transporter permease:

RDPQCWRWDLVRGVWVTGTDPSW

SEQ ID NO: 13 is the peptide sequence of clone P51_BP3_252, which corresponds to *Pseudomonas fluorescens* γ-glutamyltranspeptidase:

RDTGNSIFLSNGRRYALKFGWDTQFSFIF

SEQ ID NO: 14 is the peptide sequence of clone P51_BP3_104, which corresponds to *Burkholderia cepacia* Lytic transglucosylase:

PYVGMVATTSPPSPPPAVTT

SEQ ID NO: 15 is the peptide sequence of clone P51_BP4_718, which corresponds to *Homo sapiens* Thymosin β-4 TMSB4X protein (partial):

VATAQTRLRSYSCASLRFSSATMSDKPDMAEIEKFDKSKLKKTETQEKNP

LPSKETIEQEKQAGES

SEQ ID NO: 16 is the peptide sequence of clones P197_BP4_762 and P197_BP4873, which corresponds to *Pseudomonas aeruginosa* Ketoacyl-ACP reductase:

IQHQHLGQI

SEQ ID NO: 17 is the peptide sequence of done P197_BP4_775, which corresponds to *Pseudomonas aeruginosa* conjugal transfer protein:

VDKSVLLSLGRKKYGAVGSLSQSTGGH

SEQ ID NO: 18 is the peptide sequence of clone P197_BP4_805, which corresponds to *Burkholderia cepacia* hemolysin D:

SLGAMCLHSVPSHKATWI

SEQ ID NO: 19 is the peptide sequence of done P197_BP4_926, which corresponds to *Pseudomonas aeruginosa* Signal transduction histidine-protein kinase/phosphatase

VTLMRQRVMMMGRHTT

SEQ ID NO: 20 is the peptide sequence of clone P197_BP4_1109, which corresponds to *Homo sapiens* Thioredoxin like protein:

KIDRLDGAHAPELTKKVQRHASSGSFLPSANEHLKEDLNLRLKKLTHAAP

CMLFMKGTPQEPRCGFSKQMVEILHKHNIQFSSFDIFSDEEVRQGLKAYS

SWPTYPQLYVSGELIGGLDIIKELEASEELDTICPKAPKLEERLKVLTNK

ASVMLFMKGNKQEAKCGFSKQILEILNSTGVEYETFDILEDEEVRQGLKA

YSNWPSLRPHSSN

SEQ ID NO: 21 is the peptide sequence of done P51_BP3_34, which corresponds to *Pseudomonas aeruginosa* transposase:

SGSLEVRSCTPAWVTERNFISKKKG

SEQ ID NO: 22 is the peptide sequence of clone P51_BP3_37, which corresponds to *Pseudomonas aeruginosa* alkaline phosphatase

GKYNSTFTSSIIHNKNMK

SEQ ID NO: 23 is the peptide sequence of clone P51_BP3_44, which corresponds to *Campylobacter jejuni* DNA methyltransferase:

SISPFTVTKHKPTSQGLEYLHAFA

SEQ ID NO: 24 is the peptide sequence of clone P51_BP3_378, which corresponds to *Pseudomonas aeruginosa* 3-oxoadipate-succinyl-CoA transferase:

PVEGRGRPSPLHVAQHSYTGVEAQPLNHQVLHVAGRDGLPVAVNGTLSDD

DDVQSGPTAPSLTQPLTHEVLPAVLGWSLGDEQPVGP

SEQ ID NO: 25 is the peptide sequence of clone P51_BP4_382, which corresponds to *Streptomyces* sp. NRRL B-24720 glycosyl hydrolase:

SRMARSSWRRTSAA

SEQ ID NO: 26 is the peptide sequence of clone P51_BP4_741, which corresponds to *Pseudomonas aeruginosa* AraC family transcriptional regulator:

SATCSLFAALTVPDACPRTRPLRNSSFET

SEQ ID NO: 27 is the peptide sequence of clone P197_BP4_967, which corresponds to *Pseudomonas aeruginosa* peptidase S1:

SVRRG

SEQ ID NO: 28 is the nucleotide sequence of a T7 phage forward primer:

GTTCTATCCGCAACGTTATGG

SEQ ID NO: 29 is the nucleotide sequence of a T7 phage reverse primer:

GGAGGAAAGTCGTTTTTTGGGG

SEQ ID NO: 30 is the nucleotide sequence of a T7 phage sequence primer:

TGCTAAGGACAACGTTATCGG

SEQ ID NOs: 31-96 are additional sequences related to SEQ ID NOs: 1-27; shown in FIGS. 1 and 7.

DETAILED DESCRIPTION

Cystic fibrosis (CF) is characterized by a self-perpetuating cycle of airway obstruction, chronic bacterial infection, and vigorous inflammation that results in bronchiectasis, progressive obstructive lung disease, and marked shortening of life expectancy. Despite having identical CF transmembrane conductance regulator genotypes, individuals with F508del homozygous CF demonstrate significant variability in severity of pulmonary disease and infection. Non-invasive serological biomarkers that can aid to monitor disease progression or evaluate response to therapy would be extremely valuable. Several groups attempted to identify specific biomarkers to predict inflammation in CF using various biofluids such as sputum, BAL and serum (Sagel et al., *Proc Am Thorac Soc* 4:406-417, 2007; Srivastava et al., *Mol Gene Metabol.* 87:303-310, 2006). Most of those methods led to the discovery of a series of markers or expression signatures but failed to be useful in clinical practice (Srivastava et al., *Mol Gene Metabol.* 87:303-310, 2006).

In view of this context, as described herein a novel high throughput technology was applied to overcome the current gap by constructing phage-protein microarrays in which peptides were derived from a unique sarcoidosis cDNA library (Talwar et al., *EBioMedicine* 2:341-350, 2015) and expressed as a phage fusion protein. Through immunoscreening and rigorous statistical analysis, 27 highly significant CF clones were identified as biomarkers. These clones are able to discriminate between CF and healthy controls as well as lung cancer sera.

One important issue in biomarker discovery is the validation of biomarkers and sample selection. To overcome this issue, instead of using one training set, samples were randomly assigned into 1000 training sets. Then, the healthy controls and CF samples were compared for each pair of such random sets. The ranking of the top 20 clones was based on the significance and frequency of each clone (that is, how many times each clone appears significant at false discovery rate (FDR)<0.01).

The top 20 discriminating antigens for CF were sequenced and homologies in a public database were identified (see Table 3 & FIGS. 1A-1E). Seven additional antigens for CF were also characterized (see Table 5 & FIG. 7). The current disclosure provides that the following are upregulated in the sera of CS patients as compared to healthy controls (see Table 2):

(i) Chain A, *Pseudomonas aeruginosa* Metap, In Mn;
(ii) Beta-lactamase;
(iii) histidine kinase;
(iv) outer membrane porin;
(v) dnaJ homolog; and
(vi) gamma-(γ)-glutamyltranspeptidase.

The current disclosure provides that the following are downregulated in the sera of CS patients as compared to healthy controls (see Table 2):

(i) TetR family transcriptional regulator;
(ii) AraC-family transcriptional regulator;
(iii) HLA-DR alpha;
(iv) thioredoxin like protein;
(v) NADH dehydrogenase subunit 1;
(vi) AMP-dependent synthetase;
(vii) peptide ABC transporter substrate binding protein; and
(viii) ketoacyl-ACP reductase.

Table 4 describes particular useful groupings of clones and peptides.

The seven next most significant CF-discriminating clones (after the first 20 identified in Example 1) were also analyzed, as described in Example 2, Table 5, and FIG. 7.

The range length of identified peptides for CF antigens was between 8-213 amino acids (AA). Among the 20 most significant CF specific phage peptides, five out-of-frame peptides and one epitope were increased in sera of CF patients. One epitope (HLA-DR; SEQ ID NO: 8) was three times randomly selected (P51BP3_296, P51BP4_704 and P197_BP4_925), suggesting the importance of HLA-DR in pathology of CF. Recently, studies have demonstrated that the transcript levels of HLA-DR and HLA-DQ are reduced in CF patients (Hofer et al., *J Mol. Med.* 92:1293-1304, 2014).

Another epitope (SEQ ID NO: 11) was DnaJ homologue (Hdj)-1/heat shock protein (Hsp) 40, a protein chaperon, which along with its co-chaperone Hsp70 regulates protein folding and trafficking in the endoplasmic reticulum (ER) and facilitates degradation of misfolded proteins (Stolz & Wolf, *Biochim. Biophys. Acta Mol Cell* Res. 1803:694-705, 2010). It has been shown that Hsp40 and Hsp70 facilitate CFTR assembly (Meacham et al., *EMBO J* 18:1492-1505, 1999). It was found that DnaJ homologue was increased in sera of CF patients and had a negative correlation with BMI of CF subjects.

Another epitope (Thioredoxin like protein; SEQ ID NO: 20) was decreased in CF patients. Studies have shown that excessive neutrophil elastase activity in the airways of pediatric and adult CF patients resulted in lung damage (Sly et al., *NEJM* 368:1963-1970, 2013; DeBoer et al., *CHEST J* 145:593-603, 2014; Liu et al., *Am. J Physio—Lung Cell Mol Physiol.* 276:L28-L34, 1999). Disruption of neutrophil elastase activity by adding exogenous thioredoxin or dihydrolipoic acid in the sputum of CF patients reduced the neutrophil elastase activity (Lee et al., *Am J Physiol—Lung Cell Mol Physiol.* 289:L875-L882, 2005).

Another in-frame epitope with relevance to FEV1% predicted was Thymosin β-4 (TMSB4X; SEQ ID NO: 15). In vitro addition of Thymosin β-4 in the sputum of CF patients decreases the sputum cohesivity by depolymerizing actin (Rubin et al., *CHEST J* 130:1433-1440, 2006).

Among the first 20 sequenced CF-specific phage peptides, 16 antigens with relatively short out-of-frame peptides meeting the criteria as mimotopes (mimetic sequence of a true epitope; Wang et al., *NEJM* 353:1224-1235, 2006) were identified. Although the significance of mimotopes is not clear, it has been shown that some out-of-frame peptides can be immunogenic and can activate MHC class I molecules (Schirmbeck et al., *J Immunol.* 174:4647-4656, 2005). Due to smaller peptide sequences of mimotopes, they may have homology with diverse proteins. Prior studies using similar techniques have identified out-of-frame peptides (Wang et al., *NEJM* 353:1224-1235, 2006; Lin et al., *Cancer Epidem Biomarkers Prevention AACR* 16:2396-2405, 2007; Chatterjee et al., *Cancer Res* 66:1181-1190, 2006).

Two sequenced peptides (narX and barA_4; SEQ ID NOs: 6 and 19, respectively) with similarity to histidine kinases that belong to a large family of membrane-spanning proteins found in many prokaryotes and some eukaryotes were identified. This gene controls the bacterial virulence, growth and biofilm formation in CF patients (Worthington et al., *Org & Biomol Chem* 10:7457-7474, 2012). Similarly, IgG response to *Burkholderia cepacia* 80-kDa outer membrane protein has been shown to be significantly higher in patients with CF (Lacy et al., *FEMS Immuno Med Microbiol.* 17:87-94, 1997). Interestingly, when the correlation of biomarkers with sweat chloride values was explored, a good correlation with the outer membrane porin (Aronoff, *Antimicrob Agents Chemother.* 32:1636-2639, 1988) was found. Another significant biomarker detected (SEQ ID NO: 9) is beta-lactamase. Several studies have shown association between the development of resistance to beta-lactam antibiotics and high beta-lactamase production in CF patients (Ciofu, *APMIS Suppl.* 1-47, 2003).

Among 16 mimotopes, eight were found with decreased expression in CF patients (Table 2). Interestingly, one out of eight CF antigens with higher specificity and sensitivity (P197_BP4_830; SEQ ID NO: 3) belongs to repressor transcriptional regulators (MacEachran et al., *Infect & Immunity* 76:3197-3206, 2008; Mehanthiralingam et al., *J Clin Micribiol.* 35:808-816, 1997). One in vitro study showed that *Pseudomonas aeruginosa* toxin regulates TetR family transcriptional regulator and hence regulates CFTR expression through transcriptional repression (MacEachran et al., *Infect & Immunity* 76:3197-3206, 2008). Interestingly, TetR is involved in the regulation of antibiotic resistance and controls the expression of membrane-associated proteins that are involved in antibiotic resistance (Cutherbertson & Nodwell, *Microbiol Mol Biol Rev.* 77:440-475, 2013). Through immunoscreening, decreased NADPH dehydrogenase subunit I was identified. Similarly, studies have shown that mitochondrial complex I activity is reduced in cells with impaired CF transmembrane conductance regulator (Valdivieso et al., *PLoS One* 7:e48059, 2012). CFTR chloride channels belong to the superfamily of ABC transporter ATPases (Schneider & Hunke, *FEMS Microbiol Rev* 22:1-20, 1998). Interestingly, reduced ABC transporter substrate binding protein expression in CF patients was identified. The ABC transporters are widespread in prokaryotes and eukaryotes containing nucleotide-binding domains (NBD) and two transmembrane domains (TMDs). ATP hydrolysis on the NBD drives conformational changes in the TMD, resulting in alternating access from inside and outside of the cell for unidirectional transport across the lipid bilayer (Gadsby et al., *Nature* 440:477-483, 2006).

Novel antigens for CF were detected using a heterologous library derived from sarcoidosis subjects. Lungs are highly exposed to numerous bacteria and the described library is predominantly derived from sarcoidosis BAL cells and WBCs containing diverse immune cells, including macrophages that were exposed to various pathogens. Hence, it is postulated that the CSL represents a segment of the lung microbiome containing diverse antigens including CF-specific antigens, sarcoidosis and TB specific antigens (Talwar EBioMedicine 2:341-350, 2015; Talwar et al., *Mycobacterial Diseases: tuberculosis & leprosy.* 6, doi: 10.4172/2161-1068. 100214, 2016).

The phage display technology and immunoscreening has utilities not only in identifying of diagnostic biomarkers, but also may enable development of a novel targeted therapy utilizing the peptide sequences (mimotopes) as vehicles to deliver specific drugs. For instance, among highly significant clones, a sequence peptide homologous to histidine kinase (narX) with high specificity and sensitivity was found. Bacterial histidine kinases are promising targets for the development of antibacterial therapy. Currently efforts have been made to identify specific compounds targeting the inhibition of histidine kinase as antibacterial therapy (Bem et al., *ACS Chem Biol* 10:213-224, 2014). Additionally, this technology might enable discovery of unknown epitopes targeting specific bacterial antigens leading to immunogenicity and antibody production in CF subjects, as well as providing a better understanding of host immune defenses in CF subjects. Furthermore, this microarray platform can be hybridized to detect IgA in sera or saliva of CF patients that may have clinical values.

Up- or down-regulation of the markers, as indicated herein for particular markers, can be assessed by comparing a value (such as the level of activity or expression) to a relevant reference level. For example, the quantity of one or more markers can be indicated as a value. The value can be one or more numerical values resulting from the assaying of a sample, and can be derived, e.g., by measuring level(s) of the marker(s) in the sample by an assay performed in a laboratory, or from a dataset obtained from a provider such as a laboratory, or from a dataset stored on a server. The markers disclosed herein can be a protein marker or a nucleic acid marker (gene encoding the protein marker).

In particular embodiments, the systems and methods diagnose cystic fibrosis by assaying a sample obtained from a subject for the up- or down-regulation of two or more; three or more; four or more; five or more; six or more; seven or more; eight or more; nine or more or ten or more markers associated with cystic fibrosis disclosed herein. In further embodiments, the systems and methods diagnose cystic fibrosis by assaying a sample obtained from a subject for the up- or down-regulation of two; three; four; five; six; seven; eight; nine or ten markers associated with cystic fibrosis disclosed herein.

In one embodiment, the markers include (i) Chain A, *Pseudomonas aeruginosa* Metap, In Mn; (ii) Beta-lactamase; (iii) histidine kinase; (iv) outer membrane porin; (v) dnaJ homolog; and (vi) gamma-(γ)-glutamyltranspeptidase. In another embodiment, the markers include (i) TetR family transcriptional regulator; (ii) AraC-family transcriptional regulator; (iii) HLA-DR alpha; (iv) thioredoxin like protein; (v) NADH dehydrogenase subunit 1; (vi) AMP-dependent synthetase; (vii) peptide ABC transporter substrate binding protein; and (viii) ketoacyl-ACP reductase. In another embodiment, the markers include at least on upregulated and one downregulated (compared to healthy controls) marker from Table 2. In another embodiment, the markers include any four markers in Table 3; any five markers in Table 3; any seven markers in Table 3; any 10 markers in Table 3; any 12 markers in Table 3; any 15 markers in Table 3; or all 20 markers in Table 3. In another embodiment, the markers include any of the three sets of five clones set out in Table 4. In another embodiment, the markers include any one of the markers listed in Table 5; any two markers listed in Table 5; any four markers in Table 5, any five markers in Table 5; or all of the markers in Table 5. In yet additional embodiments, the markers include at least one marker from each of two or more of Tables 2, 3, 4, and/or 5. Yet other combinations of markers include sets in which the markers are selected to correspond to sequences from a single species (e.g., *Homo sapiens, Pseudomonas aeruginosa, Campylobacter jejuni, Streptomyces* sp., *Burkholderia cepacia, Pseudomonas fluorescens*); or to sequences selected to be from different species.

"Up-regulation" or "up-regulated" means an increase in the presence of a protein and/or an increase in the expression of its gene and/or an increase in the measurable function of its protein. "Down-regulation" or "down-regulated" means a decrease in the presence of a protein and/or a decrease in the expression of its gene and/or a decrease the measurable function of its protein. "Its gene" in reference to a particular protein refers to a nucleic acid sequence (used interchangeably with polynucleotide or nucleotide sequence) that encodes the particular protein. This includes various sequence polymorphisms, mutations, and/or sequence variants wherein such alterations do not substantially affect the identity or function of the particular protein. For example, in a sequence identity analysis, the specified protein would share at least 80% sequence identity; at least 81% sequence identity; at least 82% sequence identity; at least 83% sequence identity; at least 84% sequence identity; at least 85% sequence identity; at least 86% sequence identity; at least 87% sequence identity; at least 88% sequence identity; at least 89% sequence identity; at least 90% sequence identity; at least 91% sequence identity; at least 92% sequence identity; at least 93% sequence identity; at least 94% sequence identity; at least 95% sequence identity; at least 96% sequence identity; at least 97% sequence identity; at least 98% sequence identity or at least 99% sequence identity with the particular protein.

In the broadest sense, the value may be qualitative or quantitative. As such, where detection is qualitative, the systems and methods provide a reading or evaluation, e.g., assessment, of whether or not the marker is present in the sample being assayed. In yet other embodiments, the systems and methods provide a quantitative detection of whether the marker is present in the sample being assayed, i.e., an evaluation or assessment of the actual amount or relative abundance of the marker in the sample being assayed. In such embodiments, the quantitative detection may be absolute or, if the method is a method of detecting two or more different markers in a sample, relative. As such, the term "quantifying" when used in the context of quantifying a marker in a sample can refer to absolute or to relative quantification. Absolute quantification can be accomplished by inclusion of known concentration(s) of one or more control markers and referencing, e.g., normalizing, the detected level of the marker with the known control markers (e.g., through generation of a standard curve). Alternatively, relative quantification can be accomplished by comparison of detected levels or amounts between two or more different markers to provide a relative quantification of each of the two or more markers, e.g., relative to each other. The actual measurement of values of the markers can be determined at the protein or nucleic acid level using any method known in the art. In some embodiments, a marker is detected by contacting a sample with reagents (e.g., antibodies or nucleic acid primers), generating complexes of reagent and marker(s), and detecting the complexes.

The reagent can include a probe. A probe is a molecule that binds a target, either directly or indirectly. The target can be a marker, a fragment of the marker, or any molecule that is to be detected. In embodiments, the probe includes a nucleic acid or a protein. As an example, a protein probe can be an antibody. An antibody can be a whole antibody or a fragment of an antibody. A probe can be labeled with a detectable label. Examples of detectable labels include fluorescers, chemiluminescers, dyes, enzymes, enzyme substrates, enzyme cofactors, enzyme inhibitors, enzyme subunits, metal ions, and radioactive isotopes.

"Protein" detection includes detection of full-length proteins, mature proteins, pre-proteins, polypeptides, isoforms, mutations, post-translationally modified proteins and variants thereof, and can be detected in any suitable manner.

The function of a protein can be assayed by a relevant activity assay. Function is not substantially affected if there is no statistically significant difference in activity between the particular protein and the test protein. Exemplary activity assays include binding assays, or, if the protein is an enzyme, enzyme activity assays including, for example, protease assays, kinase assays, phosphatase assays, reductase assays, etc. Modulation of the kinetics of enzyme activities can be determined by measuring the rate constant KM using known algorithms, such as the Hill plot, Michaelis-Menten equation, linear regression plots such as Lineweaver-Burk analysis, and Scatchard plot.

Those skilled in the art will be familiar with numerous specific immunoassay formats and variations thereof which can be useful for carrying out the methods disclosed herein. See, e.g., E. Maggio, Enzyme-Immunoassay (1980), CRC Press, Inc., Boca Raton, Fla.; and U.S. Pat. Nos. 4,727,022; 4,659,678; 4,376,110; 4,275,149; 4,233,402; and 4,230,797.

Antibodies can be conjugated to a solid support suitable for a diagnostic assay (e.g., beads such as protein A or protein G agarose, microspheres, plates, slides or wells formed from materials such as latex or polystyrene) in accordance with known techniques, such as passive binding. Antibodies can be conjugated to detectable labels or groups such as radiolabels (e.g., $^{35}S$, $^{125}I$, $^{131}I$), enzyme labels (e.g., horseradish peroxidase, alkaline phosphatase), and fluorescent labels (e.g., fluorescein, Alexa, green fluorescent protein and modified or engineered versions thereof, rhodamine) in accordance with known techniques.

Examples of suitable immunoassays include immunoblotting, immunoprecipitation, immunofluorescence, chemiluminescence, electro-chemiluminescence (ECL), and/or enzyme-linked immunoassays (ELISA).

Up- or down-regulation of genes also can be detected using, for example, cDNA arrays, cDNA fragment fingerprinting, cDNA sequencing, clone hybridization, differential display, differential screening, FRET detection, liquid microarrays, PCR, RT-PCR, quantitative real-time RT-PCR analysis with TaqMan assays, molecular beacons, microelectric arrays, oligonucleotide arrays, polynucleotide arrays, serial analysis of gene expression (SAGE), and/or subtractive hybridization.

As an example, Northern hybridization analysis using probes which specifically recognize one or more marker sequences can be used to determine gene expression. Alternatively, expression can be measured using RT-PCR; e.g., polynucleotide primers specific for the differentially expressed marker mRNA sequences reverse-transcribe the mRNA into DNA, which is then amplified in PCR and can be visualized and quantified. Marker RNA can also be quantified using, for example, other target amplification methods, such as transcription mediated amplification (TMA), strand displacement amplification (SDA), and nucleic acid sequence based amplification (NASBA), or signal amplification methods (e.g., bDNA), and the like. Ribonuclease protection assays can also be used, using probes that specifically recognize one or more marker mRNA sequences, to determine gene expression.

Further hybridization technologies that may be used are described in, for example, U.S. Pat. Nos. 5,143,854; 5,288,644; 5,324,633; 5,432,049; 5,470,710; 5,492,806; 5,503,980; 5,510,270; 5,525,464; 5,547,839; 5,580,732; 5,661,028; and 5,800,992 as well as WO 95/21265; WO 96/31622; WO 97/10365; WO 97/27317; EP 373 203; and EP 785 280.

Proteins and nucleic acids can be linked to chips, such as microarray chips. See, for example, U.S. Pat. Nos. 5,143,854; 6,087,112; 5,215,882; 5,707,807; 5,807,522; 5,958,342; 5,994,076; 6,004,755; 6,048,695; 6,060,240; 6,090,556; and 6,040,138. Microarray refers to a solid carrier or support that has a plurality of molecules bound to its surface at defined locations. The solid carrier or support can be made of any material. As an example, the material can be hard, such as metal, glass, plastic, silicon, ceramics, and textured and porous materials; or soft materials, such as gels, rubbers, polymers, and other non-rigid materials. The material can also be nylon membranes, epoxy-glass and borofluorate-glass. The solid carrier or support can be flat, but need not be and can include any type of shape such as spherical shapes (e.g., beads or microspheres). The solid carrier or support can have a flat surface as in slides and micro-titer plates having one or more wells.

Binding to proteins or nucleic acids on microarrays can be detected by scanning the microarray with a variety of laser or CCD-based scanners, and extracting features with software packages, for example, Imagene (Biodiscovery, Hawthorne, CA), Feature Extraction Software (Agilent), Scanalyze (Eisen, M. 1999. SCANALYZE User Manual; Stanford Univ., Stanford, Calif. Ver 2.32.), or GenePix (Axon Instruments).

Embodiments disclosed herein can be used with high throughput screening (HTS). Typically, HTS refers to a format that performs at least about 100 assays, at least about 500 assays, at least about 1000 assays, at least about 5000 assays, at least about 10,000 assays, or more per day. When enumerating assays, either the number of samples or the number of protein or nucleic acid markers assayed can be considered.

Generally HTS methods involve a logical or physical array of either the subject samples, or the protein or nucleic acid markers, or both. Appropriate array formats include both liquid and solid phase arrays. For example, assays employing liquid phase arrays, e.g., for hybridization of nucleic acids, binding of antibodies or other receptors to ligand, etc., can be performed in multiwell or microtiter plates. Microtiter plates with 96, 384, or 1536 wells are widely available, and even higher numbers of wells, e.g., 3456 and 9600 can be used. In general, the choice of microtiter plates is determined by the methods and equipment, e.g., robotic handling and loading systems, used for sample preparation and analysis.

HTS assays and screening systems are commercially available from, for example, Zymark Corp. (Hopkinton, MA); Air Technical Industries (Mentor, OH); Beckman Instruments, Inc. (Fullerton, CA); Precision Systems, Inc. (Natick, MA), and so forth. These systems typically automate entire procedures including all sample and reagent pipetting, liquid dispensing, timed incubations, and final readings of the microplate in detector(s) appropriate for the assay. These configurable systems provide HTS as well as a high degree of flexibility and customization. The manufacturers of such systems provide detailed protocols for the various methods of HTS.

Reference Levels:

As stated previously, obtained marker values can be compared to a reference level. Reference levels can be obtained from one or more relevant datasets. A "dataset" as used herein is a set of numerical values resulting from evaluation of a sample (or population of samples) under a desired condition. The values of the dataset can be obtained, for example, by experimentally obtaining measures from a sample and constructing a dataset from these measurements. As is understood by one of ordinary skill in the art, the reference level can be based on e.g., any mathematical or statistical formula useful and known in the art for arriving at a meaningful aggregate reference level from a collection of individual datapoints; e.g., mean, median, median of the mean, etc. Alternatively, a reference level or dataset to create a reference level can be obtained from a service provider such as a laboratory, or from a database or a server on which the dataset has been stored.

A reference level from a dataset can be derived from previous measures derived from a population. A "population" is any grouping of subjects or samples of like specified characteristics. The grouping could be according to, for example, clinical parameters, clinical assessments, therapeutic regimens, disease status, severity of condition, etc.

Subjects include humans, veterinary animals (dogs, cats, reptiles, birds, hamsters, etc.) livestock (horses, cattle, goats, pigs, chickens, etc.), research animals (monkeys, rats, mice, fish, etc.) and other animals, such as zoo animals (e.g., bears, giraffe, elephant, lemurs, and other animals found in zoological parks).

In particular embodiments, conclusions are drawn based on whether a sample value is statistically significantly different or not statistically significantly different from a reference level. A measure is not statistically significantly different if the difference is within a level that would be expected to occur based on chance alone. In contrast, a statistically significant difference or increase is one that is greater than what would be expected to occur by chance alone. Statistical significance or lack thereof can be determined by any of various methods well-known in the art. Examples of commonly used measures of statistical significance include the t-test, the p-value, and other tests described herein. The p-value represents the probability of obtaining a given result equivalent to a particular datapoint, where the datapoint is the result of random chance alone. A result is often considered significant (not random chance) at a p-value less than or equal to 0.05.

In one embodiment, values obtained about the markers and/or other dataset components can be subjected to an analytic process with chosen parameters. The parameters of the analytic process may be those disclosed herein or those derived using the guidelines described herein. The analytic process used to generate a result may be any type of process capable of providing a result useful for classifying a sample, for example, comparison of the obtained value with a reference level, a linear algorithm, a quadratic algorithm, a decision tree algorithm, or a voting algorithm. The analytic process may set a threshold for determining the probability that a sample belongs to a given class. The probability preferably is at least at least 60%, at least 70%, at least 80%, at least 90%, at least 95% or higher.

In embodiments, the relevant reference level for a particular marker is obtained based on the particular marker in control subjects. Control subjects are those that are healthy and do not have cystic fibrosis. As an example, the relevant reference level can be the quantity of the particular marker in the control subjects.

In additional embodiments when more than one marker is assayed, values of the detected markers can be calculated into a score. Each value can be weighted evenly within an algorithm generating a score, or the values for particular markers can be weighted more heavily in reaching the score. For example, markers with higher sensitivity and/or specificity scores could be weighted more heavily than markers with lower sensitivity and/or specificity scores. For example, marker values for diagnosing cystic fibrosis may be weighted according to their ranking provided in Table 3 & FIGS. 1A-1E, and/or Table 5 & FIG. 7. Markers may also be grouped into classes, and each class given a weighted score. For example, marker values for diagnosing cystic fibrosis may be grouped into classes and weighted as follows (from highest weight to lowest weight): Class 1: Rank 1 and Rank 2 of Table 3; Class 2: Rank 3 and Rank 4 of Table 3; Class 3: Rank 5 and Rank 6 of Table 3; Class 4: Rank 7 and Rank 8 of Table 3; Class 5: Rank 9 and Rank 10 of Table 3, and so forth. As another example, marker values for diagnosing CF may be grouped into classes as described in Table 4.

Particular embodiments disclosed herein include obtaining a sample (e.g., blood sample; serum sample) from a subject suspected of having CF; assaying the sample for up- or down-regulation of one or more markers disclosed herein; determining one or more marker values based on the assaying; comparing the one or more marker values to a reference level; diagnosing CF in the subject according to the up- or down regulation of a marker, as described elsewhere herein.

A diagnosis according to the systems and methods disclosed herein can direct a treatment regimen. Treatments for CF are known, and include anti-inflammatory drugs, bronchodilators, mucus thinners and/or mucolytics, chest physical therapy (such as airway clearance techniques, including huff coughing, chest percussion, chest wall oscillation, and/or high-frequency chest oscillation), exercise, dietary modifications, treatments with CFTR modulators (such as Kalydeco (ivacaftor), Orkambi (lumacaftor with ivacaftor), or Symdeko (tezacaftor with ivacaftor)), surgery (e.g., sinus, bowel, or lung surgery) and so forth.

Kits:

Also provided herein are kits. Disclosed kits include materials and reagents necessary to assay a sample obtained from a subject for one or more CF markers disclosed herein. The materials and reagents can include those necessary to assay marker(s) disclosed herein according to any method described herein and/or known to one of ordinary skill in the art.

Particular embodiments include materials and reagents necessary to assay for up- or down-regulation of at least one marker protein in a sample. In particular embodiments, the kits include antibodies to marker proteins and/or can also include aptamers, epitopes or mimotopes or antigens to bind antibodies. Other embodiments additionally or alternatively include oligonucleotides that specifically assay for one or more marker nucleic acids based on homology and/or complementarity with marker nucleic acids. The oligonucleotide sequences may correspond to fragments of the marker nucleic acids. For example, the oligonucleotides can be more than 200, 175, 150, 100, 50, 25, 10, or fewer than 10 nucleotides in length. Collectively, any molecule (e.g., antibody, aptamer, epitope, mimotope, oligonucleotide) that forms a complex with a marker is referred to as a marker binding agent herein.

Embodiments of kits can contain in separate containers marker binding agents either bound to a matrix, or packaged separately with reagents for binding to a matrix. In particular embodiments, the matrix is, for example, a porous strip. In some embodiments, measurement or detection regions of the porous strip can include a plurality of sites containing marker binding agents. In some embodiments, the porous strip can also contain sites for negative and/or positive controls. Alternatively, control sites can be located on a separate strip from the porous strip. Optionally, the different detection sites can contain different amounts of marker binding agents, e.g., a higher amount in the first detection site and lesser amounts in subsequent sites. Upon the addition of test sample, the number of sites displaying a detectable signal provides a quantitative indication of the amount of marker present in the sample. The detection sites can be configured in any suitably detectable shape and can be, e.g., in the shape of a bar or dot spanning the width (or a portion thereof) of a porous strip.

In some embodiments the matrix can be a solid substrate, such as a "chip." See, e.g., U.S. Pat. No. 5,744,305. In some embodiments the matrix can be a solution array; e.g., xMAP (Luminex, Austin, TX), Cyvera (Illumina, San Diego, CA), RayBio Antibody Arrays (RayBiotech, Inc., Norcross, GA), CellCard (Vitra Bioscience, Mountain View, CA) and Quantum Dots' Mosaic (Invitrogen, Carlsbad, CA).

Additional kit embodiments can include control formulations (positive and/or negative), and/or one or more detectable labels, such as fluorescein, green fluorescent protein, rhodamine, cyanine dyes, Alexa dyes, luciferase, and radiolabels, among others. Instructions for carrying out the assay, including, optionally, instructions for generating a score, can be included in the kit; e.g., written, tape, VCR, or CD-ROM.

In particular embodiments, the kits include materials and reagents necessary to conduct and immunoassay (e.g., ELISA). In particular embodiments, the kits include materials and reagents necessary to conduct hybridization assays (e.g., PCR). In particular embodiments, materials and reagents expressly exclude equipment (e.g., plate readers). In particular embodiments, kits can exclude materials and reagents commonly found in laboratory settings (pipettes; test tubes; distilled $H_2O$).

Numerous protein sequences are disclosed herein. The disclosure is not limited to the particularly disclosed protein sequences but instead also encompasses sequences including 80% sequence identity; 81% sequence identity; 82% sequence identity; 83% sequence identity; 84% sequence identity; 85% sequence identity; 86% sequence identity; 87% sequence identity; 88% sequence identity; 89% sequence identity; 90% sequence identity; 91% sequence identity; 92% sequence identity; 93% sequence identity; 94% sequence identity; 95% sequence identity; 96% sequence identity; 97% sequence identity; 98% sequence identity or 99% sequence identity.

When a protein sequence is provided, its gene sequences can be derived by one of ordinary skill in the art by, for example, consulting publicly available databases. In addition to the sequence identity parameters provided above, gene sequences that hybridize to derived sequences under high stringency conditions can also be included within the scope of the current disclosure. A gene or polynucleotide fragment "hybridizes" to another gene or polynucleotide fragment, such as a cDNA, genomic DNA, or RNA, when a single stranded form of the polynucleotide fragment anneals to the other polynucleotide fragment under the appropriate conditions of temperature and solution ionic strength. Hybridization and washing conditions are well known and exemplified in Sambrook, J., Fritsch, E. F. and Maniatis, T. Molecular Cloning: A Laboratory Manual, Second Ed., Cold Spring Harbor Laboratory Press, Cold Spring Harbor (1989), particularly Chapter 11 and Table 11.1 therein (incorporated by reference herein for its teachings regarding the same). The conditions of temperature and ionic strength determine the "stringency" of the hybridization. Stringency conditions can be adjusted to screen for moderately similar fragments (such as homologous sequences from distantly related organisms) to highly similar fragments (such as genes that duplicate functional enzymes from closely related organisms). Post-hybridization washes determine stringency conditions. One set of hybridization conditions to demonstrate that sequences hybridize uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. Stringent conditions use higher temperatures in which the washes are identical to those above except for the temperature of the final two 30 min washes in 0.2×SSC, 0.5% SDS is increased to 60° C. Highly stringent conditions use two final washes in 0.1SSC, 0.1% SDS at 65° C. Those of ordinary skill in the art will recognize that these temperature and wash solution salt concentrations may need to be adjusted as necessary according to factors such as the length of the hybridizing sequences.

Computer-Assisted Methods:

In embodiments, diagnosis of CF may be achieved in accordance with the previously disclosed methods through the use of a computing device to provide for a quicker, more reliable, and less labor intensive diagnosis.

Figure 9:
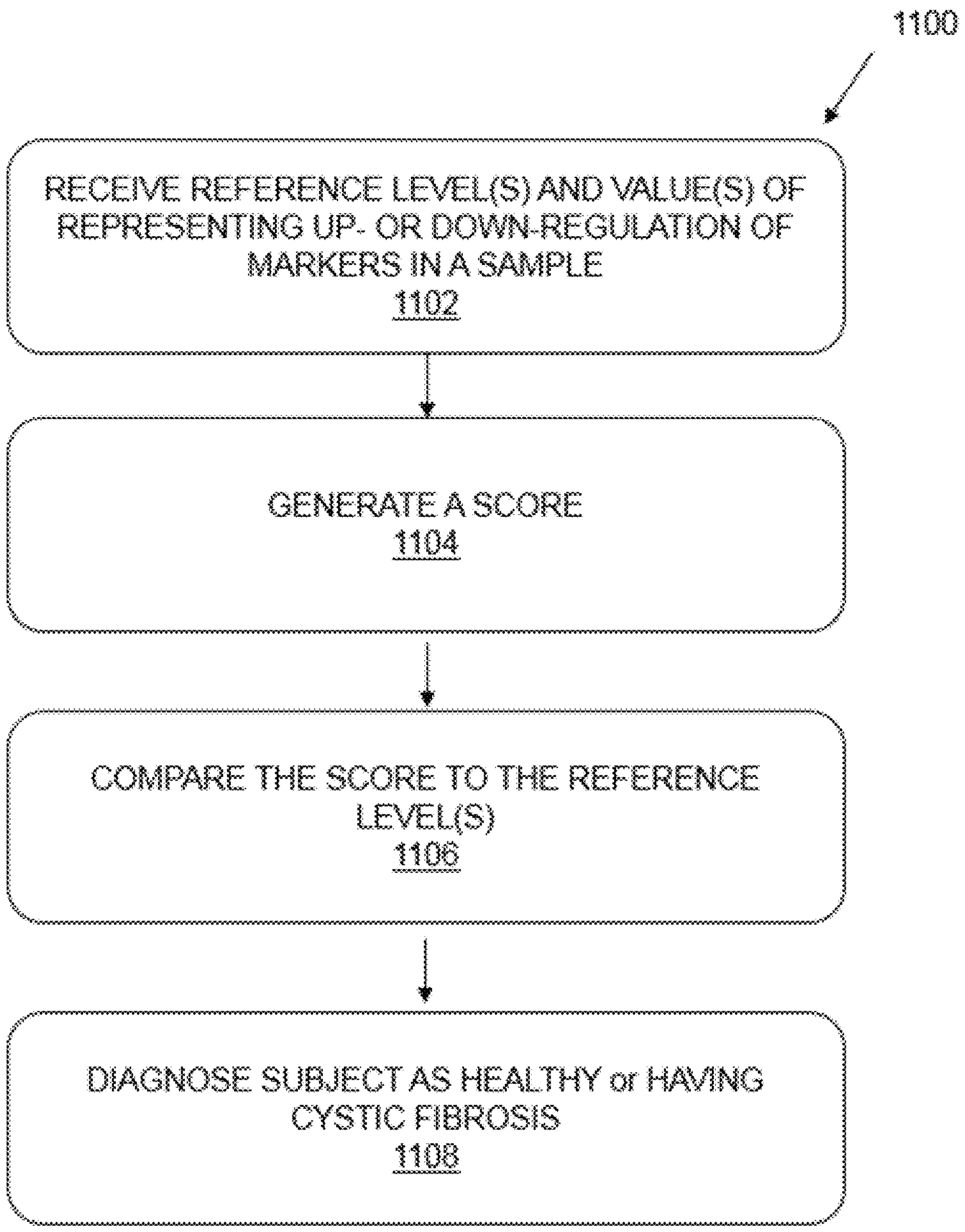
FIG. 9 shows an illustrative process for diagnosing CF.

FIG. 9 shows an illustrative schematic 1000 for diagnosing CF in a subject 1002 on a computing device 1008, including an illustrative diagram 1028 of a computing device 1008 implementing the diagnostic framework 1018. Sample biological material 1004 is collected from the subject 1002. That sample 1004 may be assayed for the presence of one or more markers. An indication of the up- or down-regulation of the markers is reflected by one or more marker values 1006 generated after assaying and analyzing the sample 1004. A computing device 1008 implementing the diagnostic framework 1018 will analyze and diagnose the subject 1002 as healthy, having CF. The diagnosis is published to a user via a graphical user interface 1026.

In embodiments, to enhance security, subject privacy, and compliance with government regulations, subject data like the subject's marker values 1006 may be deleted after it is used to generate a computer assisted diagnosis. Thus, the sample information will no longer exist as standalone information on the one or more computing devices 1028 implementing the diagnostic framework 1018. Thus, the only subject data available to the computing device 1008 will be integrated into the diagnosis provided by the one or more computing devices.

FIG. 9 includes an illustrative diagram 1028 of the computing device 1008. The computing device 1008 may contain one or more processing unit(s) 1012 and memory 1014, both of which may be distributed across one or more physical or logical locations. The processing unit(s) 1012 may include any combination of central processing units (CPUs), graphical processing units (GPUs), single core processors, multi-core processors, application-specific integrated circuits (ASICs), programmable circuits such as Field Programmable Gate Arrays (FPGA), and the like. One or more of the processing unit(s) 1012 may be implemented in software and/or firmware in addition to hardware implementations. Software or firmware implementations of the processing unit(s) 1012 may include computer- or machine-executable instructions written in any suitable programming language to perform the various functions described. Software implementations of the processing unit(s) 1012 may be stored in whole or part in the memory 1014.

Additionally, the functionality of the computing devices 1008 can be performed, at least in part, by one or more hardware logic components. For example, illustrative types of hardware logic components that can be used include Field-programmable Gate Arrays (FPGAs), Application-specific Integrated Circuits (ASICs), Application-specific Standard Products (ASSPs), System-on-a-chip systems (SOCs), Complex Programmable Logic Devices (CPLDs), etc.

Computing device 1008 may be connected to a network through one or more network connectors 1016 for receiving and sending information. The network may be implemented as any type of communications network such as a local area network, a wide area network, a mesh network, and ad hoc network, a peer-to-peer network, the Internet, a cable network, a telephone network, and the like. In embodiments, the computing device 1008 have a direct connection to one or more other devices (e.g. devices that output subject 1002 information, like marker values 1006, in electrical or electronic form) without the presence of an intervening network. The direct connection may be implemented as a wired connection or a wireless connection. A wired connection may include one or more wires or cables physically connecting the computing device 1008 to another device. For example, the wired connection may be created by a headphone cable, a telephone cable, a SCSI cable, a USB cable, an Ethernet cable, or the like. The wireless connection may be created by radio frequency (e.g., any version of Bluetooth, ANT, W-Fi IEEE 802.11, etc.), infrared light, or the like.

The computing device 1008 may be a supercomputer, a network server, a desktop computer, a notebook computer, a collection of server computers such as a server farm, a cloud computing system that uses processing power, memory, and other hardware resources distributed across multiple geographic locations, or the like. The computing device 1008 may include one or more input/output components(s) such as a keyboard, a pointing device, a touchscreen, a microphone, a camera, a display, a speaker, a printer, and the like.

Memory 1014 of the computing device 1008 may include removable storage, non-removable storage, local storage, and/or remote storage to provide storage of computer-readable instructions, data structures, program modules, and other data. The memory 1014 may be implemented as computer-readable media. Computer-readable media includes non-volatile computer-readable storage media, removable and non-removable media implemented in any method or technology for storage of information such as computer-readable instructions, data structures, program modules, or other data. Computer-readable storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other non-transmission medium that can be used to store information for access by a computing device.

The computing device 1008 includes multiple modules that may be implemented as instructions stored in the memory 1014 for execution by processing unit(s) 1012 and/or implemented, in whole or in part, by one or more hardware logic components or firmware. The diagnostic framework 1018 is contained within the computing device 1008 and may be implemented as instructions stored in the memory 1014 for execution by the processing unit(s) 1012, by hardware logic components, or both.

A scoring module 1012 obtains from an external source an indication of the expression of the tested markers in a sample 1004 as one or more marker value(s) 1006. The marker values 1006 can be obtained from a microarray or any machine connected to the computing device 1008 either directly or through the network connectors 1016. The marker values 1006 may also be previously saved or stored on a separate computing device or computer-readable media prior to being transferred to the scoring module 1020. The marker values 1008 may also be inputted directly by a user, including a physician or laboratory technician, through any appropriate I/O method. Exemplary I/O methods include any methods making use of the previously mentioned input/output components such as a keyboard, camera, microphone, touchscreen, or scanner.

The scoring module 1020 also obtains a reference level corresponding to the one or more marker values 1006. As with the marker values 1006, the reference levels can be calculated, as previously explained, and stored in a reference level database 1024, on the computing device 1008. Those having skill in the art will appreciate, however, that the one or more reference levels 1024 may, in other embodiments, be obtained either directly or through the network connectors 1016 from one or more separate computing devices, machines, or computer readable media. The reference levels may also be directly inputted by the user.

The scoring module 1020 may partially process, normalize, rewrite, anonymize, or otherwise modify the marker values 1006 or reference levels 1024. The scoring module 1020 will generate a score based at least in part on the one or more marker values 1006. In some embodiments this score is equivalent to the one or more marker values. In other embodiments, the score will be generated based at least in the part on the marker values 1006 and a weight associated with each corresponding marker. For example, markers with higher sensitivity, specificity, or both could be weighted more heavily than markers with lower sensitivity or specificity. Alternative scores may be generated based on any other previously discussed analytic process.

The scoring module 1020 provides the generated score to a diagnostic module 1022. The diagnostic module compares the score to the reference level and diagnoses the subject 1002 based on a result of the comparison as having CF, not having CF. The diagnosis is published to the user via a graphical user interface 1026.

Illustrative Process:

For ease of understanding, the processes discussed in this disclosure are delineated as separate operations represented as independent blocks. However, these separately delineated operations should not be construed as necessarily order dependent in their performance. The order in which the process is described is not intended to be construed as a limitation, and any number of the described process blocks may be combined in any order to implement the process, or an alternate process. Moreover, it is also possible that one or more of the provided operations is modified or omitted.

FIG. 9 shows an illustrative process 1100 for diagnosing CF.

At 1102, one or more reference levels are received, as well as an indication of the expression of relevant markers in a sample. The indication of the one or more marker values may be received from a clinician who assayed the sample for the value, or they may be received from a database where the values from a previously performed assay have been stored.

At 1104, a score is generated at least partly based on the marker value. The score may be the same as the marker value, or it may be additionally based on a weight corresponding to each tested marker, or based in part on any other previously disclosed analytic process. Note that there may be a score for each marker, or there may be a single score based on an aggregation of data related to multiple marker values.

At 1106, the score is compared to one or more reference levels.

At 1108, a subject is diagnosed based on a result of the comparison 1106 as being healthy, having CF.

In embodiments, the subjects diagnosed with CF using the methods disclosed herein can be effectively treated with the appropriate therapy. As an example, treating subjects with CF includes delivering therapeutically effective amounts of an appropriate drug to alleviate one or more symptoms of CF.

In summary, a T7 phage display library derived from BALs and leukocytes of patients with CF that displays a significant segment of the potential antigens that can recognize IgG antibodies in CF sera with high accuracy has been developed. Furthermore, a set of CF clones that highly correlate with clinical measures such as, sweat chloride values, BMI and FEV1 has been identified. Microarray and immunoscreening has a value in clinical practice in antibody detection as it is non-invasive and requiring a minimal amount of blood. The identified sequences can be used to develop peptide/protein-coated magnetic nanoparticles for clinical testing or for applications in drug delivery (Rana et al., *Adv Drug Del Rev* 64:200-216, 2012). The present disclosure describes a novel approach to identify CF biomarkers, provides specific CF biomarkers so identified, and describes methods of their use.

Set 1 of Exemplary Embodiments

1. A kit for diagnosing cystic fibrosis (CF) from a serum sample derived from a subject, wherein the kit includes a plurality of binding domains, each binding domain binding a CF marker disclosed herein.

2. A kit for diagnosing CF from a serum sample derived from a subject, wherein the kit includes a plurality of binding domains, each binding domain binding a CF marker disclosed in Table 2.

3. A kit for diagnosing CF from a serum sample derived from a subject. wherein the kit includes a plurality of binding domains, each binding domain binding a CF marker disclosed within a group of Table 4.

4. The kit of any one of embodiments 1-3 wherein the binding domains are proteins.

5. The kit of any one of embodiments 1-3 wherein the binding domains bind antibodies.

6. The kit of any one of embodiments 1-3 wherein the binding domains include antibody binding domains.

7. The kit of any one of embodiments 4-6, further including a detectable label.

8. The kit of embodiment 6 wherein the detectable label is a radioactive isotope, enzyme, dye, fluorescent dye, magnetic bead, or biotin.

9. The kit according any one of embodiments 1-3 wherein the kit includes one or more reagents to perform an enzyme-linked immunosorbent assay (ELISA), a radioimmunoassay (RIA), a Western blot, an immunoprecipitation, an immunohistochemical staining, flow cytometry, fluorescence-activated cell sorting (FACS), an enzyme substrate color method, and/or an antigen-antibody agglutination.

10. A method of diagnosing CF in a subject including: obtaining a serum sample derived from the subject; assaying the sample for one or more markers selected from Table 3 and a detectable label; obtaining a value based on the assay; comparing the value to a reference level; and diagnosing the subject as healthy or having CF based on the up- or down-regulation of the one or more markers as demonstrated by the value and the reference level.

11. A method of diagnosing CF in a subject including: obtaining a serum sample derived from the subject; assaying the sample for one or more markers selected from Table 2 and a detectable label; obtaining a value based on the assay; comparing the value to a reference level; and diagnosing the subject as healthy or having CF based on the up- or down-regulation of the one or more markers as demonstrated by the value and the reference level.

12. A method of diagnosing CF in a subject including: obtaining a serum sample derived from the subject; assaying the sample for a group of markers of Table 4 and a detectable label; obtaining a value based on the assay; comparing the value to a reference level; and diagnosing the subject as healthy or having CF based on the up- or down-regulation of the group of markers as demonstrated by the value and the reference level.

13. A method of detecting binding between a labeled binding protein and a marker of Table 3 including contacting a sample with a labeled binding protein and detecting binding between the labeled binding protein and a marker of Table 3.

14. A method of detecting binding between a labeled binding protein and a marker of Table 2 including contacting a sample with a labeled binding protein and detecting binding between the labeled binding protein and a marker of Table 2.

15. A method of detecting binding between labeled binding proteins and a group of markers of Table 4 including contacting a sample with labeled binding proteins and detecting binding between the labeled binding proteins and a group of markers of Table 4.

Set 2 of Exemplary Embodiments

1. A kit for diagnosing cystic fibrosis (CF) from a serum sample derived from a subject, the kit including a detectable label and: (a) a plurality of binding domains, each of which binds a CF marker shown in: any one of SEQ ID NOs: 1-27; Table 2; or a set of five clones in Table 4; or (b) a plurality of nucleic acids, each of which binds a gene encoding a CF marker shown in: any one of SEQ ID NOs: 1-27; Table 2; or a set of five clones in Table 4.

2. The kit of embodiment 1, wherein the plurality of binding domains or the plurality of nucleic acids is bound to a solid surface.

3. The kit of embodiment 2, wherein the solid surface is an array or a microarray.

4. The kit of embodiment 3, wherein the microarray includes: at least two different proteins, each of which binds one of 4FO8, GEM_5327, narX, GEM_5047, DANJC10, PS113-4947, GEM_1794, APZ15_34865, HLA-DR, TXNL1, MT-ND1, VL15_07170, 135,2059, or fabG; at least two different proteins, each of which binds one of 4FO8, GEM_5327, narX, GEM_5047, DANJC10, or PS113-4947; at least two different proteins, each of which binds one of GEM_1794, APZ15_34865, HLA-DR, TXNL1, MT-ND1, VL15_07170, 135,2059, or fabG; at least two different proteins, each of which binds one of the CF biomarkers listed in Table 3 or Table 5; at least five different proteins, each of which binds one of the CF biomarkers listed as part of a set of five in Table 4; two or more of the amino acid sequences shown in SEQ ID NO: 1-27 or a fragment thereof at least 6 amino acids in length; two or more of the peptides shown in Table 2 or Table 5; at least two different nucleic acids, each of which binds to a gene encoding one of the CF biomarkers listed in Table 3 or Table 5; at least two different nucleic acids, each of which binds to a gene encoding one of 4FO8, GEM_5327, narX, GEM_5047, DANJC10, or PS113-4947; at least two different nucleic acids, each of which binds to a gene encoding one of GEM_1794, APZ15_34865, HLA-DR, TXNL1, MT-ND1, VL15_07170, 135,2059, or fabG; or at least five different nucleic acids, each of which binds to a gene encoding one of the CF biomarkers listed as part of a set of five in Table 4.

5. The kit of embodiment 1(a), wherein the binding domains: are proteins; and/or bind antibodies; and/or include antibody binding domain(s); and/or include an epitope; and/or include a mimotope.

6. The kit of embodiment 1, wherein the plurality is four or more.

7. The kit of embodiment 1 wherein the detectable label includes a radioactive isotope, enzyme, dye, fluorescent dye, magnetic bead, or biotin.

8. The kit embodiment 1, further including one or more reagents to perform an enzyme-linked immunosorbent assay (ELISA), a radioimmunoassay (RIA), a Western blot, an immunoprecipitation, an immunohistochemical staining, flow cytometry, fluorescence-activated cell sorting (FACS), an enzyme substrate color method, and/or an antigen-antibody agglutination.

9. A method of diagnosing cystic fibrosis in a subject, the method including: obtaining a serum sample derived from the subject; assaying the sample for one or more markers selected from the CF biomarkers listed in Table 2, Table 3, Table 4, or Table 5; obtaining a value based on the assay; comparing the value to a reference level; and diagnosing the subject as healthy or having CF based on the up- or down-regulation of the one or more markers as demonstrated by the value and the reference level.

10. The method of embodiment 9, wherein assaying the sample for one or more markers includes contacting the sample with a probe including a detectable label and that binds the one or more markers.

11. The method of embodiment 9, wherein obtaining a value based on the assay includes quantitating the amount of the marker or the amount of activity of the marker in the sample.

12. The method of embodiment 9, wherein the value is a score.

13. The method of embodiment 12 wherein the score is a weighted score.

14. The method of embodiment 9, wherein the reference level is from a subject known not to have cystic fibrosis.

15. The method of embodiment 9, including assaying the sample for four or more markers selected from the CF biomarkers listed in Table 2, Table 3, Table 4, or Table 5.

16. The method of embodiment 9, including assaying the sample for: 4FO8, GEM_5327, narX, GEM_5047, DANJC10, and PS113-4947; or GEM_1794, APZ15_34865, HLA-DR, TXNL1, MT-ND1, VL15_07170, 135,2059, and fabG.

17. The method of embodiment 9, including assaying the sample for the presence or quantity of: BamMC406_2945, HLA-DRA, 4FO8, narX, and fabG or protein(s) that bind thereto; DNAJC10, PA4503, HLA-DRA, CLD-9, and TXNL1 or protein(s) that bind thereto; or PA4503, TMSB4X, FabG, WL94_35745, and barA_4 or protein(s) that bind thereto.

18. The method of embodiment 9, wherein diagnosing the subject as having CF includes one or more of determining the subject has a risk of CF-related fatigue, has exacerbation of CF, has or is prone to CF-related infection, or has increased disease severity.

19. An array or a microarray including: at least two different proteins, each of which binds one of 4FO8, GEM_5327, narX, GEM_5047, DANJC10, PS113-4947, GEM_1794, APZ15_34865, HLA-DR, TXNL1, MT-ND1, VL15_07170, 135,2059, or fabG; at least two different proteins, each of which binds one of 4FO8, GEM_5327, narX, GEM_5047, DANJC10, or PS113-4947; at least two different proteins, each of which binds one of GEM_1794, APZ15_34865, HLA-DR, TXNL1, MT-ND1, VL15_07170, 135,2059, or fabG; at least two different proteins, each of which binds one of the CF biomarkers listed in Table 3 or Table 5; at least five different proteins, each of which binds one of the CF biomarkers listed as part of a set of five in Table 4; two or more of the amino acid sequences shown in SEQ ID NO: 1-27 or a fragment thereof at least 6 amino acids in length; two or more of the peptides shown in Table 2 or Table 5; at least two different nucleic acids, each of which binds to a gene encoding one of the CF biomarkers listed in Table 3 or Table 5; at least two different nucleic acids, each of which binds to a gene encoding one of 4FO8, GEM_5327, narX, GEM_5047, DANJC10, or PS113-4947; at least two different nucleic acids, each of which binds to a gene encoding one of GEM_1794, APZ15_34865, HLA-DR, TXNL1, MT-ND1, VL15_07170, 135,2059, or fabG; or at least five different nucleic acids, each of which binds to a gene encoding one of the CF biomarkers listed as part of a set of five in Table 4.

20. The array or microarray of embodiment 19, including: proteins that bind to each of BamMC406_2945, HLA-DRA, 4FO8, narX, and fabG; proteins that bind to each of DNAJC10, PA4503, HLA-DRA, CLD-9, and TXNL1; proteins that bind to each of PA4503, TMSB4X, FabG, WL94_35745, and barA_4; proteins that bind to each of the sequences that mimotopes in Table 3 mimic; proteins that bind to each of the sequences shown in SEQ ID NO: 1-27; or proteins that bind to each of SEQ ID NOs: 7, 9, 6, 2, 11, 13, 3, 1, 8, 20, 5, 4, 10, and 16.

Example 1. Detection of Cystic Fibrosis Serological Biomarkers Using a T7 Phage Display Library This Example describes the identification and characterization of markers of cystic fibrosis. At least some of the material described in this Example was also published as Talwar et al., *Scientific Reports* 7:17745, 2017 (DOI: 10.1038/s41598-017-18041-2).

Cystic fibrosis (CF) is an autosomal recessive disorder affecting the cystic fibrosis transmembrane conductance regulator (CFTR). CF is characterized by repeated lung infections leading to respiratory failure. Using a high-throughput method, we developed a T7 phage display cDNA library derived from mRNA isolated from bronchoalveolar lavage (BAL) cells and leukocytes of sarcoidosis patients. This library was biopanned to obtain 1070 potential antigens. A microarray platform was constructed and immunoscreened with sera from healthy (n=49), lung cancer (LC) (n=31) and CF (n=31) subjects. 1,000 naïve Bayes models were built on the training sets. The top 20 frequently significant clones ranked with student t-test discriminating CF antigens from healthy controls and LC at a False Discovery Rate (FDR)<0.01 were selected. The performances of the models were validated on an independent validation set. The mean of the area under the receiver operating characteristic (ROC) curve for the classifiers was 0.973 with a sensitivity of 0.999 and specificity of 0.959. Finally, CF specific clones were identified that correlate highly with sweat chloride test, BMI, and FEV1% predicted values.

For the first time, this work shows that CF-specific serological biomarkers can be identified through immunocreenings of a T7 phage display library with high accuracy, which may have utility in development of molecular therapy.

Materials and Methods.

Chemicals. All chemicals were purchased from Sigma-Aldrich (St. Louis, MO) unless specified otherwise. LeukoLOCK filters and RNAlater were purchased from Life Technologies (Grand Island, NY). The RNeasy Midi kit was obtained from Qiagen, (Valencia, CA). The T7 mouse monoclonal antibody was purchased from Novagen (San Diego, CA). Alexa Fluor 647 goat anti-human IgG and Alex Fluor goat anti-mouse IgG antibodies were purchased from Life Technologies (Grand Island, NY).

Patient Selection. This study was approved by the institutional review board at Wayne State University, the Detroit Medical Center and Cystic Fibrosis Center. Sera was collected from three groups: 1) healthy volunteers; 2) confirmed CF subjects, and 3) subjects with adenocarcinoma of the lungs. All study subjects signed a written informed consent. All methods were performed in accordance with the human investigation guidelines and regulations by the IRB (Protocol Number=055208MP4E) at Wayne State University.

Pulmonary function tests were performed following ATS guidelines in a licensed laboratory in all patients unless contraindicated (Raghu et al., *Am J Respir Crit Care Med.* 183:788-824, 2011). All spirometric studies were performed using a calibrated pneumotachograph and lung volumes were measured in a whole-body plethysmograph (Jaeger Spirometry and SensorMedics Vmax 22, VIASYS Respiratory Care, Inc; Yorba Linda, CA). All CF subjects were ambulatory patients. Sweat chloride test values were obtained from the medical records.

Serum Collection. Using standardized phlebotomy procedures blood samples were collected and stored at −80° C. (Talwar et al., *EBioMed.* 2:341-350, 2015).

Construction and Biopanning of T7 Phage Display cDNA Libraries. T7 phage display libraries from BAL, WBC, EL-1 and MRC5 were made to generate a complex sarcoid library (CSL; Talwar et al., *EBioMed.* 2:341-350, 2015). Differential biopanning for negative selection was performed using sera from healthy controls to remove the non-specific IgG, and sarcoidosis sera for positive enrichment (Talwar et al., *EBioMed.* 2:341-350, 2015).

Microarray Construction and Immunoscreening. Informative phage clones were randomly picked and amplified after four rounds of biopannings and their lysates were arrayed in quintuplicates onto nitrocellulose FAST slides (Grace Biolabs, OR) using the ProSys 5510TL robot (Cartesian Technologies, CA). The nitrocellulose slides were hybridized with sera and processed as described previously (Talwar et al., *EBioMed.* 2:341-350, 2015).

Sequencing of Phage cDNA Clones. Individual phage clones were PCR amplified using T7 phage forward primer 5' GTTCTATCCGCAACGTTATGG 3' (SEQ ID NO: 28) and reverse primer 5' GGAGGAAAGTCGTTTTTTGGGG 3' (SEQ ID NO: 29) and sequenced by Genwiz (South Plainfield, NJ), using T7 phage sequence primer TGCTAAGGACAACGTTATCGG (SEQ ID NO: 30).

Data Acquisition and Pre-Processing. Following the immunoreaction, the microarrays were scanned in an Axon Laboratories 4100 scanner (Palo Alto, CA) using 532 and 647 nm lasers to produce a red (Alexa Fluor 647) and green (Alexa Fluor 532) composite image. Cy5 (red dye) labeled antihuman antibody was used to detect IgGs in human serum that were reactive to peptide clones, and a Cy3 (green dye) labeled antibody was used to detect the phage capsid protein (Talwar et al., *EBioMed.* 2:341-350, 2015). Using the ImaGene 6.0 (Biodiscovery) image analysis software, the binding intensity of each peptide with IgGs in sera was expressed as log 2 (red/green) fluorescent intensities. These data were pre-processed using the limma package in the R language environment (Ritchie et al., *NAR* 43:e47, 2015; "R: A language and environment for statistical computing," R Foundation for Statistical Computing, Vienna, Austria, 2015) and normexp method was applied to correct the background (Ritchie et al., *Bioinformat.* 23:2700-2707, 2007). Within array normalization was performed using the LOESS method (Id.; Yang et al., *NAR* 30:e15, 2002). The scale method was applied to normalize between arrays (Id.). Intensity ratio of a clone in CF samples divided by the same clone intensity ratio from healthy control samples were calculated to determine the fold change of a clone.

Statistical Analyses. To detect frequently differentially expressed antigens for CF a two-tailed t-test was applied. To evaluate the significant CF antigens identified with t-test, principal component analysis (PCA), agglomerative hierarchal clustering (HC), heatmap, and naïve Bayes classifier were applied. To avoid the problem of over-fitting the classifiers, the CF and healthy controls samples were randomly split into: i) training, ii) test, and iii) validation sets. Out of the 31 CF samples, 21 samples were randomly assigned into training (10 samples) and test (11 samples) sets. 1000 times random processing were repeated to generate 1000 training and test sets. The remaining 10 CF samples were used as an independent validation set. The 1000 training and testing sets for the healthy controls were randomly selected from 33 out of 49 samples (16 training and 17 test set). Therefore, the number of samples for the validation set for healthy controls was 16 while 31 LC samples were randomly split into test (15 samples) and validation (16 samples) sets. For CF clones specific selection, a t-test between the 1000 CF training sets vs. 1000 healthy control-training sets was applied. To correct for multiple comparisons, the false discovery rate (FDR) algorithm was applied with a threshold of 0.01 FDR (Benjamini & Hochberg, *J Royal Stat Soc*. Series B:289-300, 1995). The frequency of each significant clone (FDR<0.01) across all 1000 runs was calculated and sorted based on their frequency of occurrence. The top 20 clones were considered highly significant CF clones. A naïve Bayes classifier was built on each of the 1000 training sets and tested the classifier model on the 1000 testing sets. Finally, the classifier model was validated on a complete independent validation set. The range of clones starts with the most frequent clone followed by adding one clone at a time. The models were constructed on training sets and the model was applied on testing sets, as well as validation set. Finally, correlation of biomarkers with body mass index (BMI) and % predicted forced expiratory volume (FEV1) of CF patients were determined. Combinations of 5 clones from the top set of markers were calculated. For each combination, the aggregated vector was calculated from the mean of 5 clones and Pearson correlation between the aggregated vector and BMI and FEV1% predicted was determined.

Demographics: The demographics of the study subjects are shown in Table 1.

TABLE 1

Demographics

| Characteristic | Control Subjects | CF Patients | Lung Cancer Patients |
|---|---|---|---|
| Age (Mean ± SEM) | 45.3 ± 11.5 | 31.7 ± 10.8 | 62.3 ± 11.9 |
| Gender, N (%) | | | |
| Male | 7 (14) | 20 (65) | |
| Female | 42 (86) | 11 (35) | 31 (100) |
| Race, N (%) | | | |
| African American | 1 (3) | 1 (3) | |
| Caucasian | 25 (81) | 30 (97) | 31 (100) |
| Other | 5 (16) | | |
| Smoker (>50 packs/yr.), N (%) | 15 (30) | NA | 6 (20) |
| BMI (Mean ± SEM) | 28 ± 3.6 | 22.76 ± 0.61 | 24 ± 4.6 |
| Sweat Chloride values (mM/L) | NA | 103.31 ± 13.5 | NA |
| PFT Values (Mean ± SEM) | | | |
| FEV1 (% predicted) | NA | 59.30 ± 4.90 | NA |
| FVC (% predicted) | NA | 75.27 ± 4.49 | NA |
| TLC (% predicted) | NA | 101.47 ± 2.42 | NA |
| DLCO (% predicted) | NA | 89.77 ± 3.90 | NA |
| Gene Mutation, | | | |
| *Homozygous (Double mutation at F508 del) | NA | 15 (48) | NA |
| **Heterozygous (Double mutation one with F508 del) | NA | 9 (29) | NA |
| ***Other (Double mutation with none at F508 del) | NA | 7 (23) | NA |
| Bacterial culture results | | | |
| *Pseudomonas* (mucoid & non-mucoid) | NA | 21 (67) | NA |
| *Staphylococcus aureus* | NA | 13 (42) | NA |
| *Aspergillus* | NA | 3 (1) | NA |
| Adenocarcinoma of Lung, N (%) | NA | NA | 31 (100) |

Age values are presented as means and variability in SD.

N = Number of patients and percent shown in parentheses

Results. Complex sarcoidosis library detects unique antigens in the CF sera. A panel of potential antigens was randomly selected from two highly enriched pools of T7 phage cDNA libraries through biopanning of the CSL library (Talwar et al., *EBioMed.* 2:341-350, 2015). A microarray platform was constructed and immunoscreened with 111 sera (49 healthy controls, 31 with CF and 31 with adenocarcinoma (LC) of the lungs). The demographics of the study subjects are shown in Table 1. Among the CF patients, 15 (48%) were genotyped as F508del homozygotes, 9 (29%) were heterozygotes for F508del, and 7 (23%) had various mutations such as G542X or 2789+5 GT0A/S489X and others (Table 1). Following immunoreaction, the microarray data were pre-processed and then analyzed. A student t-test was applied on 1,000 training sets (FDR<0.01) between CF vs. healthy controls samples. A total of 599 clones appeared significant at least once. The frequency of each significant clone was calculated and the top 20 clones were ranked according to their significance and frequency. Furthermore, an unsupervised PCA was performed for all 1070 clones with data from 111 study subject sera. As shown in FIG. 2A, several LC and healthy controls clustered together with the CF samples.

To investigate whether the identified 20 highly significant CF clones can improve class separation of CF samples from LC and healthy controls, a PCA plot using only those clones (FIG. 2C) was constructed. Using the 20 highly significant CF clones aided to a class separation of CF samples from LC and healthy controls. Forty nine percent of variance was explained along the PC1.

Figure 2B:
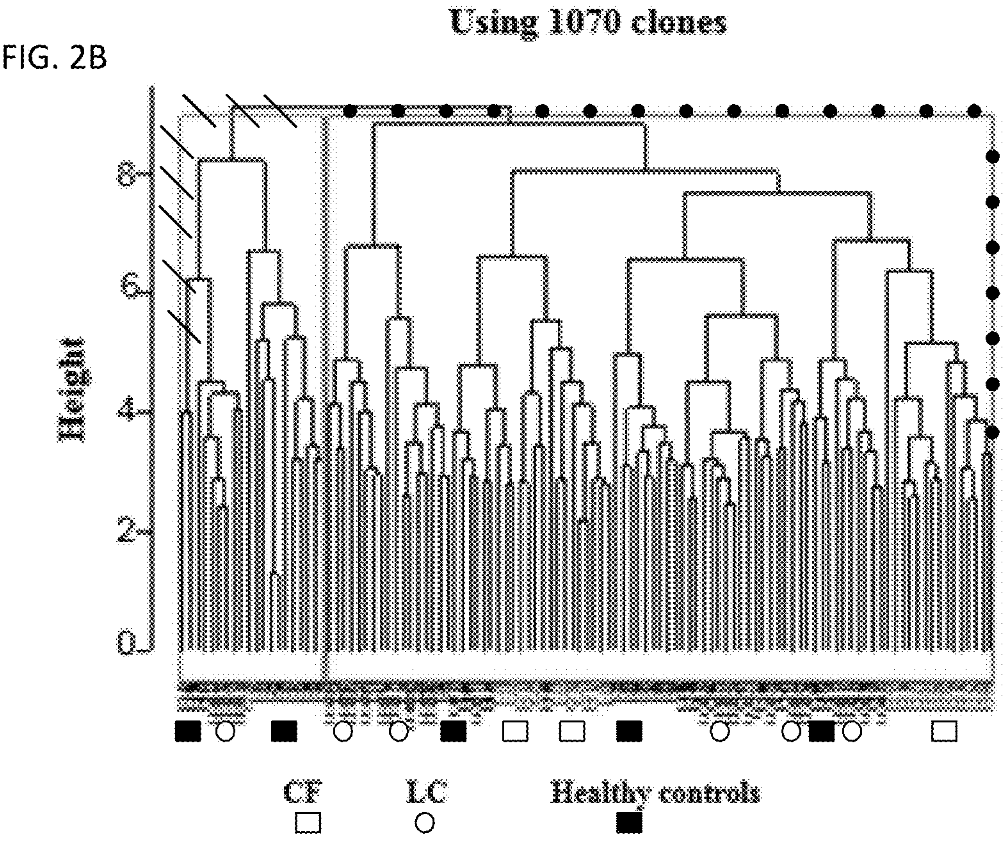
Figure 2C:
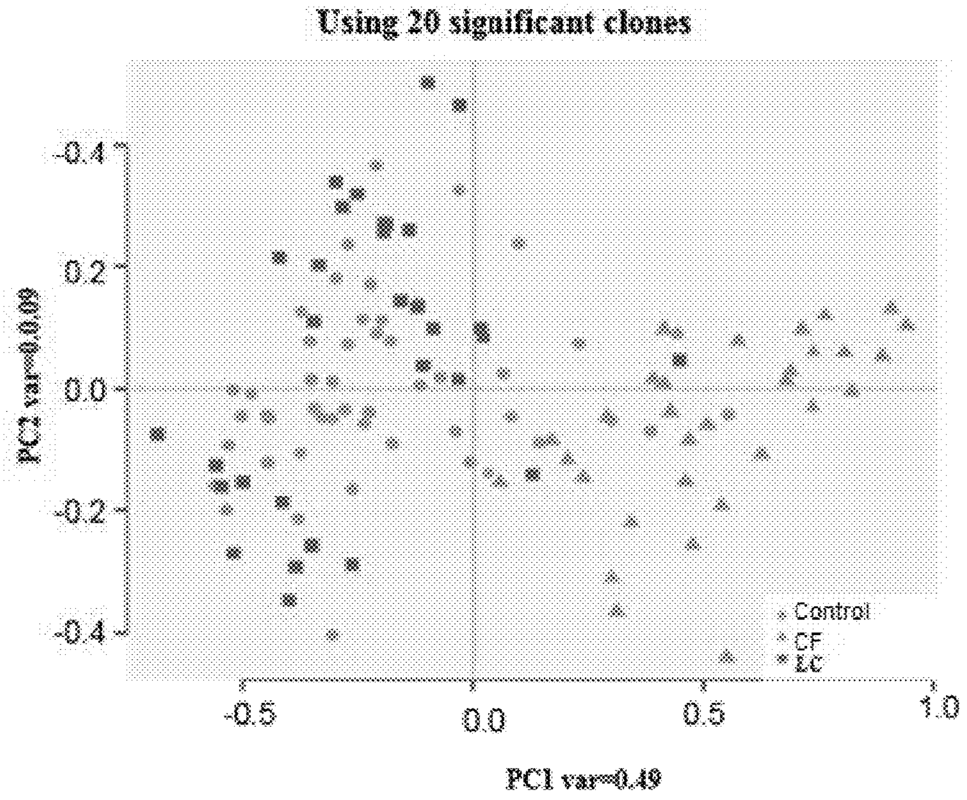
Figure 2D:
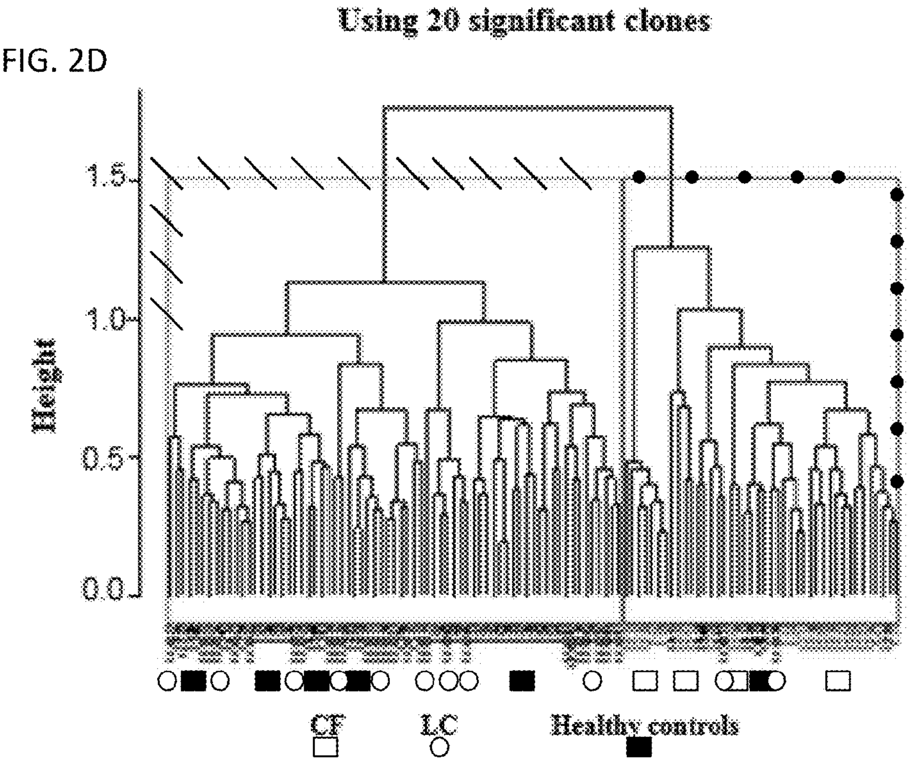
Figure 3:
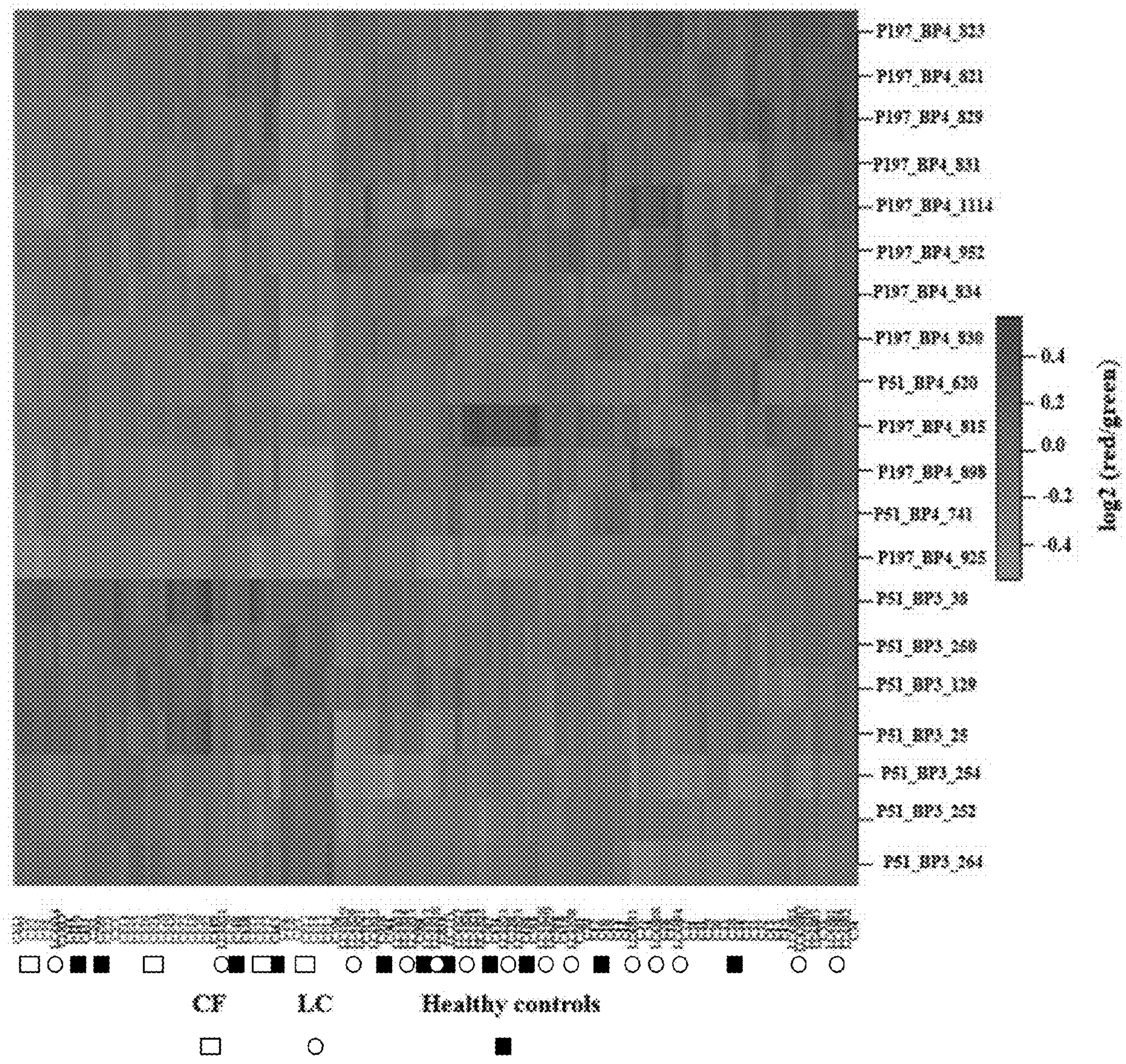
FIG. 3 is a heatmap generated based on the 20 highly significant CF clones from the data of 111 study subjects (49 healthy controls, 31 with CF and 31 with LC). Each row represents a clone, while each column represents a study subject.

Next, unsupervised hierarchical clustering was performed with all 1070 clones on 111 samples. It was observed that the magenta cluster (line with dots) has a mix of samples and lacks specific sub-clusters of CF samples (FIG. 2B). In contrast, when the clustering algorithm was performed using the 20 highly significant CF clones on all samples, a distinct hierarchical linkage, clearly demarcating CF samples from others (healthy controls and LC) was observed (FIG. 2D). Distinct expression features of 20 highly significant CF clones among study subjects are highlighted in a heatmap plot (FIG. 3).

Figure 4A:
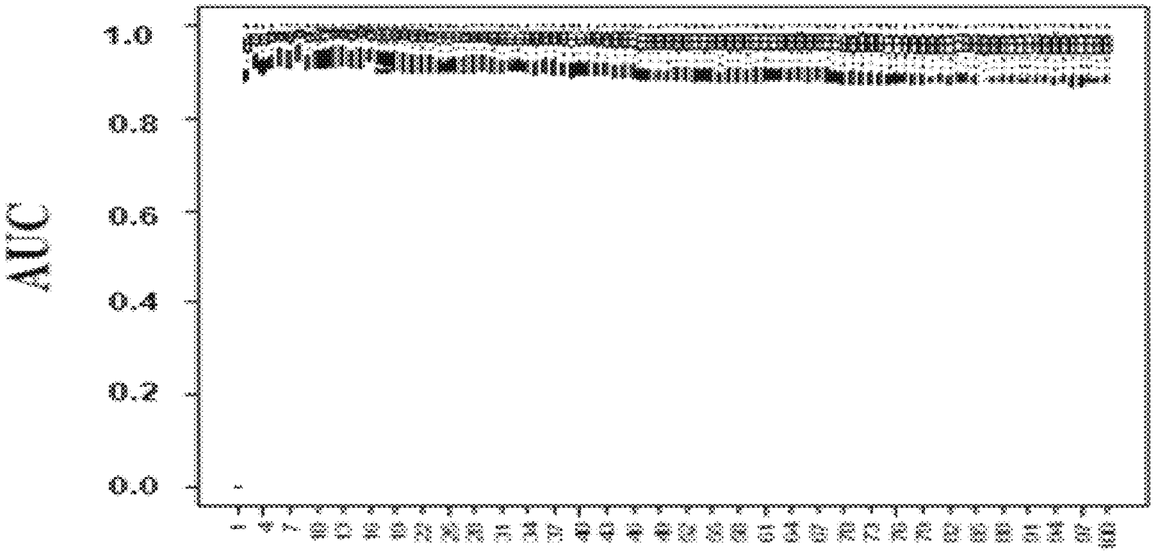
FIGS. 4A-4C illustrate classification performance of the naïve Bayes classifier. The classifier is to predict CF from LC and healthy control samples.
Figure 4B:
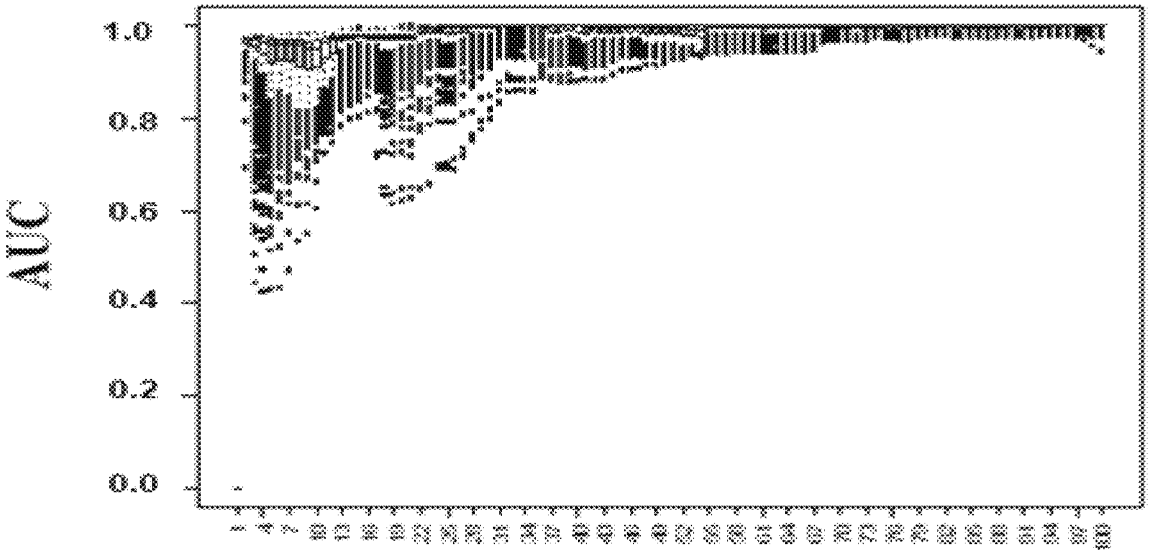
Figure 4C:
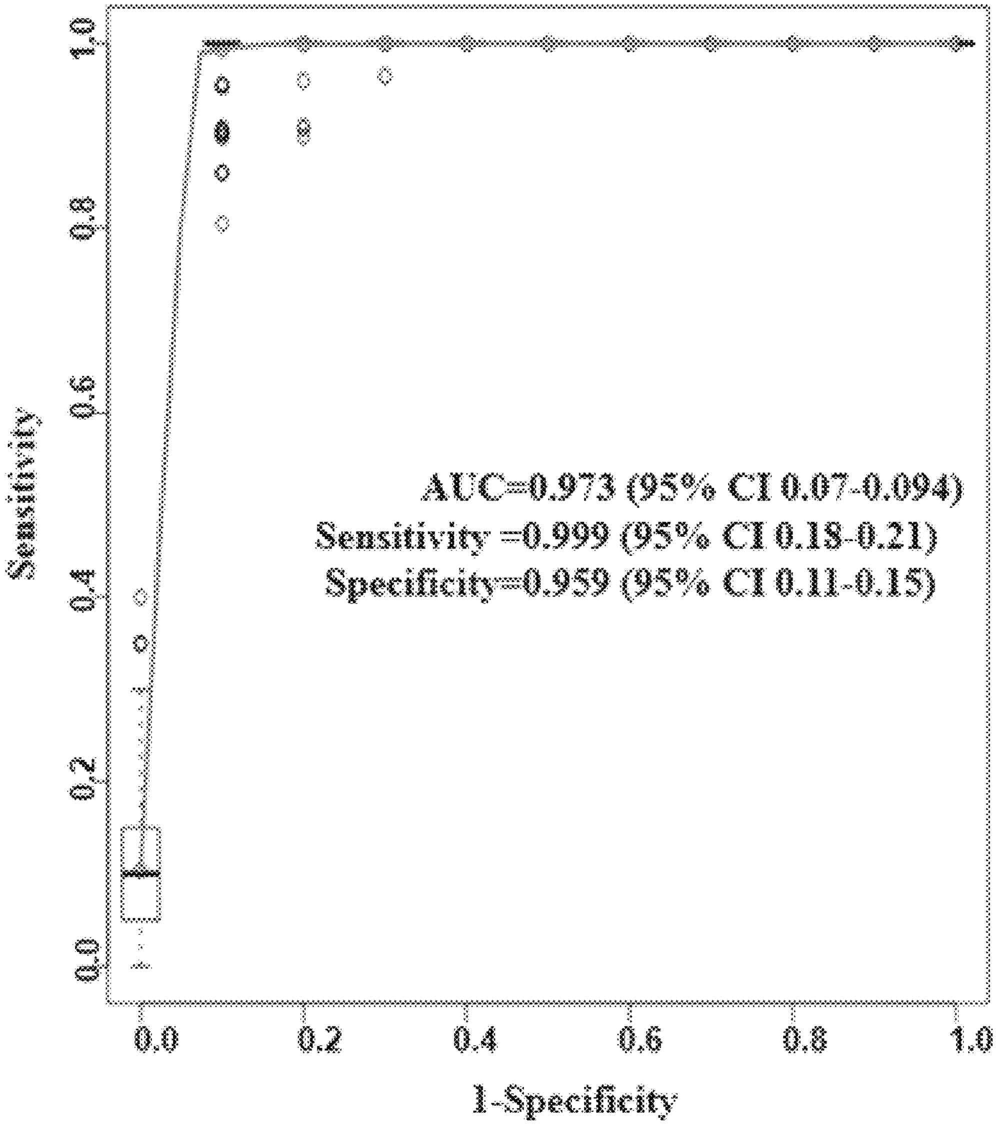

Next, the classifier model was applied and the AUC values on accumulating numbers of clones (see method section) were calculated on test and validation sets. FIG. 4A shows the AUC values for the test set. The lowest average AUC values for the test set was 0.956. FIG. 4B graphically represents the performance of the classifier model when applied to the validation set. When the classifier model was applied on the validation set, the lowest average AUC value was 0.926. These results clearly indicate that the classification model based on the accumulating number of significant clones when applied on the test and the validation sets have a very good classification performance. Finally, to assess if the identified highly significant CF clones provide a sound classification performance, the naïve Bayes classification algorithm was applied with the 20 highly significant CF clones to predict CF samples from healthy controls and LC samples. At the optimal threshold (highest true positivity with lowest false positivity for each of the 1000 runs), reliable prediction of CF from healthy controls and LC samples with a mean specificity of 0.959 (95% CI, 0.11-0.15) and a mean sensitivity of 0.999 (95% CI, 0.18-0.21) was achieved. The mean AUC under the ROC for the classifier was 0.973 (95% CI, 0.07-0.094) (FIG. 4C).

Characterization of Significant CF Clones. Based on the results of training and validation sets, the 20 highly performing clones (Table 3 and FIGS. 1A-1E) were characterized through sequencing, and clones that can predict sweat chloride tests, FEV1% predicted, and body mass index (BMI) were identified. After obtaining the sequences of clones, Expasy program was used to translate the cDNA sequences to protein sequences (Talwar et al., *EBioMed.* 2:341-350, 2015). Protein blast using algorithms of the BLAST program were applied to identify the highest homology to identified peptides. Additionally, these results were compared with corresponding nucleotide sequences using nucleotide blast and determined the predicted amino acid in frame with phage T7 10 B gene capsid proteins. Among the 20 high performing clones, four CF reactive antigens comprise relatively large peptides, while 16 CF reactive antigens are coded by the inserted gene fragments leading to out-of-frame-peptides, hereby meeting the definition of mimotopes (Wang et al., *NEJM* 353:1224-1235, 2005) (Table 2). As CF sera reacted to these out-of-frame-peptides, it is likely that these clones represent CF antigens that are produced as a result of altered reading frames or alternative splicing, as shown in previous studies (Id.; Lin et al., *Cancer Epidem Biomarkers Prev AACR* 16:2396-2405, 2007).

Figure 5A:
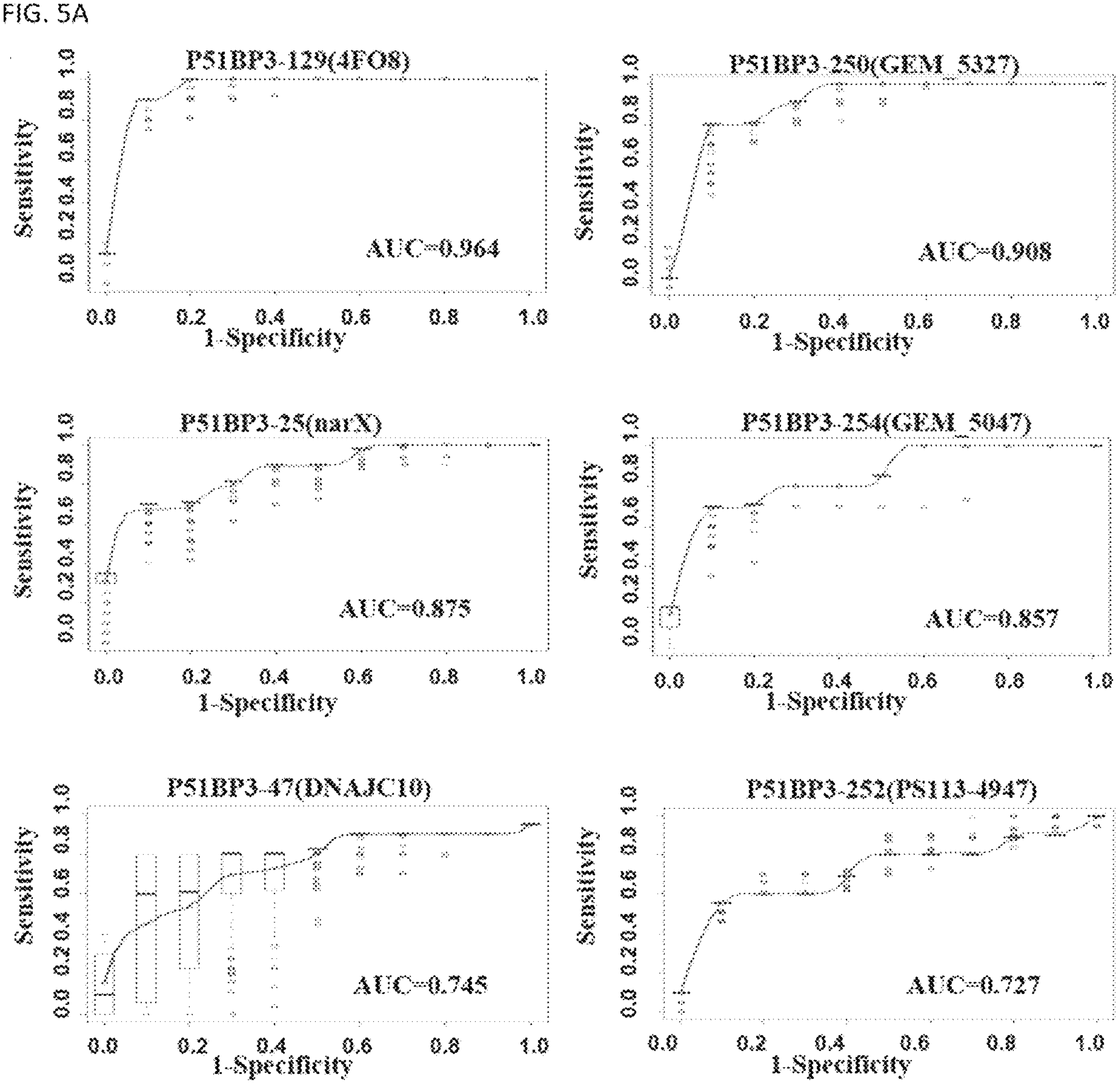
FIGS. 5A-5B show naïve Bayes classification performance for the top 14 clones.
Figure 5B:
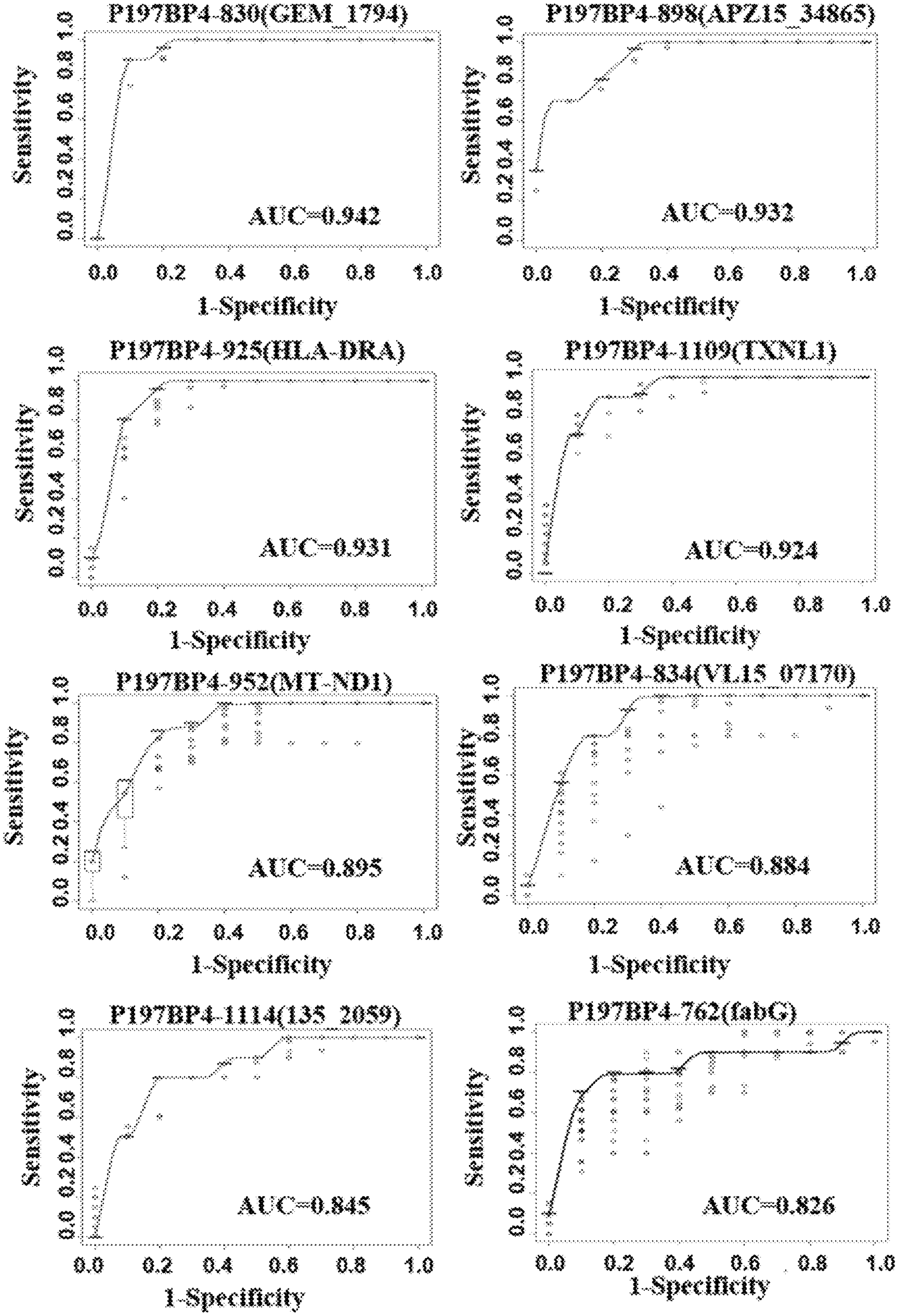

Full length of peptides and genes of the top 20 CF clones are shown in Table 3 and FIG. 2. Table 2 shows the 14 most significant CF antigens, gene names, sensitivity, specificity, and FDR adjusted p-value. FIGS. 5A and 5B show the ROC curves for these 14 CF antigens.

Figure 6A:
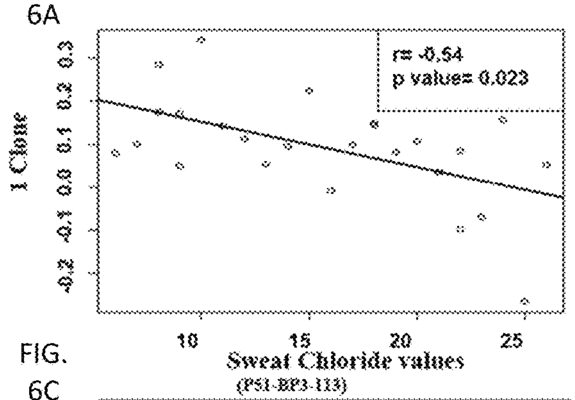
FIGS. 6A-6F show Pearson correlation of identified biomarkers with clinical values. Scatter plots depicted correlation of the sweat chloride values with one clone (FIG. 6A) and aggregated 5 clones (FIG. 6B). Scatter plots depicted the correlation for BMI predicted with one clone (FIG. 6C) and aggregated 5 clones (FIG. 6D). Scatter plots depicted correlation of FEV1% with one clone (FIG. 6E) and aggregated 5 clones (FIG. 6F). The correlation values and p values are shown in the top right of each plot. The names of the clones are shown at the bottom of each plot.
Figure 6B:
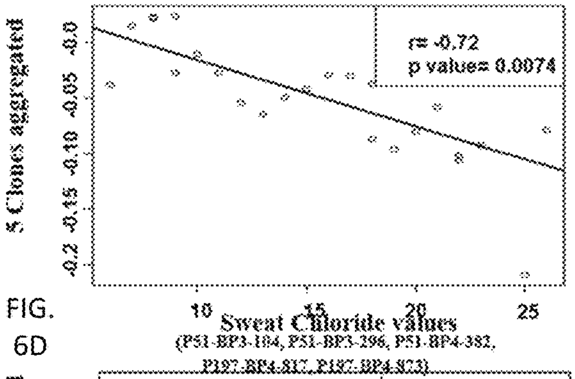

Finally, it was sought to determine whether any of the identified CF biomarkers correlate with sweat chloride test, BMI, and/or FEV1% predicted values. Sweat chloride test, PFT, and BMI values for CF subjects are shown in Table 1. Sweat chloride test is commonly used as screening tool for CF diagnosis (Gibson & Cooke, Pediatrics 23:545-549, 1959). The highest spearman correlation (r=−0.54) was found between sweat chloride values and the clone p51_BP3_113 (GEM_5047; SEQ ID NO: 2) (FIG. 6A). By combining this clone with four additional clones a higher correlation was reached (r=−0.72) (FIG. 6B).

Figure 6C:
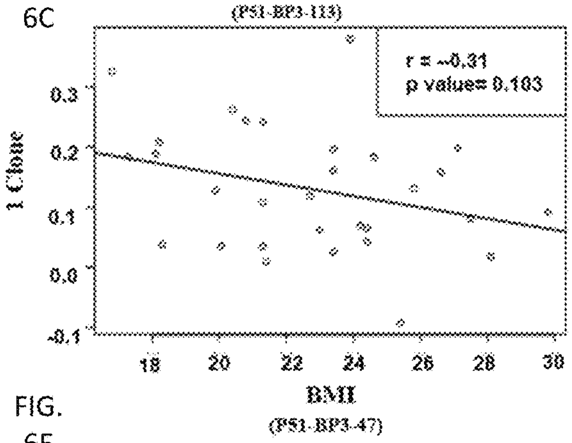
Figure 6D:
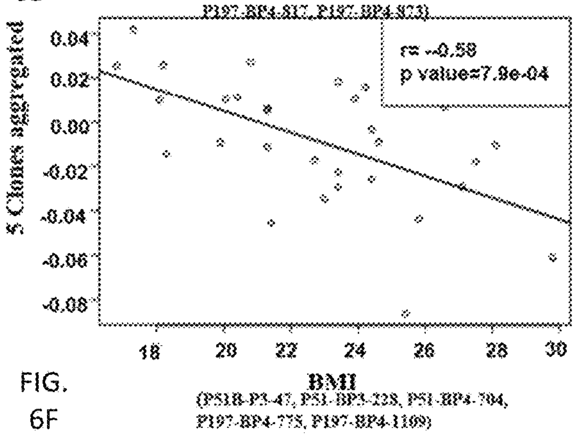
Figure 6E:
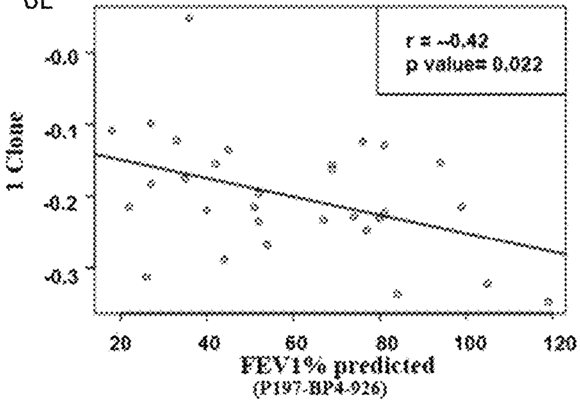
Figure 6F:
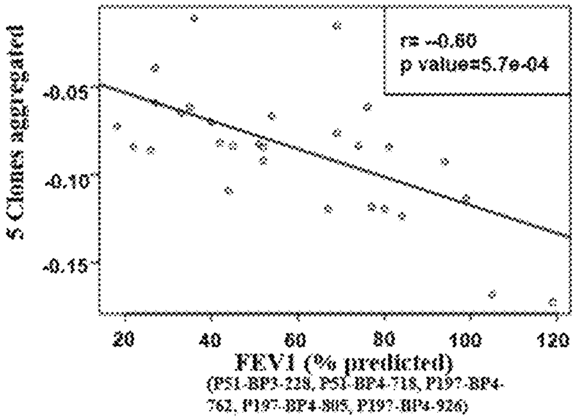
Figure 8:
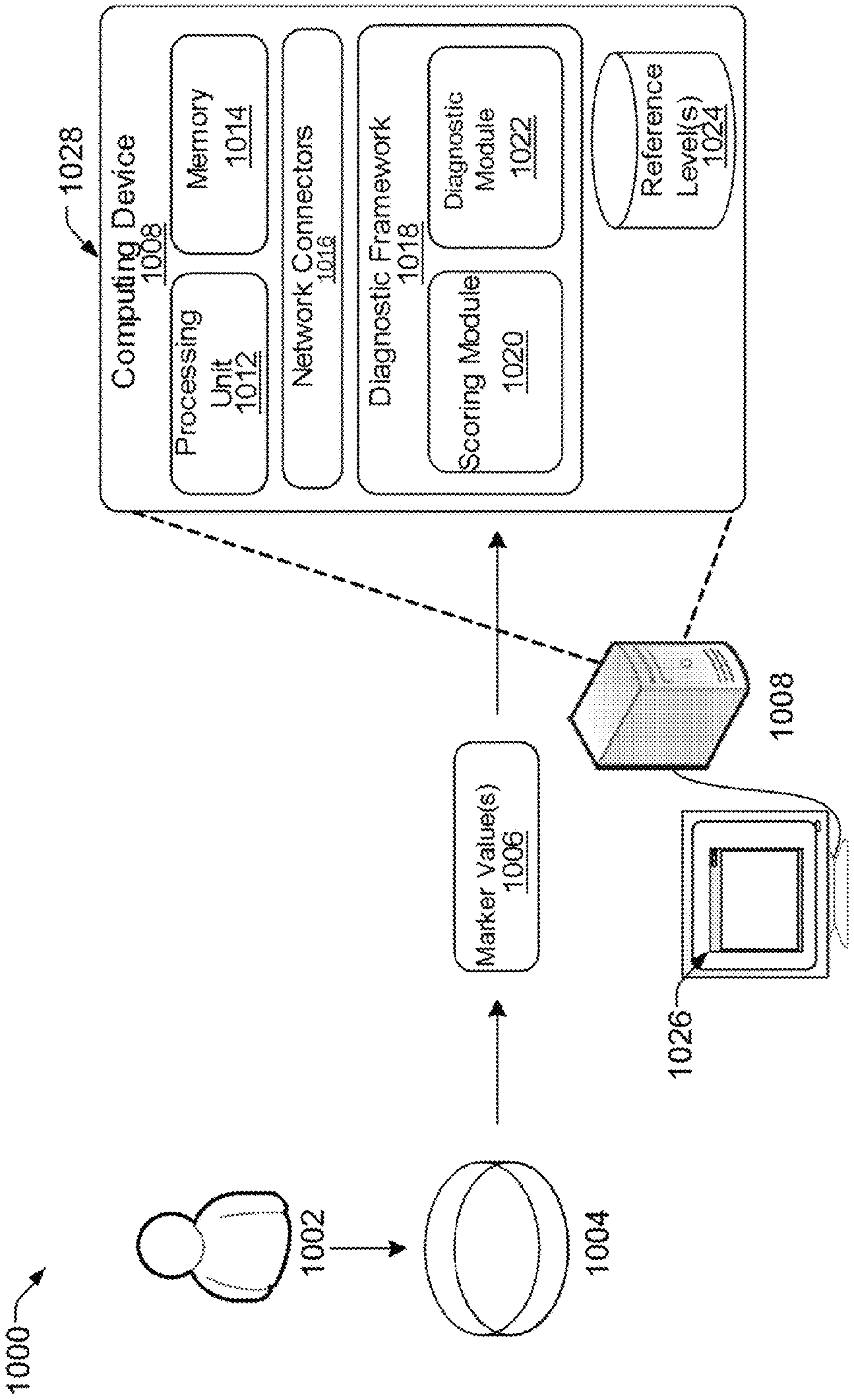
FIG. 8 shows an illustrative schematic for using computational tools as part of a process for diagnosing CF, including an illustrative diagram of a computing device implementing the diagnostic framework.

BMI is an important clinical measure among CF patients to predict exacerbation and decline of lung function testing (Sheikh et al., *Front Pediatrics* 2:33, doi:10.3389/fped.2014.0003, 2014). The highest spearman correlation (r=−0.31) was found between BMI and the P51_BP3_47 clone (dnaJ homolog; SEQ ID NO: 11) (FIG. 6C). By combining this clone with four other clones a higher correlation with BMI was reached (r=−0.58) (FIG. 6D). Additionally, the highest correlation (r=−0.42) between FEV1% predicted and clone P197_BP4_926 (FIG. 6E) was found. The correlation value (r=−0.6) improved once 4 other clones were added (FIG. 6F). Table 4 shows the correlation between sweat chloride values, BMI and FEV1% predicted values and significant clones. Seven out of 16 identified clones overlapped with highly specific and sensitive CF clones shown in Table 2. In addition, six other clones with significant correlation with sweat chloride test, BMI and FEV1% predicted values were identified. Similar results were observed when other PFT values including FVC were plotted.

Summary. Cystic fibrosis (CF) is an autosomal recessive disorder affecting the CF transmembrane conductance regulator (CFTR). CF is characterized by repeated lung infections leading to respiratory failure. Using a high-throughput method, a T7 phage display cDNA library derived from mRNA isolated from bronchoalveolar lavage (BAL) cells and leukocytes of sarcoidosis patients was previously developed. This library was biopanned to obtain 1070 potential antigens. A microarray platform was constructed and immunoscreened with sera from healthy (n=49), lung cancer (LC) (n=31) and CF (n=31) subjects. 1,000 naïve Bayes models were built on the training sets. The top 20 frequently significant clones were selected and ranked with student t-test discriminating CF antigens from healthy controls and LC at a False Discovery Rate (FDR)<0.01. The performances of the models were validated on an independent validation set. The mean of the area under the receiver operating characteristic (ROC) curve for the classifiers was 0.973 with a sensitivity of 0.999 and specificity of 0.959. Finally, CF specific clones that correlate highly with sweat chloride test, BMI, and FEV1% predicted values were identified. For the first time, it has been shown that CF specific serological biomarkers can be identified through immunocreenings of a T7 phage display library with high accuracy, which may have utility in development of molecular therapy.

TABLE 2

Significant cystic fibrosis clones.

| Clone | Increased in Cystic Fibrosis vs Healthy Controls | NCBI Protein Number | p value | FDR corrected p Value | AUC 95% CI | Sensitivity, 95% CI | Specificity, 95% CI |
|---|---|---|---|---|---|---|---|
| P51_BP3_129 (SEQ ID NO: 7) | Chain A *Pseudomonas Aeruginosa* Metap, In Mn Form | 4FO8 \|4FO7\|A | 0.0069 | 0.032 | 0.964 (0.04-0.10) | 0.90 (0.21-0.26) | 0.97 (0.08-0.14) |
| P51_BP3_250 (SEQ ID NO: 9) | Beta-lactamase | GEM_5327 \|AFQ51711.1\| | 0.0125 | 0.033 | 0.908 (0.08-0.14) | 0.80 (0.20-0.26) | 0.93 (0.10-0.17) |
| P51_BP3_25 (SEQ ID NO: 6) | Histidine kinase | narX gb\|KJS26770.1 | 0.0017 | 0.031 | 0.875 (0.12-0.19) | 0.71 (0.22-0.30) | 0.95 (0.08-0.17) |
| P51_BP3_254 (SEQ ID NO: 2) | Outer membrane Porin | GEM_5047 \|WP_060349386.1\| | 0.0056 | 0.022 | 0.857 (0.14-0.20) | 0.71 (0.26-0.29) | 0.93 (0.10-0.16) |
| P51_BP3_47 (SEQ ID NO: 11) | dnaJ homolog | DNAJC10 NP_071760.2 | 0.0006 | 0.050 | 0.745 (0.08-0.14) | 0.82 (0.20-0.21) | 0.74 (0.08-0.14) |
| P51_BP3_252 (SEQ ID NO: 13) | γ-glutamyltrans-peptidase | PS113-4947 \|WP_042609239.1\| | 0.0005 | 0.030 | 0.727 (0.06-0.11) | 0.61 (0.12-0.14) | 0.90 (0.11-0.15) |

| Clone | Decreased in Cystic Fibrosis vs Healthy Controls | NCBI Protein Number | p value | FDR corrected p Value | AUC 95% CI | Sensitivity, 95% CI | Specificity, 95% CI |
|---|---|---|---|---|---|---|---|
| P197_BP4_830 (SEQ ID NO: 3) | TetR family transcriptional regulator | GEM_1794 \|WP_043185598.1\| | 3.44E−05 | 0.032 | 0.942 (0.06-0.09) | 0.90 (0.21-0.22) | 0.94 (0.10-0.12) |
| P197_BP4_898 (SEQ ID NO: 1) | AraC-family transcriptional regulator | APZ15_34865 \|WP_059486090.1\| | 0.0001 | 0.019 | 0.932 (0.07-0.09) | 0.99 (0.20-0.26) | 0.71 (0.08-0.16) |
| P197_BP4_925 (SEQ ID NO: 8) | HLA-DR alpha | HLA-DR \|AAO23887.1\| | 0.0076 | 0.037 | 0.931 (0.07-0.11) | 0.99 (0.20-0.26) | 0.81 (0.10-0.15) |
| P197_BP4_1109 (SEQ ID NO: 20) | Thioredoxin like protein | TXNL1 CAA09375.1 | 0.001 | 0.045 | 0.924 (0.05-0.11) | 0.89 (0.18-0.20) | 0.87 (0.10-0.13) |
| P197_BP4_952 (SEQ ID NO: 5) | NADH dehydro-genase subunit 1 | MT-ND1 \|AFA28546.1\| | 0.0007 | 0.030 | 0.895 (0.08-0.20) | 0.91 (0.20-0.29) | 0.78 (0.15-0.18) |
| P197_BP4_834 (SEQ ID NO: 4) | AMP-dependent synthetase | VL15_07170 \|WP_048244810.1\| | 0.0036 | 0.034 | 0.884 (0.10-0.20) | 0.99 (0.20-0.26) | 0.71 (0.13-0.18) |
| P197_BP4_1114 (SEQ ID NO: 10) | Peptide ABC transporter substrate binding protein | 135_2059 \|ALB12327.1\| | 0.0011 | 0.050 | 0.845 (0.13-0.17) | 0.80 (0.26-0.26) | 0.84 (0.14-0.16) |
| P197_BP4_762 (SEQ ID NO: 16) | Ketoacyl-ACP reductase | fabG WP_034004244.1 | 0.0011 | 0.050 | 0.826 (0.09-0.14) | 0.79 (0.12-0.14) | 0.87 (0.11-0.17) |

TABLE 3

Full length sequence analysis of top 20 CF phage clones using NCBI BLAST (see FIG. 1 for corresponding alignments). Duplicate clones are listed in the second column.

| Rank | Clone(s) (Peptide Size) | Peptide Sequences of mimotopes in-frame with T7 10B gene | Description of the sequences that mimotope(s) mimic (w/NCBI Seq ID) |
|---|---|---|---|
| 1 | P51_BP3_25 (15 aa) P197_BP4_817 | LPRIFIELAQHQARV (SEQ ID NO: 6) | histidine kinase [*Pseudomonas* sp. BRH_c35] Sequence ID: gb\|KJS26770.1\| |
| 2 | P51_BP3_47 (134 aa) | SAKYKETRLKEKEDALTRTELET LQKQKKVKKPKPEFPVYTPLET TYIQSYDHGTSIEEIEEQMDDWL ENRNRTQKKQAPEWTEEDLSQ LTRSMVKFPGGTPGRWEKIAHE LGRSVTDVTTKAKLAAALE (SEQ ID NO: 11) | dnaJ homolog subfamily C member 1 precursor [*Homo sapiens*] Sequence ID: NP_071760.2 |
| 3 | P51_BP3_104 (20 aa) | PYVGMVATTSPPSPPPAVTT (SEQ ID NO: 14) | Lytic transglucosylase [*Burkholderia cepacia*] Sequence ID: ref\|WP_059730606.1\| |
| 4 | P51_BP3_129 (16 aa) P51_BP4_382 | AGISRELVDKLAAALE (SEQ ID NO: 7) | Chain A, *Pseudomonas aeruginosa* Metap, In Mn Form Sequence ID: pdb\|4F07\|A |

TABLE 3-continued

Full length sequence analysis of top 20 CF phage clones using NCBI BLAST (see FIG. 1 for corresponding alignments). Duplicate clones are listed in the second column.

| Rank | Clone(s) (Peptide Size) | Peptide Sequences of mimotopes in-frame with T7 10B gene | Description of the sequences that mimotope(s) mimic (w/NCBI Seq ID) |
|---|---|---|---|
| 5 | P51_BP3_228 (23 aa) | RDPQCWRWDLVRGVWVTGTD PSW (SEQ ID NO: 12) | ABC transporter permease [*Pseudomonas aeruginosa*] Sequence ID: ref\|WP_033938298.1\| |
| 6 | P51_BP3_250 (16 aa) | SRNCVNTWVFLNLMQD (SEQ ID NO: 9) | Beta-lactamase [*Burkholderia cepacia* GG4] Sequence ID: gb\|AFQ51711.1\| |
| 7 | P51_BP3_252 (29 aa) | RDTGNSIFLSNGRRYALKFGWD TQFSFIF (SEQ ID NO: 13) | gamma-glutamyltranspeptidase [*Pseudomonas fluorescens*] Sequence ID: ref\|WP_042609239.1\| |
| 8 | P51_BP3_254 (18 aa) P51_BP3_113 | GKYNSTFTSSIIHNKNMK (SEQ ID NO: 2) | Outer membrane porin [*Burkholderia cepacia*] Sequence ID: ref\|WP_060349386.1\| |
| 9 | P51_BP4_718 (66 aa) | VATAQTRLRSYSCASLRFSSAT MSDKPDMAEIEKFDKSKLKKTE TQEKNPLPSKETIEQEKQAGES (SEQ ID NO: 15) | TMSB4X protein, partial [*Homo sapiens*] Sequence ID: gb\|AAH61586.1\| |
| 10 | P197_BP4_762 (9 aa) P197_BP4_873 | IQHQHLGQI (SEQ ID NO: 16) | beta-ketoacyl-ACP reductase [*Pseudomonas aeruginosa*] Sequence ID: WP_034004244.1 |
| 11 | P197_BP4_775 (27 aa) | VDKSVLLSLGRKKYGAVGSLSQ STGGH (SEQ ID NO: 17) | conjugal transfer protein [*Pseudomonas aeruginosa*] Sequence ID: WP_044265747.1 |
| 12 | P197_BP4_805 (19 aa) | SLGAMVCLHSVPSHKATWI (SEQ ID NO: 18) | hemolysin D [*Burkholderia cepacia*] Sequence ID: ref\|WP_060377052.1\| |
| 13 | P197_BP4_830 (8 aa) | YMCFSLPP (SEQ ID NO: 3) | TetR family transcriptional regulator [*Burkholderia cepacia*] Sequence ID: ref\|WP_043185598.1\| |
| 14 | P197_BP4_834 (34 aa) | GITSARLGTGTGERLRSGCVQG LVGMGRPVDRAC (SEQ ID NO: 4) | AMP-dependent synthetase [*Burkholderia cepacia*] Sequence ID: ref\|WP_048244810.1\| |
| 15 | P197_BP4_898 (17 aa) | DLSSEVATHQPIIACLP (SEQ ID NO: 1) | AraC family transcriptional regulator [*Burkholderia cepacia*] Sequence ID: ref\|WP_059486090.1\| |
| 16 | P197_BP4_925 (49 aa) P51_BP4_704 P51_BP3_296 | DAPSPLPETTENVVCALGLTVG LVGIIIGTIFIIKGVRKSNAAERRG PL (SEQ ID NO: 8) | HLA-DR alpha [*Homo sapiens*] Sequence ID: gb\|AAO23887.1\|AF481359_1 |
| 17 | P197_BP4_926 (16 aa) | VTLMRQRVMMMGRHTT (SEQ ID NO: 19) | Signal transduction histidine-protein kinase/phosphatase [*Pseudomonas aeruginosa*] Sequence ID: emb\|CRQ82296.1\| |
| 18 | P197_BP4_952 (12 aa) | SATSSLAVYSIL (SEQ ID NO: 5) | NADH dehydrogenase subunit 1 (mitochondrion) [*Homo sapiens*] Sequence ID: gb\|AFA28546.1\| |
| 19 | P197_BP4_1109 (213 aa) | KIDRLDGAHAPELTKKVQRHAS SGSFLPSANEHLKEDLNLRLKK LTHAAPCMLFMKGTPQEPRCG FSKQMVEILHKHNIQFSSFDIFS DEEVRQGLKAYSSWPTYPQLY | Thioredoxin-like protein [*Homo sapiens*] Sequence ID: emb\|CAA09375.1\| |

TABLE 3-continued

Full length sequence analysis of top 20 CF phage clones using NCBI BLAST (see FIG. 1 for corresponding alignments). Duplicate clones are listed in the second column.

| Rank | Clone(s) (Peptide Size) | Peptide Sequences of mimotopes in-frame with T7 10B gene | Description of the sequences that mimotope(s) mimic (w/NCBI Seq ID) |
|---|---|---|---|
| | | VSGELIGGLDIIKELEASEELDTI CPKAPKLEERLKVLTNKASVML FMKGNKQEAKCGFSKQILEILN STGVEYETFDILEDEEVRQGLK AYSNWPSLRPHSSN (SEQ ID NO: 20) | |
| 20 | P197_BP4_1114 (29 aa) | LRPPNNPPPNTNYLTPTPHNHG KPTPLIQ (SEQ ID NO: 10) | peptide ABC transporter substrate-binding protein [*Burkholderia cepacia* complex] Sequence ID: gb\|ALB12327.1\| |

TABLE 4

Correlation of biomarkers with Sweat Chloride test, BMI and FEV1% predicted.

| Clinical measure | Single clone | Corr'nr | Set of five clones | Gene name | p value | Corr'nr |
|---|---|---|---|---|---|---|
| Sweat Chloride values | P51_BP3_113 (p value 0.002, Gene Name: GEM_5047) | −0.54 | P51_BP3_104 (SEQ ID NO: 14) | BamMC406_2945 | 0.009 | −0.72 |
| | | | P51_BP3_296 (SEQ ID NO: 8) | HLA-DRA | 0.024 | |
| | | | P51_BP4_382 (SEQ ID NO: 7) | 4FO8 | 0.017 | |
| | | | P197_BP4_817 (SEQ ID NO: 6) | narX | 0.00015 | |
| | | | P197_BP4_873 (SEQ ID NO: 16) | fabG | 0.009 | |
| BMI | P51_BP3_47 | −0.31 | P51_BP3_47 (SEQ ID NO: 11) | DNAJC10 | 0.0006 | −0.58 |
| | | | P51_BP3_228 (SEQ ID NO: 12) | PA4503 | 0.0022 | |
| | | | P51_BP4_704 (SEQ ID NO: 8) | HLA-DRA | 0.004 | |
| | | | P197_BP4_775 (SEQ ID NO: 17) | CL-9 | 0.014 | |
| | | | P197_BP4_1109 (SEQ ID NO: 20) | TXNL1 | 0.001 | |
| FEV1 (% Predicted) | P197_BP4_926 | −0.42 | P51_BP3_228 (SEQ ID NO: 12) | PA4503 | 0.0022 | −0.60 |
| | | | P197_BP4_718 (SEQ ID NO: 15) | TMSB4X | 0.007 | |
| | | | P197_BP4_762 (SEQ ID NO: 16) | fab G | 0.0011 | |
| | | | P197_BP4_805 (SEQ ID NO: 18) | WL94_35745 | 0.001 | |
| | | | P197_BP4_926 (SEQ ID NO: 19) | barA_4 | 0.015 | |

Example 2: Characterization of Additional CF Clones

This example describes the selection of additional clones that were identified in the same screen described in Example 1.

Additional clones (having the next most frequent significance after the 20 described above) were selected from the library described in Example 1. These clones are listed in Table 5 and further illustrated in FIG. 7.

TABLE 5

Full length sequence analysis of additional CF phage clones using NCBI BLAST (see also FIG. 7 for corresponding alignments).

| Rank | Clone (Peptide Size) | Peptide Sequences of mimotopes in-frame with T7 10B gene | Description of the sequences that mimotopes mimic |
|---|---|---|---|
| 21 | P51_BP3_34 (25 aa) | SGSLEVRSCTPAWVTERNFI SKKKG (SEQ ID NO: 21) | transposase [*Pseudomonas aeruginosa*] Sequence ID: ref\|WP_033987775.1\| |
| 22 | P51_BP3_37 (18 aa) | GKYNSTFTSSIIHNKNMK (SEQ ID NO: 22) | alkaline phosphatase [*Pseudomonas aeruginosa*] Sequence ID: ref\|WP_033973119.1\| |
| 23 | P51_BP3_44 (24 aa) | SISPFTVTKHKPTSQGLEYLH AFA (SEQ ID NO: 23) | DNA methyltransferase [*Campylobacter jejuni*] Sequence ID: ref\|WP_052797960.1\| |
| 24 | P51_BP3_378 (87 aa) | PVEGRGRPSPLHVAQHSYT GVEAQPLNHQVLHVAGRDG LPVAVNGTLSDDDDVQSGPT APSLTQPLTHEVLPAVLGWS LGDEQPVGP (SEQ ID NO: 24) | 3-oxoadipate--succinyl-CoA transferase [*Pseudomonas aeruginosa*] Sequence ID: ref\|WP_034052824.1\| |
| 25 | P51_BP4_382 (14 aa) | SRMARSSWRRTSAA (SEQ ID NO: 25) | glycosyl hydrolase [*Streptomyces* sp. NRRL B-24720] Sequence ID: ref\|WP_030919145.1\| |
| 26 | P51_BP4_741 (29 aa) | SATCSLFAALTVPDACPRTR PLRNSSFET (SEQ ID NO: 26) | AraC family transcriptional regulator [*Pseudomonas aeruginosa*] Sequence ID: ref\|WP_042166025.1\| |
| 27 | P197_BP4_967 (5 aa) | SVRRG (SEQ ID NO: 27) | peptidase S1 [*Pseudomonas aeruginosa*] Sequence ID: ref\|WP_020750534.1\| |

As will be understood by one of ordinary skill in the art, each embodiment disclosed herein can comprise, consist essentially of or consist of its particular stated element, step, ingredient or component. Thus, the terms “include” or “including” should be interpreted to recite: “comprise, consist of, or consist essentially of.” The transition term “comprise” or “comprises” means includes, but is not limited to, and allows for the inclusion of unspecified elements, steps, ingredients, or components, even in major amounts. The transitional phrase “consisting of” excludes any element, step, ingredient or component not specified. The transition phrase “consisting essentially of” limits the scope of the embodiment to the specified elements, steps, ingredients or components and to those that do not materially affect the embodiment. A material effect would cause a statistically significant reduction in the ability to identify CF patients (as compared to healthy controls and lung cancer patients) using the serum markers disclosed herein.

Unless otherwise indicated, all numbers expressing quantities of ingredients, properties such as molecular weight, reaction conditions, and so forth used in the specification and claims are to be understood as being modified in all instances by the term “about.” Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term “about” has the meaning reasonably ascribed to it by a person skilled in the art when used in conjunction with a stated numerical value or range, i.e. denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms “a,” “an,” “the” and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents, printed publications, journal articles, database accession numbers, and other written text throughout this specification (referenced materials herein). Each of the referenced materials are individually incorporated herein by reference in their entirety for their referenced teaching. Gene and protein database accession numbers are incorporate by reference in their entirety with the material that was publicly available as of the filing date of the application in which the accession number first appeared.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

Definitions and explanations used in the present disclosure are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary, 3rd Edition or a dictionary known to those of ordinary skill in the art, such as the Oxford Dictionary of Biochemistry and Molecular Biology (Ed. Anthony Smith, Oxford University Press, Oxford, 2004).

REFERENCES

1 Stoltz et al., Origins of cystic fibrosis lung disease. *N Engl J Med* 372, 351-362, doi:10.1056/NEJMra1300109, 2015.

2 Cohen & Prince, Cystic fibrosis: a mucosal immunodeficiency syndrome. *Nature medicine* 18, 509-519, doi: 10.1038/nm.2715, 2012.

3 Carter, Pathogen and autoantigen homologous regions within the cystic fibrosis transmembrane conductance regulator, CFTR) protein suggest an autoimmune treatable component of cystic fibrosis. *FEMS immunology and medical microbiology* 62, 197-214, doi:10.1111/j.1574-695X.2011.00803.x, 2011.

4 Budding et al., Anti-BPIFA1/SPLUNC1: a new autoantibody prevalent in patients with endstage cystic fibrosis. *Journal of cystic fibrosis: official journal of the European Cystic Fibrosis Society* 13, 281-288, doi:10.1016/j.jcf.2013.10.005, 2014.

5 Pedersen et al., An immunoproteomic approach for identification of clinical biomarkers for monitoring disease: application to cystic fibrosis. *Molecular & cellular proteomics*: MCP 4, 1052-1060, doi:10.1074/mcp.M400175-MCP200, 2005.

6 Mayer-Hamblett et al., Association between pulmonary function and sputum biomarkers in cystic fibrosis. *Am J Respir Crit Care Med* 175, 822-828, doi:10.1164/rccm.200609-1354OC, 2007.

7 von Bredow et al., Surfactant protein A and other bronchoalveolar lavage fluid proteins are altered in cystic fibrosis. *Eur Respir J* 17, 716-722, 2001.

8 Downey et al., The relationship of clinical and inflammatory markers to outcome in stable patients with cystic fibrosis. *Pediatric Pulmonology* 42, 216-220, doi: 10.1002/ppul.20553, 2007.

9 Rowe et al., Potential role of high-mobility group box 1 in cystic fibrosis airway disease. *Am J Respir Crit Care Med* 178, 822-831, doi:10.1164/rccm.200712-1894OC, 2008.

10 Sagel et al., Sputum biomarkers of inflammation in cystic fibrosis lung disease. *Proc Am Thorac Soc* 4, 406-417, doi:10.1513/pats.200703-044BR, 2007.

11 Rao et al., Proteomic identification of OprL as a seromarker for initial diagnosis of *Pseudomonas aeruginosa* infection of patients with cystic fibrosis. *J Clin Microbiol* 47, 2483-2488, doi:10.1128/JCM.02182-08, 2009.

12 Talwar et al., Development of a T7 Phage Display Library to Detect Sarcoidosis and Tuberculosis by a Panel of Novel Antigens. EBioMedicine 2, 341-350, doi:10.1016/j.ebiom.2015.03.007, 2015.

13 Talwar et al., T7 Phage Display Library a Promising Strategy to Detect Tuberculosis Specific Biomarkers. *Mycobacterial diseases: tuberculosis &leprosy* 6, doi: 10.4172/2161-1068.1000214, 2016.

14 Wang et al., Autoantibody signatures in prostate cancer. *N Engl J Med* 353, 1224-1235, doi:10.1056/NEJMoa051931, 2005.

15 Lin et al., Autoantibody approach for serum-based detection of head and neck cancer. *Cancer epidemiology,*

*biomarkers &prevention: a publication of the American Association for Cancer Research, cosponsored by the American Society of Preventive Oncology* 16, 2396-2405, doi:10.1158/1055-9965.EPI-07-0318, 2007.

16 Gibson & Cooke, A test for concentration of electrolytes in sweat in cystic fibrosis of the pancreas utilizing pilocarpine by iontophoresis. *Pediatrics* 23, 545-549, 1959.

17 Sheikh et al., Body composition and pulmonary function in cystic fibrosis. *Frontiers in Pediatrics* 2, 33, doi: 10.3389/fped.2014.00033, 2014.

18 Srivastava et al., Serum proteomic signature for cystic fibrosis using an antibody microarray platform. *Mol Gen Metabol* 87:303-310, doi:10.1016/j.ymgme.2005.10.021, 2006.

19 Rab et al., Cigarette smoke and CFTR: implications in the pathogenesis of COPD. *Am J Physiology—Lung Cell Mol Physiol* 305, L530-L541, 10.1152/ajplung.00039.2013, 2013.

20 Cantin, Cystic Fibrosis Transmembrane Conductance Regulator. Implications in Cystic Fibrosis and Chronic Obstructive Pulmonary Disease. *Annals of the American Thoracic Society* 13 Suppl 2, S150-155, doi:10.1513/AnnalsATS.201509-588KV, 2016.

21 Solomon et al., Therapeutic Approaches to Acquired Cystic Fibrosis Transmembrane Conductance Regulator Dysfunction in Chronic Bronchitis. *Annals of the American Thoracic Society* 13, S169-S176, doi: 10.1513/AnnalsATS.201509-601KV, 2016.

22 Lovewell et al., Mechanisms of phagocytosis and host clearance of *Pseudomonas aeruginosa. Am J Physiology—Lung Cell Mol Physiol* 306, L591-603, doi:10.1152/ajplung.00335.2013, 2014.

23 Hofer et al., Decreased expression of HLA-DQ and HLA-DR on cells of the monocytic lineage in cystic fibrosis. J Mol Med 92, 1293-1304, doi:10.1007/s00109-014-1200-z, 2014.

24 Stolz & Wolf, Endoplasmic reticulum associated protein degradation: a chaperone assisted journey to hell. *Biochimica et Biophysica Acta, BBA—Molecular Cell Research* 1803, 694-705, doi:10.1016/j.bbamcr.2010.02.005, 2010.

25 Meacham et al., The Hdj-2/Hsc70 chaperone pair facilitates early steps in CFTR biogenesis. *The EMBO J* 18, 1492-1505, doi:10.1093/emboj/18.6.1492, 1999.

26 Sly et al., Risk factors for bronchiectasis in children with cystic fibrosis. *NEJM* 368, 1963-1970, doi: 10.1056/NEJMoa1301725, 2013.

27 DeBoer et al., Automated CT scan scores of bronchiectasis and air trapping in cystic fibrosis. *CHEST Journal* 145, 593-603, doi: 10.1378/chest.13-0588, 2014.

28 Liu et al., Neutrophil elastase and elastase-rich cystic fibrosis sputum degranulate human eosinophils in vitro. *Am J Physiology—Lung Cell Mol Physiol* 276, L28-L34, 1999.

29 Lee et al., Thioredoxin and dihydrolipoic acid inhibit elastase activity in cystic fibrosis sputum. *Am J Physiology—Lung Cell Mol Physiol* 289, L875-L882, doi: 10.1152/ajplung.00103.2005, 2005.

30 Rubin et al., Thymosin β4 sequesters actin in cystic fibrosis sputum and decreases sputum cohesivity in vitro. *CHEST Journal* 130, 1433-1440, doi:10.1378/chest.130.5.1433, 2006.

31 Schirmbeck et al., Translation from cryptic reading frames of DNA vaccines generates an extended repertoire of immunogenic, MHC class I-restricted epitopes. *J Immunol* 174, 4647-4656, doi: 10.4049/jimmunol.174.8.4647, 2005.

32 Chatterjee et al., Diagnostic markers of ovarian cancer by high-throughput antigen cloning and detection on arrays. *Cancer research* 66, 1181-1190, doi:10.1158/0008-5472.CAN-04-2962, 2006.

33 Worthington et al., Small molecule control of bacterial biofilms. *Organic & biomolecular chemistry* 10, 7457-7474, doi:10.1039/c2ob25835h, 2012.

34 Lacy et al., Serum IgG response to an outer membrane porin protein of *Burkholderia cepacia* in patients with cystic fibrosis. *FEMS immunology and medical microbiology* 17, 87-94, 1997.

35 Aronoff, Outer membrane permeability in *Pseudomonas cepacia*: diminished porin content in a beta-lactam-resistant mutant and in resistant cystic fibrosis isolates. *Antimicrobial agents and chemotherapy* 32, 1636-1639, 1988.

36 Ciofu, *Pseudomonas aeruginosa* chromosomal beta-lactamase in patients with cystic fibrosis and chronic lung infection. Mechanism of antibiotic resistance and target of the humoral immune response. *APMIS*. Supplementum, 1-47, 2003.

37 MacEachran et al., Cif is negatively regulated by the TetR family repressor CifR. *Infection and immunity* 76, 3197-3206, doi:10.1128/IAI.00305-08, 2008.

38 Mahenthiralingam et al., Identification and characterization of a novel DNA marker associated with epidemic *Burkholderia cepacia* strains recovered from patients with cystic fibrosis. *Journal of clinical microbiology* 35, 808-816, 1997.

39 Cuthbertson & Nodwell, The TetR family of regulators. *Microbiology and molecular biology reviews: MMBR* 77, 440-475, doi:10.1128/MMBR.00018-13, 2013.

40 Valdivieso et al., The mitochondrial complex I activity is reduced in cells with impaired cystic fibrosis transmembrane conductance regulator, CFTR) function. *PLoS One* 7, e48059, doi:10.1371/journal.pone.0048059, 2012.

41 Schneider & Hunke, ATP-binding-cassette, ABC) transport systems: functional and structural aspects of the ATP-hydrolyzing subunits/domains. *FEMS microbiology reviews* 22, 1-20, doi: 10.1111/j. 1574-6976.1998.tb00358.x, 1998.

42 Gadsby et al., The ABC protein turned chloride channel whose failure causes cystic fibrosis. *Nature* 440, 477-483, doi:10.1038/nature04712, 2006.

43 Bem et al., Bacterial histidine kinases as novel antibacterial drug targets. *ACS Chemical Biology* 10, 213-224, doi: 10.1021/cb5007135, 2014.

44 Rana et al., Monolayer coated gold nanoparticles for delivery applications. *Advanced Drug Delivery Reviews* 64, 200-216, doi: 10.1016/j.addr.2011.08.006, 2012.

45 Raghu et al., An official ATS/ERS/JRS/ALAT statement: idiopathic pulmonary fibrosis: evidence-based guidelines for diagnosis and management. *Am J Resp Critical Care Med* 183, 788-824, doi:10.1164/rccm.2009-040GL, 2011.

46 Ritchie et al., limma powers differential expression analyses for RNA-sequencing and microarray studies. *Nucleic Acids Res* 43, e47, doi:10.1093/nar/gkv007, 2015.

47 R: A language and environment for statistical computing, R Foundation for Statistical Computing, Vienna, Austria., 2015.

48 Ritchie et al., A comparison of background correction methods for two-colour microarrays. *Bioinformatics* 23, 2700-2707, doi:10.1093/bioinformatics/btm412 Bioinformatics, 2007.

49 Yang et al., Normalization for cDNA microarray data: a robust composite method addressing single and multiple slide systematic variation. *Nucleic Acids Res* 30, e15, doi.org/10.1093/nar/30.4.e15, 2002.

50 Benjamini & Hochberg, Controlling the false discovery rate: a practical and powerful approach to multiple testing. *Journal of the Royal Statistical Society. Series B, Methodological*) 289-300, doi.org/10.1016/0306-9877(95)90228-7, 1995.

What is claimed is:

1. A kit for detecting whether a subject has cystic fibrosis comprising a detectable label and at least four distinct mimotopes bound to a solid surface, the mimotopes selected from SEQ ID NO: 1, SEQ ID NO: 2, SEQ ID NO: 5, SEQ ID NO: 6, SEQ ID NO: 9, SEQ ID NO: 12, SEQ ID NO: 17, and SEQ ID NO: 18 respectively.

2. The kit of claim 1, wherein the solid surface is a microarray.

3. The kit of claim 1, wherein the detectable label comprises a radioactive isotope, enzyme, dye, fluorescent dye, magnetic bead, or biotin.

4. The kit of claim 1, wherein the solid surface further comprises at least one mimotope selected from SEQ ID NO: 11, SEQ ID NO: 14, SEQ ID NO: 7, SEQ ID NO: 13, SEQ ID NO: 15, SEQ ID NO: 16, SEQ ID NO: 19, SEQ ID NO: 3, SEQ ID NO: 4, SEQ ID NO: 8, or SEQ ID NO: 19.

5. The kit of claim 1, further comprising one or more reagents to perform an enzyme-linked immunosorbent assay (ELISA), a radioimmunoassay (RIA), a Western blot, an immunoprecipitation, an immunohistochemical staining, flow cytometry, fluorescence-activated cell sorting (FACS), an enzyme substrate color method, and/or an antigen-antibody agglutination.

6. A method of diagnosing cystic fibrosis in a subject, the method comprising:

obtaining a serum sample derived from the subject;

contacting the serum sample with a solid surface comprising at least four different labeled mimotopes, the mimotopes selected from SEQ ID NO: 1, SEQ ID NO: 2, SEQ ID NO: 5, SEQ ID NO: 6, SEQ ID NO: 9, SEQ ID NO: 12, SEQ ID NO: 17, and SEQ ID NO: 18; detecting binding of antibodies in the serum sample to the mimotopes; obtaining a level of antibodies in the serum sample for each mimotope, the level based on the detected binding; comparing the level to a reference level; and diagnosing the subject as having cystic fibrosis based on increased levels of antibodies bound to one or more of SEQ ID NO: 2, SEQ ID NO: 6, SEQ ID NO: 9, SEQ ID NO: 12, SEQ ID NO: 17, or decreased levels of antibodies bound to one or more of SEQ ID NO: 1, SEQ ID NO: 5, or SEQ ID NO: 18 relative to the reference level.

7. The method of claim 6, wherein detecting binding of antibodies in the sample to the mimotopes comprises contacting the sample with a plurality of probes each comprising a detectable label, wherein each probe binds to the bound antibodies.

8. The method of claim 6, wherein a score is determined by combining the level of each antibody in the serum sample that binds a respective.

9. The method of claim 8, wherein the score is a weighted score.

10. The method of claim 6, wherein the reference level is from a subject known not to have cystic fibrosis.

* * * * *

SEQUENCE LISTING

```
<160> NUMBER OF SEQ ID NOS: 96

<210> SEQ ID NO 1
<211> LENGTH: 17
<212> TYPE: PRT
<213> ORGANISM: Burkholderia cepacia

<400> SEQUENCE: 1

Asp Leu Ser Ser Glu Val Ala Thr His Gln Pro Ile Ile Ala Cys Leu
1               5                   10                  15

Pro


<210> SEQ ID NO 2
<211> LENGTH: 18
<212> TYPE: PRT
<213> ORGANISM: Burkholderia cepacia

<400> SEQUENCE: 2

Gly Lys Tyr Asn Ser Thr Phe Thr Ser Ser Ile Ile His Asn Lys Asn
1               5                   10                  15

Met Lys


<210> SEQ ID NO 3
<211> LENGTH: 8
<212> TYPE: PRT
<213> ORGANISM: Burkholderia cepacia

<400> SEQUENCE: 3

Tyr Met Cys Phe Ser Leu Pro Pro
1               5


<210> SEQ ID NO 4
<211> LENGTH: 34
<212> TYPE: PRT
<213> ORGANISM: Burkholderia cepacia

<400> SEQUENCE: 4

Gly Ile Thr Ser Ala Arg Leu Gly Thr Gly Thr Gly Glu Arg Leu Arg
1               5                   10                  15

Ser Gly Cys Val Gln Gly Leu Val Gly Met Gly Arg Pro Val Asp Arg
            20                  25                  30

Ala Cys


<210> SEQ ID NO 5
<211> LENGTH: 12
<212> TYPE: PRT
<213> ORGANISM: Homo sapiens

<400> SEQUENCE: 5

Ser Ala Thr Ser Ser Leu Ala Val Tyr Ser Ile Leu
1               5                   10


<210> SEQ ID NO 6
<211> LENGTH: 15
<212> TYPE: PRT
<213> ORGANISM: Pseudomonas sp. BRH_c35
```

<400> SEQUENCE: 6

Leu Pro Arg Ile Phe Ile Glu Leu Ala Gln His Gln Ala Arg Val
1 5 10 15

<210> SEQ ID NO 7
<211> LENGTH: 16
<212> TYPE: PRT
<213> ORGANISM: Pseudomonas Aeruginosa

<400> SEQUENCE: 7

Ala Gly Ile Ser Arg Glu Leu Val Asp Lys Leu Ala Ala Ala Leu Glu
1 5 10 15

<210> SEQ ID NO 8
<211> LENGTH: 49
<212> TYPE: PRT
<213> ORGANISM: Homo sapiens

<400> SEQUENCE: 8

Asp Ala Pro Ser Pro Leu Pro Glu Thr Thr Glu Asn Val Val Cys Ala
1 5 10 15

Leu Gly Leu Thr Val Gly Leu Val Gly Ile Ile Ile Gly Thr Ile Phe
20 25 30

Ile Ile Lys Gly Val Arg Lys Ser Asn Ala Ala Glu Arg Arg Gly Pro
35 40 45

Leu

<210> SEQ ID NO 9
<211> LENGTH: 16
<212> TYPE: PRT
<213> ORGANISM: Burkholderia cepacia

<400> SEQUENCE: 9

Ser Arg Asn Cys Val Asn Thr Trp Val Phe Leu Asn Leu Met Gln Asp
1 5 10 15

<210> SEQ ID NO 10
<211> LENGTH: 29
<212> TYPE: PRT
<213> ORGANISM: Burkholderia cepacia

<400> SEQUENCE: 10

Leu Arg Pro Pro Asn Asn Pro Pro Pro Asn Thr Asn Tyr Leu Thr Pro
1 5 10 15

Thr Pro His Asn His Gly Lys Pro Thr Pro Leu Ile Gln
20 25

<210> SEQ ID NO 11
<211> LENGTH: 130
<212> TYPE: PRT
<213> ORGANISM: Homo sapiens

<400> SEQUENCE: 11

Ser Ala Lys Tyr Lys Glu Thr Arg Leu Lys Glu Lys Glu Asp Ala Leu
1 5 10 15

Thr Arg Thr Glu Leu Glu Thr Leu Gln Lys Gln Lys Lys Val Lys Lys
20 25 30

Pro Lys Pro Glu Phe Pro Val Tyr Thr Pro Leu Glu Thr Thr Tyr Ile
35 40 45

Gln Ser Tyr Asp His Gly Thr Ser Ile Glu Glu Ile Glu Glu Gln Met

```
    50                  55                  60

Asp Asp Trp Leu Glu Asn Arg Asn Arg Thr Gln Lys Lys Gln Ala Pro
65                  70                  75                  80

Glu Trp Thr Glu Glu Asp Leu Ser Gln Leu Thr Arg Ser Met Val Lys
                85                  90                  95

Phe Pro Gly Gly Thr Pro Gly Arg Trp Glu Lys Ile Ala His Glu Leu
            100                 105                 110

Gly Arg Ser Val Thr Asp Val Thr Thr Lys Ala Lys Leu Ala Ala Ala
        115                 120                 125

Leu Glu
    130


<210> SEQ ID NO 12
<211> LENGTH: 23
<212> TYPE: PRT
<213> ORGANISM: Pseudomonas aeruginosa

<400> SEQUENCE: 12

Arg Asp Pro Gln Cys Trp Arg Trp Asp Leu Val Arg Gly Val Trp Val
1               5                   10                  15

Thr Gly Thr Asp Pro Ser Trp
            20


<210> SEQ ID NO 13
<211> LENGTH: 29
<212> TYPE: PRT
<213> ORGANISM: Pseudomonas fluorescens

<400> SEQUENCE: 13

Arg Asp Thr Gly Asn Ser Ile Phe Leu Ser Asn Gly Arg Arg Tyr Ala
1               5                   10                  15

Leu Lys Phe Gly Trp Asp Thr Gln Phe Ser Phe Ile Phe
            20                  25


<210> SEQ ID NO 14
<211> LENGTH: 20
<212> TYPE: PRT
<213> ORGANISM: Burkholderia cepacia

<400> SEQUENCE: 14

Pro Tyr Val Gly Met Val Ala Thr Thr Ser Pro Pro Ser Pro Pro Pro
1               5                   10                  15

Ala Val Thr Thr
            20


<210> SEQ ID NO 15
<211> LENGTH: 66
<212> TYPE: PRT
<213> ORGANISM: Homo sapiens

<400> SEQUENCE: 15

Val Ala Thr Ala Gln Thr Arg Leu Arg Ser Tyr Ser Cys Ala Ser Leu
1               5                   10                  15

Arg Phe Ser Ser Ala Thr Met Ser Asp Lys Pro Asp Met Ala Glu Ile
            20                  25                  30

Glu Lys Phe Asp Lys Ser Lys Leu Lys Lys Thr Glu Thr Gln Glu Lys
        35                  40                  45

Asn Pro Leu Pro Ser Lys Glu Thr Ile Glu Gln Glu Lys Gln Ala Gly
    50                  55                  60
```

Glu Ser
65

<210> SEQ ID NO 16
<211> LENGTH: 9
<212> TYPE: PRT
<213> ORGANISM: Pseudomonas aeruginosa

<400> SEQUENCE: 16

Ile Gln His Gln His Leu Gly Gln Ile
1 5

<210> SEQ ID NO 17
<211> LENGTH: 27
<212> TYPE: PRT
<213> ORGANISM: Pseudomonas aeruginosa

<400> SEQUENCE: 17

Val Asp Lys Ser Val Leu Leu Ser Leu Gly Arg Lys Lys Tyr Gly Ala
1 5 10 15

Val Gly Ser Leu Ser Gln Ser Thr Gly Gly His
20 25

<210> SEQ ID NO 18
<211> LENGTH: 19
<212> TYPE: PRT
<213> ORGANISM: Burkholderia cepacia

<400> SEQUENCE: 18

Ser Leu Gly Ala Met Val Cys Leu His Ser Val Pro Ser His Lys Ala
1 5 10 15

Thr Trp Ile

<210> SEQ ID NO 19
<211> LENGTH: 16
<212> TYPE: PRT
<213> ORGANISM: Pseudomonas aeruginosa

<400> SEQUENCE: 19

Val Thr Leu Met Arg Gln Arg Val Met Met Met Gly Arg His Thr Thr
1 5 10 15

<210> SEQ ID NO 20
<211> LENGTH: 213
<212> TYPE: PRT
<213> ORGANISM: Homo sapiens

<400> SEQUENCE: 20

Lys Ile Asp Arg Leu Asp Gly Ala His Ala Pro Glu Leu Thr Lys Lys
1 5 10 15

Val Gln Arg His Ala Ser Ser Gly Ser Phe Leu Pro Ser Ala Asn Glu
20 25 30

His Leu Lys Glu Asp Leu Asn Leu Arg Leu Lys Lys Leu Thr His Ala
35 40 45

Ala Pro Cys Met Leu Phe Met Lys Gly Thr Pro Gln Glu Pro Arg Cys
50 55 60

Gly Phe Ser Lys Gln Met Val Glu Ile Leu His Lys His Asn Ile Gln
65 70 75 80

Phe Ser Ser Phe Asp Ile Phe Ser Asp Glu Glu Val Arg Gln Gly Leu
85 90 95

Lys Ala Tyr Ser Ser Trp Pro Thr Tyr Pro Gln Leu Tyr Val Ser Gly

```
            100                 105                 110

Glu Leu Ile Gly Gly Leu Asp Ile Ile Lys Glu Leu Glu Ala Ser Glu
        115                 120                 125

Glu Leu Asp Thr Ile Cys Pro Lys Ala Pro Lys Leu Glu Glu Arg Leu
    130                 135                 140

Lys Val Leu Thr Asn Lys Ala Ser Val Met Leu Phe Met Lys Gly Asn
145                 150                 155                 160

Lys Gln Glu Ala Lys Cys Gly Phe Ser Lys Gln Ile Leu Glu Ile Leu
                165                 170                 175

Asn Ser Thr Gly Val Glu Tyr Glu Thr Phe Asp Ile Leu Glu Asp Glu
            180                 185                 190

Glu Val Arg Gln Gly Leu Lys Ala Tyr Ser Asn Trp Pro Ser Leu Arg
        195                 200                 205

Pro His Ser Ser Asn
    210


<210> SEQ ID NO 21
<211> LENGTH: 25
<212> TYPE: PRT
<213> ORGANISM: Pseudomonas aeruginosa

<400> SEQUENCE: 21

Ser Gly Ser Leu Glu Val Arg Ser Cys Thr Pro Ala Trp Val Thr Glu
1               5                   10                  15

Arg Asn Phe Ile Ser Lys Lys Lys Gly
            20                  25


<210> SEQ ID NO 22
<211> LENGTH: 18
<212> TYPE: PRT
<213> ORGANISM: Pseudomonas aeruginosa

<400> SEQUENCE: 22

Gly Lys Tyr Asn Ser Thr Phe Thr Ser Ser Ile Ile His Asn Lys Asn
1               5                   10                  15

Met Lys


<210> SEQ ID NO 23
<211> LENGTH: 24
<212> TYPE: PRT
<213> ORGANISM: Campylobacter jejuni

<400> SEQUENCE: 23

Ser Ile Ser Pro Phe Thr Val Thr Lys His Lys Pro Thr Ser Gln Gly
1               5                   10                  15

Leu Glu Tyr Leu His Ala Phe Ala
            20


<210> SEQ ID NO 24
<211> LENGTH: 87
<212> TYPE: PRT
<213> ORGANISM: Pseudomonas aeruginosa

<400> SEQUENCE: 24

Pro Val Glu Gly Arg Gly Arg Pro Ser Pro Leu His Val Ala Gln His
1               5                   10                  15

Ser Tyr Thr Gly Val Glu Ala Gln Pro Leu Asn His Gln Val Leu His
            20                  25                  30

Val Ala Gly Arg Asp Gly Leu Pro Val Ala Val Asn Gly Thr Leu Ser
```

```
        35                  40                  45

Asp Asp Asp Asp Val Gln Ser Gly Pro Thr Ala Pro Ser Leu Thr Gln
    50                  55                  60

Pro Leu Thr His Glu Val Leu Pro Ala Val Leu Gly Trp Ser Leu Gly
65                  70                  75                  80

Asp Glu Gln Pro Val Gly Pro
                85


<210> SEQ ID NO 25
<211> LENGTH: 14
<212> TYPE: PRT
<213> ORGANISM: Streptomyces sp. NRRL B-24720

<400> SEQUENCE: 25

Ser Arg Met Ala Arg Ser Ser Trp Arg Arg Thr Ser Ala Ala
1               5                   10


<210> SEQ ID NO 26
<211> LENGTH: 29
<212> TYPE: PRT
<213> ORGANISM: Pseudomonas aeruginosa

<400> SEQUENCE: 26

Ser Ala Thr Cys Ser Leu Phe Ala Ala Leu Thr Val Pro Asp Ala Cys
1               5                   10                  15

Pro Arg Thr Arg Pro Leu Arg Asn Ser Ser Phe Glu Thr
            20                  25


<210> SEQ ID NO 27
<211> LENGTH: 5
<212> TYPE: PRT
<213> ORGANISM: Pseudomonas aeruginosa

<400> SEQUENCE: 27

Ser Val Arg Arg Gly
1               5


<210> SEQ ID NO 28
<211> LENGTH: 21
<212> TYPE: DNA
<213> ORGANISM: Artificial Sequence
<220> FEATURE:
<223> OTHER INFORMATION: Sequencing Primer

<400> SEQUENCE: 28

gttctatccg caacgttatg g                                             21


<210> SEQ ID NO 29
<211> LENGTH: 22
<212> TYPE: DNA
<213> ORGANISM: Artificial Sequence
<220> FEATURE:
<223> OTHER INFORMATION: Sequencing Primer

<400> SEQUENCE: 29

ggaggaaagt cgtttttgg gg                                             22


<210> SEQ ID NO 30
<211> LENGTH: 21
<212> TYPE: DNA
<213> ORGANISM: Artificial Sequence
<220> FEATURE:
<223> OTHER INFORMATION: Sequencing Primer
```

<400> SEQUENCE: 30
tgctaaggac aacgttatcg g 21

<210> SEQ ID NO 31
<211> LENGTH: 12
<212> TYPE: PRT
<213> ORGANISM: Pseudomonas sp. BRH_c35

<400> SEQUENCE: 31

Leu Pro Arg Ile Phe Ile Glu Leu Ala Gln His Gln
1 5 10

<210> SEQ ID NO 32
<211> LENGTH: 12
<212> TYPE: PRT
<213> ORGANISM: Pseudomonas sp. BRH_c35
<220> FEATURE:
<221> NAME/KEY: MISC_FEATURE
<222> LOCATION: (2)..(2)
<223> OTHER INFORMATION: X is P or E
<220> FEATURE:
<221> NAME/KEY: MISC_FEATURE
<222> LOCATION: (10)..(10)
<223> OTHER INFORMATION: X is Q or R
<220> FEATURE:
<221> NAME/KEY: MISC_FEATURE
<222> LOCATION: (12)..(12)
<223> OTHER INFORMATION: X is Q or E

<400> SEQUENCE: 32

Leu Xaa Arg Ile Phe Ile Glu Leu Ala Xaa His Xaa
1 5 10

<210> SEQ ID NO 33
<211> LENGTH: 12
<212> TYPE: PRT
<213> ORGANISM: Pseudomonas sp. BRH_c35

<400> SEQUENCE: 33

Leu Glu Arg Ile Phe Ile Glu Leu Ala Arg His Glu
1 5 10

<210> SEQ ID NO 34
<211> LENGTH: 127
<212> TYPE: PRT
<213> ORGANISM: Homo sapiens

<400> SEQUENCE: 34

Ala Lys Tyr Lys Glu Thr Arg Leu Lys Glu Lys Glu Asp Ala Leu Thr
1 5 10 15

Arg Thr Glu Leu Glu Thr Leu Gln Lys Gln Lys Lys Val Lys Lys Pro
20 25 30

Lys Pro Glu Phe Pro Val Tyr Thr Pro Leu Glu Thr Thr Tyr Ile Gln
35 40 45

Ser Tyr Asp His Gly Thr Ser Ile Glu Glu Ile Glu Glu Gln Met Glu
50 55 60

Thr Asp Asp Trp Leu Glu Asn Arg Asn Arg Thr Gln Lys Lys Gln Ala
65 70 75 80

Pro Glu Trp Thr Glu Glu Asp Leu Ser Gln Leu Thr Arg Ser Met Glu
85 90 95

Thr Val Lys Phe Pro Gly Gly Thr Pro Gly Arg Trp Glu Lys Ile Ala
100 105 110

His Glu Leu Gly Arg Ser Val Thr Asp Val Thr Thr Lys Ala Lys 115 120 125

<210> SEQ ID NO 35
<211> LENGTH: 123
<212> TYPE: PRT
<213> ORGANISM: Homo sapiens

<400> SEQUENCE: 35

Ala Lys Tyr Lys Glu Thr Arg Leu Lys Glu Lys Glu Asp Ala Leu Thr
1 5 10 15

Arg Thr Glu Leu Glu Thr Leu Gln Lys Gln Lys Lys Val Lys Lys Pro
20 25 30

Lys Pro Glu Phe Pro Val Tyr Thr Pro Leu Glu Thr Thr Tyr Ile Gln
35 40 45

Ser Tyr Asp His Gly Thr Ser Ile Glu Glu Ile Glu Glu Gln Met Asp
50 55 60

Asp Trp Leu Glu Asn Arg Asn Arg Thr Gln Lys Lys Gln Ala Pro Glu
65 70 75 80

Trp Thr Glu Glu Asp Leu Ser Gln Leu Thr Arg Ser Met Val Lys Phe
85 90 95

Pro Gly Gly Thr Pro Gly Arg Trp Glu Lys Ile Ala His Glu Leu Gly
100 105 110

Arg Ser Val Thr Asp Val Thr Thr Lys Ala Lys
115 120

<210> SEQ ID NO 36
<211> LENGTH: 123
<212> TYPE: PRT
<213> ORGANISM: Homo sapiens

<400> SEQUENCE: 36

Ala Lys Tyr Lys Glu Thr Arg Leu Lys Glu Lys Glu Asp Ala Leu Thr
1 5 10 15

Arg Thr Glu Leu Glu Thr Leu Gln Lys Gln Lys Lys Val Lys Lys Pro
20 25 30

Lys Pro Glu Phe Pro Val Tyr Thr Pro Leu Glu Thr Thr Tyr Ile Gln
35 40 45

Ser Tyr Asp His Gly Thr Ser Ile Glu Glu Ile Glu Glu Gln Met Asp
50 55 60

Asp Trp Leu Glu Asn Arg Asn Arg Thr Gln Lys Lys Gln Ala Pro Glu
65 70 75 80

Trp Thr Glu Glu Asp Leu Ser Gln Leu Thr Arg Ser Met Val Lys Phe
85 90 95

Pro Gly Gly Thr Pro Gly Arg Trp Glu Lys Ile Ala His Glu Leu Gly
100 105 110

Arg Ser Val Thr Asp Val Thr Thr Lys Ala Lys
115 120

<210> SEQ ID NO 37
<211> LENGTH: 10
<212> TYPE: PRT
<213> ORGANISM: Burkholderia cepacia

<400> SEQUENCE: 37

Thr Thr Ser Pro Pro Ser Pro Pro Pro Ala
1 5 10

<210> SEQ ID NO 38

<211> LENGTH: 10
<212> TYPE: PRT
<213> ORGANISM: Burkholderia cepacia
<220> FEATURE:
<221> NAME/KEY: MISC_FEATURE
<222> LOCATION: (7)..(7)
<223> OTHER INFORMATION: X is P or N

<400> SEQUENCE: 38

Thr Thr Ser Pro Pro Ser Xaa Pro Pro Ala
1               5                   10

<210> SEQ ID NO 39
<211> LENGTH: 10
<212> TYPE: PRT
<213> ORGANISM: Burkholderia cepacia

<400> SEQUENCE: 39

Thr Thr Ser Pro Pro Ser Asn Pro Pro Ala
1               5                   10

<210> SEQ ID NO 40
<211> LENGTH: 11
<212> TYPE: PRT
<213> ORGANISM: Pseudomonas Aeruginosa

<400> SEQUENCE: 40

Glu Leu Val Asp Lys Leu Ala Ala Ala Leu Glu
1               5                   10

<210> SEQ ID NO 41
<211> LENGTH: 10
<212> TYPE: PRT
<213> ORGANISM: Pseudomonas aeruginosa

<400> SEQUENCE: 41

Trp Arg Trp Asp Leu Val Arg Gly Val Trp
1               5                   10

<210> SEQ ID NO 42
<211> LENGTH: 10
<212> TYPE: PRT
<213> ORGANISM: Pseudomonas aeruginosa
<220> FEATURE:
<221> NAME/KEY: MISC_FEATURE
<222> LOCATION: (5)..(5)
<223> OTHER INFORMATION: X is L or N
<220> FEATURE:
<221> NAME/KEY: MISC_FEATURE
<222> LOCATION: (7)..(7)
<223> OTHER INFORMATION: X is R or K
<220> FEATURE:
<221> NAME/KEY: MISC_FEATURE
<222> LOCATION: (9)..(9)
<223> OTHER INFORMATION: X is V or absent

<400> SEQUENCE: 42

Trp Arg Trp Asp Xaa Val Xaa Gly Xaa Trp
1               5                   10

<210> SEQ ID NO 43
<211> LENGTH: 9
<212> TYPE: PRT
<213> ORGANISM: Pseudomonas aeruginosa

<400> SEQUENCE: 43

Trp Arg Trp Asp Asn Val Lys Gly Trp
1               5

<210> SEQ ID NO 44
<211> LENGTH: 10
<212> TYPE: PRT
<213> ORGANISM: Burkholderia cepacia

<400> SEQUENCE: 44

Thr Trp Val Phe Leu Asn Leu Met Gln Asp
1 5 10

<210> SEQ ID NO 45
<211> LENGTH: 10
<212> TYPE: PRT
<213> ORGANISM: Burkholderia cepacia
<220> FEATURE:
<221> NAME/KEY: MISC_FEATURE
<222> LOCATION: (2)..(2)
<223> OTHER INFORMATION: X is W or L
<220> FEATURE:
<221> NAME/KEY: MISC_FEATURE
<222> LOCATION: (5)..(5)
<223> OTHER INFORMATION: X is L or A
<220> FEATURE:
<221> NAME/KEY: MISC_FEATURE
<222> LOCATION: (8)..(8)
<223> OTHER INFORMATION: X is M or I

<400> SEQUENCE: 45

Thr Xaa Val Phe Xaa Asn Leu Xaa Gln Asp
1 5 10

<210> SEQ ID NO 46
<211> LENGTH: 10
<212> TYPE: PRT
<213> ORGANISM: Burkholderia cepacia

<400> SEQUENCE: 46

Thr Leu Val Phe Ala Asn Leu Ile Gln Asp
1 5 10

<210> SEQ ID NO 47
<211> LENGTH: 12
<212> TYPE: PRT
<213> ORGANISM: Pseudomonas fluorescens

<400> SEQUENCE: 47

Arg Asp Thr Gly Asn Ser Ile Phe Leu Ser Asn Gly
1 5 10

<210> SEQ ID NO 48
<211> LENGTH: 12
<212> TYPE: PRT
<213> ORGANISM: Pseudomonas fluorescens
<220> FEATURE:
<221> NAME/KEY: MISC_FEATURE
<222> LOCATION: (3)..(3)
<223> OTHER INFORMATION: X is T or S
<220> FEATURE:
<221> NAME/KEY: MISC_FEATURE
<222> LOCATION: (5)..(5)
<223> OTHER INFORMATION: X is N or absent

<400> SEQUENCE: 48

Arg Asp Xaa Gly Xaa Ser Ile Phe Leu Ser Asn Gly
1 5 10

<210> SEQ ID NO 49
<211> LENGTH: 11

<212> TYPE: PRT
<213> ORGANISM: Pseudomonas fluorescens

<400> SEQUENCE: 49

Arg Asp Ser Gly Ser Ile Phe Leu Ser Asn Gly
1 5 10

<210> SEQ ID NO 50
<211> LENGTH: 11
<212> TYPE: PRT
<213> ORGANISM: Burkholderia cepacia

<400> SEQUENCE: 50

Gly Lys Tyr Asn Ser Thr Phe Thr Ser Ser Ile
1 5 10

<210> SEQ ID NO 51
<211> LENGTH: 11
<212> TYPE: PRT
<213> ORGANISM: Burkholderia cepacia
<220> FEATURE:
<221> NAME/KEY: MISC_FEATURE
<222> LOCATION: (2)..(2)
<223> OTHER INFORMATION: X is K or S
<220> FEATURE:
<221> NAME/KEY: MISC_FEATURE
<222> LOCATION: (4)..(4)
<223> OTHER INFORMATION: X is N or D
<220> FEATURE:
<221> NAME/KEY: MISC_FEATURE
<222> LOCATION: (5)..(5)
<223> OTHER INFORMATION: X is S or G
<220> FEATURE:
<221> NAME/KEY: MISC_FEATURE
<222> LOCATION: (8)..(8)
<223> OTHER INFORMATION: X is T or A

<400> SEQUENCE: 51

Gly Xaa Tyr Xaa Xaa Thr Phe Xaa Ser Ser Ile
1 5 10

<210> SEQ ID NO 52
<211> LENGTH: 11
<212> TYPE: PRT
<213> ORGANISM: Burkholderia cepacia

<400> SEQUENCE: 52

Gly Ser Tyr Asp Gly Thr Phe Ala Ser Ser Ile
1 5 10

<210> SEQ ID NO 53
<211> LENGTH: 65
<212> TYPE: PRT
<213> ORGANISM: Homo sapiens

<400> SEQUENCE: 53

Ala Thr Ala Gln Thr Arg Leu Arg Ser Tyr Ser Cys Ala Ser Leu Arg
1 5 10 15

Phe Ser Ser Ala Thr Met Ser Asp Lys Pro Asp Met Ala Glu Ile Glu
20 25 30

Lys Phe Asp Lys Ser Lys Leu Lys Lys Thr Glu Thr Gln Glu Lys Asn
35 40 45

Pro Leu Pro Ser Lys Glu Thr Ile Glu Gln Glu Lys Gln Ala Gly Glu
50 55 60

Ser
65

<210> SEQ ID NO 54
<211> LENGTH: 8
<212> TYPE: PRT
<213> ORGANISM: Pseudomonas aeruginosa

<400> SEQUENCE: 54

Ile Gln His Gln His Leu Gly Gln
1 5

<210> SEQ ID NO 55
<211> LENGTH: 8
<212> TYPE: PRT
<213> ORGANISM: Pseudomonas aeruginosa
<220> FEATURE:
<221> NAME/KEY: MISC_FEATURE
<222> LOCATION: (3)..(3)
<223> OTHER INFORMATION: X is H or absent

<400> SEQUENCE: 55

Ile Gln Xaa Gln His Leu Gly Gln
1 5

<210> SEQ ID NO 56
<211> LENGTH: 7
<212> TYPE: PRT
<213> ORGANISM: Pseudomonas aeruginosa

<400> SEQUENCE: 56

Ile Gln Gln His Leu Gly Gln
1 5

<210> SEQ ID NO 57
<211> LENGTH: 14
<212> TYPE: PRT
<213> ORGANISM: Pseudomonas aeruginosa

<400> SEQUENCE: 57

Asp Lys Ser Val Leu Leu Ser Leu Gly Arg Lys Lys Tyr Gly
1 5 10

<210> SEQ ID NO 58
<211> LENGTH: 14
<212> TYPE: PRT
<213> ORGANISM: Pseudomonas aeruginosa
<220> FEATURE:
<221> NAME/KEY: MISC_FEATURE
<222> LOCATION: (5)..(5)
<223> OTHER INFORMATION: X is L or R
<220> FEATURE:
<221> NAME/KEY: MISC_FEATURE
<222> LOCATION: (9)..(9)
<223> OTHER INFORMATION: X is G or absent
<220> FEATURE:
<221> NAME/KEY: MISC_FEATURE
<222> LOCATION: (10)..(10)
<223> OTHER INFORMATION: X is R or T
<220> FEATURE:
<221> NAME/KEY: MISC_FEATURE
<222> LOCATION: (12)..(12)
<223> OTHER INFORMATION: X is K or N

<400> SEQUENCE: 58

Asp Lys Ser Val Xaa Leu Ser Leu Xaa Xaa Lys Xaa Tyr Gly
1 5 10

<210> SEQ ID NO 59
<211> LENGTH: 13

<212> TYPE: PRT
<213> ORGANISM: Pseudomonas aeruginosa

<400> SEQUENCE: 59

Asp Lys Ser Val Arg Leu Ser Leu Thr Lys Asn Tyr Gly
1 5 10

<210> SEQ ID NO 60
<211> LENGTH: 10
<212> TYPE: PRT
<213> ORGANISM: Burkholderia cepacia

<400> SEQUENCE: 60

Ser Val Pro Ser His Lys Ala Thr Trp Ile
1 5 10

<210> SEQ ID NO 61
<211> LENGTH: 12
<212> TYPE: PRT
<213> ORGANISM: Burkholderia cepacia
<220> FEATURE:
<221> NAME/KEY: MISC_FEATURE
<222> LOCATION: (4)..(4)
<223> OTHER INFORMATION: X is S or A
<220> FEATURE:
<221> NAME/KEY: MISC_FEATURE
<222> LOCATION: (5)..(5)
<223> OTHER INFORMATION: X is H or Q
<220> FEATURE:
<221> NAME/KEY: MISC_FEATURE
<222> LOCATION: (6)..(6)
<223> OTHER INFORMATION: X is K or N
<220> FEATURE:
<221> NAME/KEY: MISC_FEATURE
<222> LOCATION: (9)..(9)
<223> OTHER INFORMATION: X is G or absent
<220> FEATURE:
<221> NAME/KEY: MISC_FEATURE
<222> LOCATION: (10)..(10)
<223> OTHER INFORMATION: X is N or absent

<400> SEQUENCE: 61

Ser Val Pro Xaa Xaa Xaa Ala Thr Xaa Xaa Trp Ile
1 5 10

<210> SEQ ID NO 62
<211> LENGTH: 12
<212> TYPE: PRT
<213> ORGANISM: Burkholderia cepacia

<400> SEQUENCE: 62

Ser Val Pro Ala Gln Asn Ala Thr Gly Asn Trp Ile
1 5 10

<210> SEQ ID NO 63
<211> LENGTH: 8
<212> TYPE: PRT
<213> ORGANISM: Burkholderia cepacia
<220> FEATURE:
<221> NAME/KEY: MISC_FEATURE
<222> LOCATION: (3)..(3)
<223> OTHER INFORMATION: X is C or S
<220> FEATURE:
<221> NAME/KEY: MISC_FEATURE
<222> LOCATION: (4)..(4)
<223> OTHER INFORMATION: X is F or A

<400> SEQUENCE: 63

Tyr Met Xaa Xaa Ser Leu Pro Pro
1 5

<210> SEQ ID NO 64
<211> LENGTH: 8
<212> TYPE: PRT
<213> ORGANISM: Burkholderia cepacia

<400> SEQUENCE: 64

Tyr Met Ser Ala Ser Leu Pro Pro
1               5

<210> SEQ ID NO 65
<211> LENGTH: 18
<212> TYPE: PRT
<213> ORGANISM: Burkholderia cepacia

<400> SEQUENCE: 65

Arg Leu Arg Ser Gly Cys Val Gln Gly Leu Val Gly Met Gly Arg Pro
1               5                   10                  15

Val Asp

<210> SEQ ID NO 66
<211> LENGTH: 18
<212> TYPE: PRT
<213> ORGANISM: Burkholderia cepacia
<220> FEATURE:
<221> NAME/KEY: MISC_FEATURE
<222> LOCATION: (3)..(3)
<223> OTHER INFORMATION: X is R or D
<220> FEATURE:
<221> NAME/KEY: MISC_FEATURE
<222> LOCATION: (5)..(5)
<223> OTHER INFORMATION: X is G or Y
<220> FEATURE:
<221> NAME/KEY: MISC_FEATURE
<222> LOCATION: (7)..(7)
<223> OTHER INFORMATION: X is V or F
<220> FEATURE:
<221> NAME/KEY: MISC_FEATURE
<222> LOCATION: (8)..(8)
<223> OTHER INFORMATION: X is Q or E
<220> FEATURE:
<221> NAME/KEY: MISC_FEATURE
<222> LOCATION: (10)..(10)
<223> OTHER INFORMATION: X is L or V
<220> FEATURE:
<221> NAME/KEY: MISC_FEATURE
<222> LOCATION: (12)..(12)
<223> OTHER INFORMATION: X is G or A
<220> FEATURE:
<221> NAME/KEY: MISC_FEATURE
<222> LOCATION: (13)..(13)
<223> OTHER INFORMATION: X is M or P
<220> FEATURE:
<221> NAME/KEY: MISC_FEATURE
<222> LOCATION: (17)..(17)
<223> OTHER INFORMATION: X is V or I

<400> SEQUENCE: 66

Arg Leu Xaa Ser Xaa Cys Xaa Xaa Gly Xaa Val Xaa Xaa Gly Arg Pro
1               5                   10                  15

Xaa Asp

<210> SEQ ID NO 67
<211> LENGTH: 18
<212> TYPE: PRT
<213> ORGANISM: Burkholderia cepacia

<400> SEQUENCE: 67

Arg Leu Asp Ser Tyr Cys Phe Glu Gly Val Val Ala Pro Gly Arg Pro 1 5 10 15

Ile Asp

<210> SEQ ID NO 68
<211> LENGTH: 8
<212> TYPE: PRT
<213> ORGANISM: Burkholderia cepacia

<400> SEQUENCE: 68

Ser Glu Val Ala Thr His Gln Pro
1 5

<210> SEQ ID NO 69
<211> LENGTH: 8
<212> TYPE: PRT
<213> ORGANISM: Burkholderia cepacia
<220> FEATURE:
<221> NAME/KEY: MISC_FEATURE
<222> LOCATION: (7)..(7)
<223> OTHER INFORMATION: X is Q or P

<400> SEQUENCE: 69

Ser Glu Val Ala Thr His Xaa Pro
1 5

<210> SEQ ID NO 70
<211> LENGTH: 8
<212> TYPE: PRT
<213> ORGANISM: Burkholderia cepacia

<400> SEQUENCE: 70

Ser Glu Val Ala Thr His Pro Pro
1 5

<210> SEQ ID NO 71
<211> LENGTH: 49
<212> TYPE: PRT
<213> ORGANISM: Homo sapiens
<220> FEATURE:
<221> NAME/KEY: MISC_FEATURE
<222> LOCATION: (37)..(37)
<223> OTHER INFORMATION: X is V or L

<400> SEQUENCE: 71

Asp Ala Pro Ser Pro Leu Pro Glu Thr Thr Glu Asn Val Val Cys Ala
1 5 10 15

Leu Gly Leu Thr Val Gly Leu Val Gly Ile Ile Ile Gly Thr Ile Phe
20 25 30

Ile Ile Lys Gly Xaa Arg Lys Ser Asn Ala Ala Glu Arg Arg Gly Pro
35 40 45

Leu

<210> SEQ ID NO 72
<211> LENGTH: 49
<212> TYPE: PRT
<213> ORGANISM: Homo sapiens

<400> SEQUENCE: 72

Asp Ala Pro Ser Pro Leu Pro Glu Thr Thr Glu Asn Val Val Cys Ala
1 5 10 15

Leu Gly Leu Thr Val Gly Leu Val Gly Ile Ile Ile Gly Thr Ile Phe
20 25 30

Ile Ile Lys Gly Leu Arg Lys Ser Asn Ala Ala Glu Arg Arg Gly Pro 35 40 45

Leu

<210> SEQ ID NO 73
<211> LENGTH: 9
<212> TYPE: PRT
<213> ORGANISM: Pseudomonas aeruginosa

<400> SEQUENCE: 73

Met Arg Gln Arg Val Met Met Met Gly
1 5

<210> SEQ ID NO 74
<211> LENGTH: 9
<212> TYPE: PRT
<213> ORGANISM: Pseudomonas aeruginosa
<220> FEATURE:
<221> NAME/KEY: MISC_FEATURE
<222> LOCATION: (3)..(3)
<223> OTHER INFORMATION: X is Q or E
<220> FEATURE:
<221> NAME/KEY: MISC_FEATURE
<222> LOCATION: (6)..(6)
<223> OTHER INFORMATION: X is M or L

<400> SEQUENCE: 74

Met Arg Xaa Arg Val Xaa Met Met Gly
1 5

<210> SEQ ID NO 75
<211> LENGTH: 9
<212> TYPE: PRT
<213> ORGANISM: Pseudomonas aeruginosa

<400> SEQUENCE: 75

Met Arg Glu Arg Val Leu Met Met Gly
1 5

<210> SEQ ID NO 76
<211> LENGTH: 11
<212> TYPE: PRT
<213> ORGANISM: Homo sapiens

<400> SEQUENCE: 76

Ala Thr Ser Ser Leu Ala Val Tyr Ser Ile Leu
1 5 10

<210> SEQ ID NO 77
<211> LENGTH: 206
<212> TYPE: PRT
<213> ORGANISM: Homo sapiens

<400> SEQUENCE: 77

Lys Ile Asp Arg Leu Asp Gly Ala His Ala Pro Glu Leu Thr Lys Lys
1 5 10 15

Val Gln Arg His Ala Ser Ser Gly Ser Phe Leu Pro Ser Ala Asn Glu
20 25 30

His Leu Lys Glu Asp Leu Asn Leu Arg Leu Lys Lys Leu Thr His Ala
35 40 45

Ala Pro Cys Met Leu Phe Met Lys Gly Thr Pro Gln Glu Pro Arg Cys
50 55 60

Gly Phe Ser Lys Gln Met Val Glu Ile Leu His Lys His Asn Ile Gln
65 70 75 80

Phe Ser Ser Phe Asp Ile Phe Ser Asp Glu Glu Val Arg Gln Gly Leu
85 90 95

Lys Ala Tyr Ser Ser Trp Pro Thr Tyr Pro Gln Leu Tyr Val Ser Gly
100 105 110

Glu Leu Ile Gly Gly Leu Asp Ile Ile Lys Glu Leu Glu Ala Ser Glu
115 120 125

Glu Leu Asp Thr Ile Cys Pro Lys Ala Pro Lys Leu Glu Glu Arg Leu
130 135 140

Lys Val Leu Thr Asn Lys Ala Ser Val Met Leu Phe Met Lys Gly Asn
145 150 155 160

Lys Gln Glu Ala Lys Cys Gly Phe Ser Lys Gln Ile Leu Glu Ile Leu
165 170 175

Asn Ser Thr Gly Val Glu Tyr Glu Thr Phe Asp Ile Leu Glu Asp Glu
180 185 190

Glu Val Arg Gln Gly Leu Lys Ala Tyr Ser Asn Trp Pro Ser
195 200 205

<210> SEQ ID NO 78
<211> LENGTH: 206
<212> TYPE: PRT
<213> ORGANISM: Homo sapiens
<220> FEATURE:
<221> NAME/KEY: MISC_FEATURE
<222> LOCATION: (206)..(206)
<223> OTHER INFORMATION: X is S or T

<400> SEQUENCE: 78

Lys Ile Asp Arg Leu Asp Gly Ala His Ala Pro Glu Leu Thr Lys Lys
1 5 10 15

Val Gln Arg His Ala Ser Ser Gly Ser Phe Leu Pro Ser Ala Asn Glu
20 25 30

His Leu Lys Glu Asp Leu Asn Leu Arg Leu Lys Lys Leu Thr His Ala
35 40 45

Ala Pro Cys Met Leu Phe Met Lys Gly Thr Pro Gln Glu Pro Arg Cys
50 55 60

Gly Phe Ser Lys Gln Met Val Glu Ile Leu His Lys His Asn Ile Gln
65 70 75 80

Phe Ser Ser Phe Asp Ile Phe Ser Asp Glu Glu Val Arg Gln Gly Leu
85 90 95

Lys Ala Tyr Ser Ser Trp Pro Thr Tyr Pro Gln Leu Tyr Val Ser Gly
100 105 110

Glu Leu Ile Gly Gly Leu Asp Ile Ile Lys Glu Leu Glu Ala Ser Glu
115 120 125

Glu Leu Asp Thr Ile Cys Pro Lys Ala Pro Lys Leu Glu Glu Arg Leu
130 135 140

Lys Val Leu Thr Asn Lys Ala Ser Val Met Leu Phe Met Lys Gly Asn
145 150 155 160

Lys Gln Glu Ala Lys Cys Gly Phe Ser Lys Gln Ile Leu Glu Ile Leu
165 170 175

Asn Ser Thr Gly Val Glu Tyr Glu Thr Phe Asp Ile Leu Glu Asp Glu
180 185 190

Glu Val Arg Gln Gly Leu Lys Ala Tyr Ser Asn Trp Pro Xaa
195 200 205

<210> SEQ ID NO 79
<211> LENGTH: 206
<212> TYPE: PRT

<213> ORGANISM: Homo sapiens

<400> SEQUENCE: 79

Lys Ile Asp Arg Leu Asp Gly Ala His Ala Pro Glu Leu Thr Lys Lys
1               5                   10                  15

Val Gln Arg His Ala Ser Ser Gly Ser Phe Leu Pro Ser Ala Asn Glu
            20                  25                  30

His Leu Lys Glu Asp Leu Asn Leu Arg Leu Lys Lys Leu Thr His Ala
        35                  40                  45

Ala Pro Cys Met Leu Phe Met Lys Gly Thr Pro Gln Glu Pro Arg Cys
    50                  55                  60

Gly Phe Ser Lys Gln Met Val Glu Ile Leu His Lys His Asn Ile Gln
65                  70                  75                  80

Phe Ser Ser Phe Asp Ile Phe Ser Asp Glu Glu Val Arg Gln Gly Leu
                85                  90                  95

Lys Ala Tyr Ser Ser Trp Pro Thr Tyr Pro Gln Leu Tyr Val Ser Gly
            100                 105                 110

Glu Leu Ile Gly Gly Leu Asp Ile Ile Lys Glu Leu Glu Ala Ser Glu
        115                 120                 125

Glu Leu Asp Thr Ile Cys Pro Lys Ala Pro Lys Leu Glu Glu Arg Leu
    130                 135                 140

Lys Val Leu Thr Asn Lys Ala Ser Val Met Leu Phe Met Lys Gly Asn
145                 150                 155                 160

Lys Gln Glu Ala Lys Cys Gly Phe Ser Lys Gln Ile Leu Glu Ile Leu
                165                 170                 175

Asn Ser Thr Gly Val Glu Tyr Glu Thr Phe Asp Ile Leu Glu Asp Glu
            180                 185                 190

Glu Val Arg Gln Gly Leu Lys Ala Tyr Ser Asn Trp Pro Thr
        195                 200                 205

<210> SEQ ID NO 80
<211> LENGTH: 21
<212> TYPE: PRT
<213> ORGANISM: Burkholderia cepacia

<400> SEQUENCE: 80

Pro Pro Asn Asn Pro Pro Pro Asn Thr Asn Tyr Leu Thr Pro Thr Pro
1               5                   10                  15

His Asn His Gly Lys
            20

<210> SEQ ID NO 81
<211> LENGTH: 26
<212> TYPE: PRT
<213> ORGANISM: Burkholderia cepacia
<220> FEATURE:
<221> NAME/KEY: MISC_FEATURE
<222> LOCATION: (2)..(2)
<223> OTHER INFORMATION: X is P or A
<220> FEATURE:
<221> NAME/KEY: MISC_FEATURE
<222> LOCATION: (3)..(3)
<223> OTHER INFORMATION: X is N or T
<220> FEATURE:
<221> NAME/KEY: MISC_FEATURE
<222> LOCATION: (6)..(6)
<223> OTHER INFORMATION: X is Y or absent
<220> FEATURE:
<221> NAME/KEY: MISC_FEATURE
<222> LOCATION: (11)..(11)
<223> OTHER INFORMATION: X is W or absent
<220> FEATURE:

<221> NAME/KEY: MISC_FEATURE
<222> LOCATION: (12)..(12)
<223> OTHER INFORMATION: X is N or S
<220> FEATURE:
<221> NAME/KEY: MISC_FEATURE
<222> LOCATION: (14)..(14)
<223> OTHER INFORMATION: X is A or absent
<220> FEATURE:
<221> NAME/KEY: MISC_FEATURE
<222> LOCATION: (15)..(15)
<223> OTHER INFORMATION: X is K or absent
<220> FEATURE:
<221> NAME/KEY: MISC_FEATURE
<222> LOCATION: (16)..(16)
<223> OTHER INFORMATION: X is S or absent
<220> FEATURE:
<221> NAME/KEY: MISC_FEATURE
<222> LOCATION: (17)..(17)
<223> OTHER INFORMATION: X is L or I
<220> FEATURE:
<221> NAME/KEY: MISC_FEATURE
<222> LOCATION: (18)..(18)
<223> OTHER INFORMATION: X is T or A
<220> FEATURE:
<221> NAME/KEY: MISC_FEATURE
<222> LOCATION: (20)..(20)
<223> OTHER INFORMATION: X is T or Y
<220> FEATURE:
<221> NAME/KEY: MISC_FEATURE
<222> LOCATION: (23)..(23)
<223> OTHER INFORMATION: X is N or D
<220> FEATURE:
<221> NAME/KEY: MISC_FEATURE
<222> LOCATION: (24)..(24)
<223> OTHER INFORMATION: X is H or P
<220> FEATURE:
<221> NAME/KEY: MISC_FEATURE
<222> LOCATION: (25)..(25)
<223> OTHER INFORMATION: X is G or A

<400> SEQUENCE: 81

```
Pro Xaa Xaa Asn Pro Xaa Pro Pro Asn Thr Xaa Xaa Tyr Xaa Xaa Xaa
1               5                   10                  15

Xaa Xaa Pro Xaa Pro His Xaa Xaa Xaa Lys
            20                  25
```

<210> SEQ ID NO 82
<211> LENGTH: 26
<212> TYPE: PRT
<213> ORGANISM: Burkholderia cepacia

<400> SEQUENCE: 82

```
Pro Ala Thr Asn Pro Tyr Pro Pro Asn Thr Trp Ser Tyr Ala Lys Ser
1               5                   10                  15

Ile Ala Pro Tyr Pro His Asp Pro Ala Lys
            20                  25
```

<210> SEQ ID NO 83
<211> LENGTH: 20
<212> TYPE: PRT
<213> ORGANISM: Pseudomonas aeruginosa

<400> SEQUENCE: 83

```
Val Arg Ser Cys Thr Pro Ala Trp Val Thr Glu Arg Asn Phe Ile Ser
1               5                   10                  15

Lys Lys Lys Gly
            20
```

<210> SEQ ID NO 84
<211> LENGTH: 20

```
<212> TYPE: PRT
<213> ORGANISM: Pseudomonas aeruginosa
<220> FEATURE:
<221> NAME/KEY: MISC_FEATURE
<222> LOCATION: (2)..(2)
<223> OTHER INFORMATION: X is R or Q
<220> FEATURE:
<221> NAME/KEY: MISC_FEATURE
<222> LOCATION: (4)..(4)
<223> OTHER INFORMATION: X is C or S
<220> FEATURE:
<221> NAME/KEY: MISC_FEATURE
<222> LOCATION: (10)..(10)
<223> OTHER INFORMATION: X is T or S
<220> FEATURE:
<221> NAME/KEY: MISC_FEATURE
<222> LOCATION: (11)..(11)
<223> OTHER INFORMATION: X is E or D
<220> FEATURE:
<221> NAME/KEY: MISC_FEATURE
<222> LOCATION: (12)..(12)
<223> OTHER INFORMATION: X is R or I
<220> FEATURE:
<221> NAME/KEY: MISC_FEATURE
<222> LOCATION: (13)..(13)
<223> OTHER INFORMATION: X is N or T
<220> FEATURE:
<221> NAME/KEY: MISC_FEATURE
<222> LOCATION: (14)..(14)
<223> OTHER INFORMATION: X is F or Y
<220> FEATURE:
<221> NAME/KEY: MISC_FEATURE
<222> LOCATION: (16)..(16)
<223> OTHER INFORMATION: X is S or A
<220> FEATURE:
<221> NAME/KEY: MISC_FEATURE
<222> LOCATION: (17)..(17)
<223> OTHER INFORMATION: X is K or T
<220> FEATURE:
<221> NAME/KEY: MISC_FEATURE
<222> LOCATION: (19)..(19)
<223> OTHER INFORMATION: X is K or E

<400> SEQUENCE: 84

Val Xaa Ser Xaa Thr Pro Ala Trp Val Xaa Xaa Xaa Xaa Xaa Ile Xaa
1               5                   10                  15

Xaa Lys Xaa Gly
            20


<210> SEQ ID NO 85
<211> LENGTH: 20
<212> TYPE: PRT
<213> ORGANISM: Pseudomonas aeruginosa

<400> SEQUENCE: 85

Val Gln Ser Ser Thr Pro Ala Trp Val Ser Asp Ile Thr Tyr Ile Ala
1               5                   10                  15

Thr Lys Glu Gly
            20


<210> SEQ ID NO 86
<211> LENGTH: 6
<212> TYPE: PRT
<213> ORGANISM: Pseudomonas aeruginosa

<400> SEQUENCE: 86

Asn Ser Thr Phe Thr Ser
1               5


<210> SEQ ID NO 87
<211> LENGTH: 20
```

```
<212> TYPE: PRT
<213> ORGANISM: Campylobacter jejuni

<400> SEQUENCE: 87

Ile Ser Pro Phe Thr Val Thr Lys His Lys Pro Thr Ser Gln Gly Leu
1               5                   10                  15

Glu Tyr Leu His
            20


<210> SEQ ID NO 88
<211> LENGTH: 20
<212> TYPE: PRT
<213> ORGANISM: Campylobacter jejuni
<220> FEATURE:
<221> NAME/KEY: MISC_FEATURE
<222> LOCATION: (2)..(2)
<223> OTHER INFORMATION: X is S or P
<220> FEATURE:
<221> NAME/KEY: MISC_FEATURE
<222> LOCATION: (5)..(5)
<223> OTHER INFORMATION: X is T or K
<220> FEATURE:
<221> NAME/KEY: MISC_FEATURE
<222> LOCATION: (6)..(6)
<223> OTHER INFORMATION: X is V or L
<220> FEATURE:
<221> NAME/KEY: MISC_FEATURE
<222> LOCATION: (9)..(9)
<223> OTHER INFORMATION: X is H or N
<220> FEATURE:
<221> NAME/KEY: MISC_FEATURE
<222> LOCATION: (12)..(12)
<223> OTHER INFORMATION: X is T or absent
<220> FEATURE:
<221> NAME/KEY: MISC_FEATURE
<222> LOCATION: (13)..(13)
<223> OTHER INFORMATION: X is S or absent
<220> FEATURE:
<221> NAME/KEY: MISC_FEATURE
<222> LOCATION: (14)..(14)
<223> OTHER INFORMATION: X is Q or absent
<220> FEATURE:
<221> NAME/KEY: MISC_FEATURE
<222> LOCATION: (15)..(15)
<223> OTHER INFORMATION: X is G or absent
<220> FEATURE:
<221> NAME/KEY: MISC_FEATURE
<222> LOCATION: (19)..(19)
<223> OTHER INFORMATION: X is L or A

<400> SEQUENCE: 88

Ile Xaa Pro Phe Xaa Xaa Thr Lys Xaa Lys Pro Xaa Xaa Xaa Xaa Leu
1               5                   10                  15

Glu Tyr Xaa His
            20


<210> SEQ ID NO 89
<211> LENGTH: 16
<212> TYPE: PRT
<213> ORGANISM: Campylobacter jejuni

<400> SEQUENCE: 89

Ile Pro Pro Phe Lys Leu Thr Lys Asn Lys Pro Leu Glu Tyr Ala His
1               5                   10                  15


<210> SEQ ID NO 90
<211> LENGTH: 60
<212> TYPE: PRT
<213> ORGANISM: Pseudomonas aeruginosa

<400> SEQUENCE: 90
```

Gly Arg Gly Arg Pro Ser Pro Leu His Val Ala Gln His Ser Tyr Thr
1               5                   10                  15

Gly Val Glu Ala Gln Pro Leu Asn His Gln Val Leu His Val Ala Gly
            20                  25                  30

Arg Asp Gly Leu Pro Val Ala Val Asn Gly Thr Leu Ser Asp Asp Asp
        35                  40                  45

Asp Val Gln Ser Gly Pro Thr Ala Pro Ser Leu Thr
    50                  55                  60

<210> SEQ ID NO 91
<211> LENGTH: 60
<212> TYPE: PRT
<213> ORGANISM: Pseudomonas aeruginosa
<220> FEATURE:
<221> NAME/KEY: MISC_FEATURE
<222> LOCATION: (2)..(2)
<223> OTHER INFORMATION: X is R or K
<220> FEATURE:
<221> NAME/KEY: MISC_FEATURE
<222> LOCATION: (4)..(4)
<223> OTHER INFORMATION: X is R or W
<220> FEATURE:
<221> NAME/KEY: MISC_FEATURE
<222> LOCATION: (6)..(6)
<223> OTHER INFORMATION: X is S or Q
<220> FEATURE:
<221> NAME/KEY: MISC_FEATURE
<222> LOCATION: (9)..(9)
<223> OTHER INFORMATION: X is H or E
<220> FEATURE:
<221> NAME/KEY: MISC_FEATURE
<222> LOCATION: (10)..(10)
<223> OTHER INFORMATION: X is V or I
<220> FEATURE:
<221> NAME/KEY: MISC_FEATURE
<222> LOCATION: (11)..(11)
<223> OTHER INFORMATION: X is A or E
<220> FEATURE:
<221> NAME/KEY: MISC_FEATURE
<222> LOCATION: (12)..(12)
<223> OTHER INFORMATION: X is Q or E
<220> FEATURE:
<221> NAME/KEY: MISC_FEATURE
<222> LOCATION: (15)..(15)
<223> OTHER INFORMATION: X is Y or H
<220> FEATURE:
<221> NAME/KEY: MISC_FEATURE
<222> LOCATION: (16)..(16)
<223> OTHER INFORMATION: X is T or A
<220> FEATURE:
<221> NAME/KEY: MISC_FEATURE
<222> LOCATION: (17)..(17)
<223> OTHER INFORMATION: X is G or D
<220> FEATURE:
<221> NAME/KEY: MISC_FEATURE
<222> LOCATION: (18)..(18)
<223> OTHER INFORMATION: X is V or L
<220> FEATURE:
<221> NAME/KEY: MISC_FEATURE
<222> LOCATION: (19)..(19)
<223> OTHER INFORMATION: X is E or A
<220> FEATURE:
<221> NAME/KEY: MISC_FEATURE
<222> LOCATION: (20)..(20)
<223> OTHER INFORMATION: X is A or N
<220> FEATURE:
<221> NAME/KEY: MISC_FEATURE
<222> LOCATION: (21)..(21)
<223> OTHER INFORMATION: X is Q or G
<220> FEATURE:
<221> NAME/KEY: MISC_FEATURE
<222> LOCATION: (22)..(22)
<223> OTHER INFORMATION: X is P or absent
<220> FEATURE:

```
<221> NAME/KEY: MISC_FEATURE
<222> LOCATION: (23)..(23)
<223> OTHER INFORMATION: X is L or absent
<220> FEATURE:
<221> NAME/KEY: MISC_FEATURE
<222> LOCATION: (24)..(24)
<223> OTHER INFORMATION: X is N or absent
<220> FEATURE:
<221> NAME/KEY: MISC_FEATURE
<222> LOCATION: (25)..(25)
<223> OTHER INFORMATION: X is H or absent
<220> FEATURE:
<221> NAME/KEY: MISC_FEATURE
<222> LOCATION: (26)..(26)
<223> OTHER INFORMATION: X is Q or absent
<220> FEATURE:
<221> NAME/KEY: MISC_FEATURE
<222> LOCATION: (27)..(27)
<223> OTHER INFORMATION: X is V or absent
<220> FEATURE:
<221> NAME/KEY: MISC_FEATURE
<222> LOCATION: (28)..(28)
<223> OTHER INFORMATION: X is L or absent
<220> FEATURE:
<221> NAME/KEY: MISC_FEATURE
<222> LOCATION: (29)..(29)
<223> OTHER INFORMATION: X is H or Y
<220> FEATURE:
<221> NAME/KEY: MISC_FEATURE
<222> LOCATION: (33)..(33)
<223> OTHER INFORMATION: X is R or A
<220> FEATURE:
<221> NAME/KEY: MISC_FEATURE
<222> LOCATION: (34)..(34)
<223> OTHER INFORMATION: X is D or S
<220> FEATURE:
<221> NAME/KEY: MISC_FEATURE
<222> LOCATION: (38)..(38)
<223> OTHER INFORMATION: X is V or F
<220> FEATURE:
<221> NAME/KEY: MISC_FEATURE
<222> LOCATION: (41)..(41)
<223> OTHER INFORMATION: X is N or L
<220> FEATURE:
<221> NAME/KEY: MISC_FEATURE
<222> LOCATION: (42)..(42)
<223> OTHER INFORMATION: X is G or R
<220> FEATURE:
<221> NAME/KEY: MISC_FEATURE
<222> LOCATION: (43)..(43)
<223> OTHER INFORMATION: X is T or A
<220> FEATURE:
<221> NAME/KEY: MISC_FEATURE
<222> LOCATION: (44)..(44)
<223> OTHER INFORMATION: X is L or Y
<220> FEATURE:
<221> NAME/KEY: MISC_FEATURE
<222> LOCATION: (45)..(45)
<223> OTHER INFORMATION: X is S or A
<220> FEATURE:
<221> NAME/KEY: MISC_FEATURE
<222> LOCATION: (46)..(46)
<223> OTHER INFORMATION: X is D or G
<220> FEATURE:
<221> NAME/KEY: MISC_FEATURE
<222> LOCATION: (47)..(47)
<223> OTHER INFORMATION: X is D or S
<220> FEATURE:
<221> NAME/KEY: MISC_FEATURE
<222> LOCATION: (49)..(49)
<223> OTHER INFORMATION: X is D or L
<220> FEATURE:
<221> NAME/KEY: MISC_FEATURE
<222> LOCATION: (50)..(50)
<223> OTHER INFORMATION: X is V or P
<220> FEATURE:
<221> NAME/KEY: MISC_FEATURE
<222> LOCATION: (51)..(51)
<223> OTHER INFORMATION: X is Q or K
```

<220> FEATURE:
<221> NAME/KEY: MISC_FEATURE
<222> LOCATION: (52)..(52)
<223> OTHER INFORMATION: X is S or V
<220> FEATURE:
<221> NAME/KEY: MISC_FEATURE
<222> LOCATION: (53)..(53)
<223> OTHER INFORMATION: X is G or N
<220> FEATURE:
<221> NAME/KEY: MISC_FEATURE
<222> LOCATION: (55)..(55)
<223> OTHER INFORMATION: X is T or L
<220> FEATURE:
<221> NAME/KEY: MISC_FEATURE
<222> LOCATION: (56)..(56)
<223> OTHER INFORMATION: X is A or I
<220> FEATURE:
<221> NAME/KEY: MISC_FEATURE
<222> LOCATION: (57)..(57)
<223> OTHER INFORMATION: X is P or R
<220> FEATURE:
<221> NAME/KEY: MISC_FEATURE
<222> LOCATION: (59)..(59)
<223> OTHER INFORMATION: X is L or V

<400> SEQUENCE: 91

```
Gly Xaa Gly Xaa Pro Xaa Pro Leu Xaa Xaa Xaa Xaa His Ser Xaa Xaa
1               5                   10                  15

Xaa Xaa Xaa Xaa Xaa Xaa Xaa Xaa Xaa Xaa Xaa Xaa Xaa Val Ala Gly
            20                  25                  30

Xaa Xaa Gly Leu Pro Xaa Ala Val Xaa Xaa Xaa Xaa Xaa Xaa Xaa Asp
        35                  40                  45

Xaa Xaa Xaa Xaa Xaa Pro Xaa Xaa Xaa Ser Xaa Thr
    50                  55                  60
```

<210> SEQ ID NO 92
<211> LENGTH: 53
<212> TYPE: PRT
<213> ORGANISM: Pseudomonas aeruginosa

<400> SEQUENCE: 92

```
Gly Lys Gly Trp Pro Gln Pro Leu Glu Ile Glu Glu His Ser His Ala
1               5                   10                  15

Asp Leu Ala Asn Gly Tyr Val Ala Gly Ala Ser Gly Leu Pro Phe Ala
            20                  25                  30

Val Leu Arg Ala Tyr Ala Gly Ser Asp Leu Pro Lys Val Asn Pro Leu
        35                  40                  45

Ile Arg Ser Val Thr
    50
```

<210> SEQ ID NO 93
<211> LENGTH: 9
<212> TYPE: PRT
<213> ORGANISM: Streptomyces sp. NRRL B-24720

<400> SEQUENCE: 93

```
Arg Met Ala Arg Ser Ser Trp Arg Arg
1               5
```

<210> SEQ ID NO 94
<211> LENGTH: 9
<212> TYPE: PRT
<213> ORGANISM: Streptomyces sp. NRRL B-24720
<220> FEATURE:
<221> NAME/KEY: MISC_FEATURE
<222> LOCATION: (3)..(3)
<223> OTHER INFORMATION: X is A or V

```
<220> FEATURE:
<221> NAME/KEY: MISC_FEATURE
<222> LOCATION: (6)..(6)
<223> OTHER INFORMATION: X is S or A

<400> SEQUENCE: 94

Arg Met Xaa Arg Ser Xaa Trp Arg Arg
1               5


<210> SEQ ID NO 95
<211> LENGTH: 9
<212> TYPE: PRT
<213> ORGANISM: Streptomyces sp. NRRL B-24720

<400> SEQUENCE: 95

Arg Met Val Arg Ser Ala Trp Arg Arg
1               5


<210> SEQ ID NO 96
<211> LENGTH: 8
<212> TYPE: PRT
<213> ORGANISM: Pseudomonas aeruginosa

<400> SEQUENCE: 96

Leu Phe Ala Ala Leu Thr Val Pro
1               5
```